(12) United States Patent
Su

(10) Patent No.: US 9,181,231 B2
(45) Date of Patent: Nov. 10, 2015

(54) PYRUVATE KINASE ACTIVATORS FOR USE FOR INCREASING LIFETIME OF THE RED BLOOD CELLS AND TREATING ANEMIA

(75) Inventor: Shin-San M. Su, Newton, MA (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 44 days.

(21) Appl. No.: 14/115,286

(22) PCT Filed: May 3, 2012

(86) PCT No.: PCT/US2012/036390
§ 371 (c)(1),
(2), (4) Date: Feb. 14, 2014

(87) PCT Pub. No.: WO2012/151440
PCT Pub. Date: Nov. 8, 2012

(65) Prior Publication Data
US 2014/0179694 A1 Jun. 26, 2014

Related U.S. Application Data

(60) Provisional application No. 61/482,161, filed on May 3, 2011, provisional application No. 61/482,156, filed on May 3, 2011, provisional application No. 61/482,148, filed on May 3, 2011, provisional application No. 61/482,103, filed on May 3, 2011, provisional application No. 61/482,163, filed on May 3, 2011, provisional application No. 61/482,149, filed on May 3, 2011, provisional application No. 61/482,153, filed on May 3, 2011.

(51) Int. Cl.
| | |
|---|---|
| *A61K 31/535* | (2006.01) |
| *A61K 31/497* | (2006.01) |
| *A01N 1/02* | (2006.01) |
| *C07D 413/12* | (2006.01) |
| *A61K 31/385* | (2006.01) |
| *A61K 31/39* | (2006.01) |
| *A61K 31/423* | (2006.01) |
| *A61K 31/428* | (2006.01) |
| *A61K 31/4439* | (2006.01) |
| *A61K 31/495* | (2006.01) |
| *A61K 31/496* | (2006.01) |
| *A61K 31/498* | (2006.01) |
| *A61K 31/536* | (2006.01) |
| *A61K 31/538* | (2006.01) |
| *C07D 241/44* | (2006.01) |
| *C07D 265/18* | (2006.01) |
| *C07D 265/36* | (2006.01) |
| *C07D 319/18* | (2006.01) |

(52) U.S. Cl.
CPC ............ *C07D 413/12* (2013.01); *A61K 31/385* (2013.01); *A61K 31/39* (2013.01); *A61K 31/423* (2013.01); *A61K 31/428* (2013.01); *A61K 31/4439* (2013.01); *A61K 31/495* (2013.01); *A61K 31/496* (2013.01); *A61K 31/497* (2013.01); *A61K 31/498* (2013.01); *A61K 31/535* (2013.01); *A61K 31/536* (2013.01); *A61K 31/538* (2013.01); *C07D 241/44* (2013.01); *C07D 265/18* (2013.01); *C07D 265/36* (2013.01); *C07D 319/18* (2013.01)

(58) Field of Classification Search
CPC .......................... A61K 31/535; A61K 31/495
USPC ................... 514/230.5, 249, 254.11
See application file for complete search history.

(56) References Cited

U.S. PATENT DOCUMENTS

| | | | |
|---|---|---|---|
| 3,046,122 A | 7/1962 | Oskar Siis et al. | |
| 3,097,210 A | 7/1963 | Bicking | |
| 4,474,599 A | 10/1984 | Rogers et al. | |
| 4,775,762 A | 10/1988 | Knox et al. | |
| 4,849,424 A | 7/1989 | Ikeda et al. | |
| 4,881,965 A | 11/1989 | Yamamoto et al. | |
| 4,889,553 A | 12/1989 | Rowson et al. | |
| 4,959,094 A | 9/1990 | Wegner et al. | |
| 5,122,530 A | 6/1992 | Tomioka et al. | |
| 5,180,732 A | 1/1993 | Tomioka et al. | |
| 5,220,028 A | 6/1993 | Iwasawa et al. | |
| 5,252,590 A | 10/1993 | Tomioka et al. | |
| 5,719,167 A * | 2/1998 | Doshi et al. ................ | 514/337 |
| 6,150,356 A | 11/2000 | Lloyd et al. | |
| 6,172,005 B1 | 1/2001 | Selby | |
| 6,492,368 B1 | 12/2002 | Dorsch et al. | |
| 6,511,977 B1 | 1/2003 | Lloyd et al. | |
| 6,818,631 B1 | 11/2004 | Nakagawa et al. | |
| 7,071,199 B1 * | 7/2006 | Hirst et al. ................ | 514/260.1 |
| 7,091,201 B2 * | 8/2006 | Weller et al. ............... | 514/235.8 |

(Continued)

FOREIGN PATENT DOCUMENTS

| | | |
|---|---|---|
| CA | 2235621 A1 | 5/1997 |
| DE | 3813886 A1 | 11/1989 |

(Continued)

OTHER PUBLICATIONS

Adveenko, et al, "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.

(Continued)

*Primary Examiner* — Raymond Henley, III
(74) *Attorney, Agent, or Firm* — Lando & Anastasi LLP

(57) ABSTRACT

Described herein are methods for using compounds that activate pyruvate kinase.

72 Claims, No Drawings

(56) References Cited

U.S. PATENT DOCUMENTS

| | | | |
|---|---|---|---|
| 7,288,554 B2 | 10/2007 | Finkelstein et al. | |
| 7,524,848 B2 | 4/2009 | Powers et al. | |
| 7,560,551 B2 * | 7/2009 | Cee et al. ............ | 544/237 |
| 7,863,444 B2 | 1/2011 | Calderwood et al. | |
| 8,642,660 B2 | 2/2014 | Goldfarb | |
| 8,742,119 B2 | 6/2014 | Salituro et al. | |
| 2003/0187001 A1 | 10/2003 | Calderwood et al. | |
| 2004/0198979 A1 | 10/2004 | Dhanak et al. | |
| 2007/0282101 A1 | 12/2007 | Ericsson et al. | |
| 2008/0004269 A1 | 1/2008 | Xu et al. | |
| 2008/0051414 A1 | 2/2008 | Hurley et al. | |
| 2009/0054453 A1 | 2/2009 | Alcaraz et al. | |
| 2009/0163545 A1 | 6/2009 | Goldfarb | |
| 2009/0247499 A1 | 10/2009 | Fletcher et al. | |
| 2010/0105657 A1 | 4/2010 | Nordvall et al. | |
| 2011/0224252 A1 | 9/2011 | Dumeunier et al. | |

FOREIGN PATENT DOCUMENTS

| | | |
|---|---|---|
| EP | 0246749 A2 | 11/1987 |
| EP | 0628551 A1 | 12/1994 |
| IT | 1176770 B | 8/1987 |
| JP | S61129129 A | 6/1986 |
| JP | 06-025177 | 2/1994 |
| JP | 2002-193710 A | 7/2002 |
| JP | 2007/238458 A | 9/2007 |
| WO | 8501289 A1 | 3/1985 |
| WO | 9211761 A1 | 7/1992 |
| WO | 97/28141 A1 | 8/1997 |
| WO | 99/16751 A1 | 4/1999 |
| WO | 9916751 A1 | 4/1999 |
| WO | 9948490 A1 | 9/1999 |
| WO | 0017202 A1 | 3/2000 |
| WO | 01/07440 A1 | 2/2001 |
| WO | 03/022277 A1 | 3/2003 |
| WO | 03/037252 A2 | 5/2003 |
| WO | 03/062235 A1 | 7/2003 |
| WO | 03/076422 A1 | 9/2003 |
| WO | 03093297 A2 | 11/2003 |
| WO | 2004/004730 A2 | 1/2004 |
| WO | 2004014851 A2 | 2/2004 |
| WO | 2004/037251 A1 | 5/2004 |
| WO | 2006043950 A1 | 4/2006 |
| WO | 2006052190 A1 | 5/2006 |
| WO | 2006117762 A2 | 11/2006 |
| WO | 2007019346 A1 | 2/2007 |
| WO | 2008/019139 A2 | 2/2008 |
| WO | 2008024284 A2 | 2/2008 |
| WO | 2008/026658 A1 | 3/2008 |
| WO | 2008047198 A1 | 4/2008 |
| WO | 2009012430 A1 | 1/2009 |
| WO | 2009/053102 A1 | 4/2009 |
| WO | 2009086303 A2 | 7/2009 |
| WO | 2010/042867 A2 | 4/2010 |
| WO | 2010/129596 A1 | 11/2010 |
| WO | 2011002817 A1 | 1/2011 |
| WO | 2011094708 A2 | 8/2011 |
| WO | 2011137089 A1 | 11/2011 |

OTHER PUBLICATIONS

Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853,.
Boxer et al. "Identification of activators for the M2 isoform of human pyruvate kinase Version 3" Probe Reports from the NIH Molecular Libraries Program [Internet] (2009) pp. 1-25.
Cecil Textbook of Medicine, edited by Bennet, J.C., and Plum F., 20th edition, vol. 1, 1004-1010, 1996.
Cohen et al., "The development and therapeutic potential of protein kinase inhibitors", Current Opinion in Chemical Biology, 3,459-465, 1999.
Crawford et al., Caplus an 2010:1218943.
Database Chemcats, Chemical Abstracts Service, Columbus, OH, US "Bionet Screening Compounds" Key Organics Ltd., Camelford, Cornwall (2001).
Dermer et al., "Another Anniversary for the War on Cancer", Bio/Technology, 1994, 12:320.
Dombrauckas, et al., Structural Basis for Tumor Pyruvate Kinasa M2 Allosteric Regulation and Catalysis, Biochemistry, vol. 44, pg. 9717-9429 (2005).
European Search report for EP Application No. 10 794 667.5 dated Oct. 9, 2013.
European Search Report for European Application No. 11811257.2 dated Apr. 23, 2014.
Fabbro et al. "Protein kinases as targets for anticancer agents: from inhibitors to useful drugs." Pharmacology & Therapeutics 93, 79-98, 2002.
Freshney et al.,Culture of Animal Cells, A Manual of Basic Technique, Alan R. Liss, Inc., 1983, New York, p4.
Golub et al., "Molecular Classification of Cancer: Class Discovery and Class Prediction by Gene Expression Monitoring", Science, 286, 531-537, 1999.
Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.
International Search Report & Written Opinion for PCT/US10/030139 dated Dec. 10, 2010.
International Search Report & Written Opinion for PCT/US10/40485 dated Aug. 11, 2010.
International Search Report and Written Opinion for International Application No. PCT/US2012/036390 dated Sep. 21, 2012.
International Search Report dated May 3, 2012 for related application PCT/US2011/066595.
International Search Report for PCT/US2010/033610 dated Jul. 22, 2010.
Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.
Mass, R. D., "The Her receptor family: a rich target for therapeutic development", Int. J. Radiation Oncology Bio. Phys.vol. 58(3): 932-940, 2004.
Patel et al. "Synthesis of some new idolinone derivatives containing piperazine moiety" Bulgarian Chemical Communications, 2003 Bol 35 No. 4 pp. 242-244.
Proisy et al. "Rapid Synthesis of 3-Aminoisoquinoline-5-sulfonamides Using the Buchwald-Hartwig Reaction" Synthesis 2009, No. 4, pp0561-0566.
Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.
Supplemental EP Search Report & Written Opinion for EP 10 79 4667 dated Jan. 15, 2013.
Supplemental EP Search Report for European Application No. 10714131.9 dated Oct. 17, 2014.
Tawaka, et al., Caplus an 1998:794998.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Wong et al. "PKM2, a Central Point of Regulation in Cancer Metabolism" International Journal of Cell Biology (2013) vol. 2013, pp. 1-11.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.

* cited by examiner

PYRUVATE KINASE ACTIVATORS FOR USE FOR INCREASING LIFETIME OF THE RED BLOOD CELLS AND TREATING ANEMIA

This application is a national stage application under 35 U.S.C. §371 of International Application No. PCT/US2012/036390, filed May 3, 2012, and published as International Publication No. WO 2012/151440 on Nov. 8, 2012, which claims priority from U.S. Ser. No. 61/482,103, filed May 3, 2011; U.S. Ser. No. 61/482,148, filed May 3, 2011; U.S. Ser. No. 61/482,149, filed May 3, 2011; U.S. Ser. No. 61/482,153, filed May 3, 2011; U.S. Ser. No. 61/482,156, filed May 3, 2011; U.S. Ser. No. 61/482,161, filed May 3, 2011; and U.S. Ser. No. 61/482,163, filed May 3, 2011. The contents of each of these applications is incorporated herein by reference in its entirety.

Pyruvate kinase deficiency (PKD) is one of the most common enzyme defects in erythrocytes in human due to autosomal recessive mutations of the PKLR gene (Zanella, A., et al., Br J Haematol 2005, 130 (1), 11-25). It is also the most frequent enzyme mutation in the central glycolytic pathway and only second to glucose-6 phosphate dehydrogenase (G6PD) deficiency (Kedar, P., et al., Clin Genet. 2009, 75 (2), 157-62) of the hexose monophosphate shunt.

Human erythrocytes are unique in that they anucleate when mature. Immature erythocytes have nuclei but during early erythropoiesis prior to becoming circulating reticulocytes they extrude nuclei as well as other organelles such as mitochondria, endoplasmic reticulum, and golgi aparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate $NAD^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., Exp Hematol 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. Blood 2000, 95 (11), 3585-8), there is no disease-modifying treatment available for these patients other than palliative care (Tavazzi, D. et al., Pediatr Ann 2008, 37 (5), 303-10). These hereditary non-spherocytic hemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}$>Met associated with a HNSHA patient (Kanno, H. et al., Proc Natl Acad Sci USA 1991, 88 (18), 8218-21), there are now nearly 200 different reported mutations associated with this disease reported worldwide (Zanella, A. et al., Br J Haematol 2005, 130 (1), 11-25; Kedar, P., et al., Clin Genet. 2009, 75 (2), 157-62; Fermo, E. et al., Br J Haematol 2005, 129 (6), 839-46; Pissard, S. et al., Br J Haematol 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}$>Trp and $Arg^{510}$>Gln, while mutations $Arg^{479}$>His, $Arg^{490}$>Trp and $Asp^{331}$>Gly were more frequently found in Asian patients (Kedar, P., et al., Clin Genet. 2009, 75 (2), 157-62).

The present invention provides a method for increasing lifetime of the red blood cells (RBCs) in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention further provides a method for regulating 2,3-diphosphoglycerate levels in blood in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention also provides a method for treating hereditary non-spherocytic hemolytic anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating sickle cell anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating thalassemia (e.g. beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxyhemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

In one aspect, the invention features a compound of formula (I):

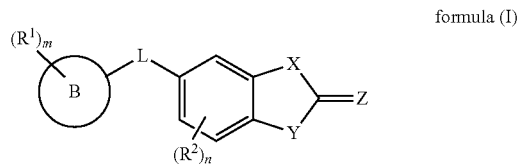

formula (I)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 1 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —$SO_2$—, —$SO_2NR^a$— and —$NR^aSO_2$—;

each $R^a$ is independently selected from hydrogen and $C_1$-$C_6$ alkyl;

X and Y are each independently selected from O, S, $NR^b$ and $CH_2$, wherein at least one of X and Y is O or S;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

In some embodiments of formula (I), each $R^1$ is independently selected from $C_1$-$C_6$ alkyl, $C_1$-$C_6$ alkoxy, $C_1$-$C_6$ haloalkyl, halo, acetyl and $NO_2$;

In some embodiments of formula (I), each $R^b$ is independently selected from hydrogen and $C_1$-$C_6$ alkyl.

In some embodiments of formula (I), B is a monocyclic heteroaryl, cycloalkyl, heterocyclyl, $C_{1-6}$ aralkyl, or $C_{1-6}$ heteroaralkyl.

In some embodiments of formula (I), B is a monocyclic heterocyclyl (e.g., a 6-membered monocyclic heterocyclyl). In some embodiments of formula (I), B is a 6-membered nitrogen containing monocyclic heterocyclyl (e.g., piperazinyl). In some embodiments of formula (I), B is unsubstituted piperazinyl. In some embodiments of formula (I), B is piperazinyl substituted with an $R^1$. In some embodiments of formula (I), B is a 7-membered nitrogen containing monocyclic heterocyclyl (e.g., 1,4-diazepam). In some embodiments of formula (I), B is unsubstituted 1,4-diazepam. In some embodiments of formula (I), B is 1,4-diazepam substituted with an $R^1$.

In some embodiments of formula (I), B is a monocyclic heteroaryl. In some embodiments of formula (I), B is a 5-membered monocyclic heteroaryl (e.g., thiophenyl). In some embodiments of formula (I), B is a 6-membered monocyclic heteroaryl, e.g., a 6-membered nitrogen-containing monocyclic heteroaryl (e.g., pyridyl). In some embodiments of formula (I), B is pyridyl substituted with 2 $R^1$. In some embodiments of formula (I), one $R^1$ is halo and the other is haloalkyl. In some embodiments of formula (I), one $R^1$ is chloro and the other is trifluoromethyl.

In some embodiments of formula (I), B is monocyclic aryl (e.g., phenyl). In some embodiments of formula (I), B is unsubstituted phenyl. In some embodiments of formula (I), B is phenyl substituted with one $R^1$. In some embodiments of formula (I), B is phenyl substituted with two $R^1$.

In some embodiments of formula (I), n is 1. In some embodiments of formula (I), $R^2$ is $C_1$-$C_6$ alkyl (e.g., methyl). In some embodiments of formula (I), $R^2$ is halo (e.g., fluoro, chloro or bromo).

In some embodiments of formula (I), L is a linker selected from $-SO_2-$. In some embodiments of formula (I), L is a linker selected from $-SO_2NR^a-$ and $-NR^aSO_2-$. In some embodiments of formula (I), L is $-SO_2NR^a-$. In some embodiments of formula (I), $R^a$ is hydrogen. In some embodiments of formula (I), $R^a$ is $C_1$-$C_6$ alkyl (e.g., methyl, ethyl or isopropyl). In some embodiments of formula (I), L is $-NR^aSO_2-$. In some embodiments of formula (I), $R^a$ is hydrogen. In some embodiments of formula (I), $R^a$ is $C_1$-$C_6$ alkyl (e.g., methyl, ethyl or isopropyl).

In some embodiments of formula (I), X is S. In some embodiments of formula (I), X is O. In some embodiments of formula (I), X is $NR^b$. In some embodiments of formula (I), $R^b$ is hydrogen. In some embodiments of formula (I), $R^b$ is $C_1$-$C_6$ alkyl (e.g., methyl, ethyl, isopropyl or sec-butyl). In some embodiments of formula (I), Y is S. In some embodiments of formula (I), Y is O. In some embodiments of formula (I), Y is $NR^b$. In some embodiments of formula (I), $R^b$ is hydrogen. In some embodiments of formula (I), $R^b$ is $C_1$-$C_6$ alkyl (e.g., methyl, ethyl, isopropyl or sec-butyl).

In some embodiments of formula (I), one of X and Y is O and the other is S. In some embodiments of formula (I), one of X and Y is O and the other is $NR^b$. In some embodiments of formula (I), $R^b$ is hydrogen. In some embodiments of formula (I), $R^b$ is $C_1$-$C_6$ alkyl (e.g., methyl, ethyl, isopropyl or sec-butyl). In some embodiments of formula (I), one of X and Y is S and the other is $NR^b$. In some embodiments of formula (I), $R^b$ is hydrogen. In some embodiments of formula (I), $R^b$ is $C_1$-$C_6$ alkyl (e.g., methyl, ethyl, isopropyl or sec-butyl).

In some embodiments of formula (I), Z is O.

In some embodiments, the compound of formula (I) is represented by the following formula:

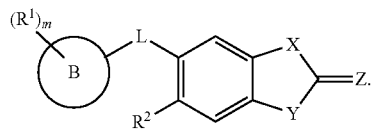

In one aspect, the invention features a compound of formula (I-II):

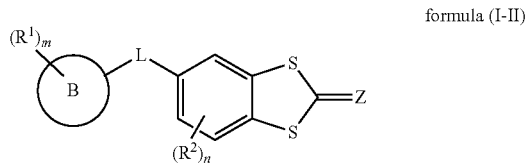

formula (I-II)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, $-NO_2$, aryl, aralkyl, heteroaryl, $-SO_2$-aryl, $-C(O)-NR^b$-aryl, $-C(O)$-aralkyl, $-C(O)-C_{1-6}$ alkoxy, $-NR^b-SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 1 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from $-SO_2-$, $-SO_2NR^a-$ and $-NR^aSO_2-$;

each $R^a$ is independently selected from hydrogen and $C_1$-$C_6$ alkyl;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

In some embodiments of formula (I-II), each $R^1$ is independently selected from $C_1$-$C_6$ alkyl, $C_1$-$C_6$ alkoxy, $C_1$-$C_6$ haloalkyl, halo, acetyl and $-NO_2$.

In some embodiments of formula (I-II), L is a linker selected from —SO₂NRᵃ— and —NRᵃSO₂—.

In some embodiments of formula (I-II), each Rᵇ is independently selected from hydrogen and $C_1$-$C_6$ alkyl.

In some embodiments of formula (I-II), B is a monocyclic heteroaryl, cycloalkyl, heterocyclyl, $C_{1-6}$ aralkyl, or $C_{1-6}$ heteroaralkyl.

In some embodiments of formula (I-II), B is a monocyclic heterocyclyl (e.g., a 6-membered monocyclic heterocyclyl). In some embodiments of formula (I-II), B is a 6-membered nitrogen containing monocyclic heterocyclyl (e.g., piperazinyl). In some embodiments of formula (I-II), B is unsubstituted piperazinyl. In some embodiments of formula (I-II), B is piperazinyl substituted with an $R^1$. In some embodiments of formula (I-II), B is a 7-membered nitrogen containing monocyclic heterocyclyl (e.g., 1,4-diazepam). In some embodiments of formula (I-II), B is unsubstituted 1,4-diazepam. In some embodiments of formula (I-II), B is 1,4-diazepam substituted with an $R^1$.

In some embodiments of formula (I-II), B is a monocyclic heteroaryl. In some embodiments of formula (I-II), B is a 5-membered monocyclic heteroaryl (e.g., thiophenyl). In some embodiments of formula (I-II), B is a 6-membered monocyclic heteroaryl, e.g., a 6-membered nitrogen-containing monocyclic heteroaryl (e.g., pyridyl). In some embodiments of formula (I-II), B is pyridyl substituted with 2 $R^1$. In some embodiments of formula (I-II), one $R^1$ is halo and the other is haloalkyl. In some embodiments of formula (I-II), one $R^1$ is chloro and the other is trifluoromethyl.

In some embodiments of formula (I-II), B is monocyclic aryl (e.g., phenyl). In some embodiments of formula (I-II), B is unsubstituted phenyl. In some embodiments of formula (I-II), B is phenyl substituted with one $R^1$. In some embodiments of formula (I-II), $R^1$ is halo (e.g., fluoro, chloro or bromo). In some embodiments of formula (I-II), $R^1$ is $C_1$-$C_6$ alkyl (e.g., methyl). In some embodiments of formula (I-II), $R^1$ is $C_1$-$C_6$ alkoxy (e.g., methoxy). In some embodiments of formula (I-II), $R^1$ is acetyl. In some embodiments of formula (I-II), $R^1$ is —NO₂.

In some embodiments of formula (I-II), B is phenyl substituted with two $R^1$. In some embodiments of formula (I-II), one $R^1$ is halo (e.g., fluoro or chloro) and the other is $C_1$-$C_6$ alkoxy (e.g., methoxy).

In some embodiments of formula (I-II), both $R^1$ are halo (e.g., fluoro or chloro). In some embodiments of formula (I-II), one $R^1$ is $C_1$-$C_6$ alkyl (e.g., methyl) and the other is $C_1$-$C_6$ alkoxy (e.g., methoxy). In some embodiments of formula (I-II), both $R^1$ are $C_1$-$C_6$ alkoxy (e.g., methoxy).

In some embodiments of formula (I-II), B is a 5-membered monocyclic heteroaryl (e.g., thiophenyl). In some embodiments of formula (I-II), B is a 6-membered monocyclic heteroaryl, e.g., a 6-membered nitrogen-containing monocyclic heteroaryl (e.g., pyridyl). In some embodiments of formula (I-II), B is pyridyl substituted with 2 $R^1$. In some embodiments of formula (I-II), one $R^1$ is halo and the other is haloalkyl. In some embodiments of formula (I-II), one $R^1$ is chloro and the other is trifluoromethyl. In some embodiments of formula (I-II), B is cycloalkyl (e.g., cyclohexyl).

In some embodiments of formula (I-II), n is 1. In some embodiments of formula (I-II), $R^2$ is $C_1$-$C_6$ alkyl (e.g., methyl). In some embodiments of formula (I-II), $R^2$ is halo (e.g., fluoro, chloro or bromo).

In some embodiments of formula (I-II), L is —SO₂—. In some embodiments of formula (I-II), L is —SO₂NRᵃ—. In some embodiments of formula (I-II), Rᵃ is hydrogen. In some embodiments of formula (I-II), Rᵃ is $C_1$-$C_6$ alkyl (e.g., methyl, ethyl or isopropyl). In some embodiments of formula (I-II), L is —NRᵃSO₂—. In some embodiments of formula (I-II), Rᵃ is hydrogen. In some embodiments of formula (I-II), Rᵃ is $C_1$-$C_6$ alkyl (e.g., methyl, ethyl or isopropyl).

In some embodiments of formula (I-II), Z is O.

In some embodiments of formula (I-II), the compound of formula (I-II) is represented by the following formula:

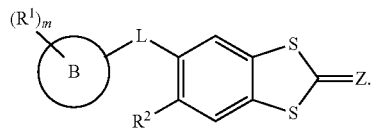

In one aspect, the invention features a compound of formula (I-III):

formula (I-III)

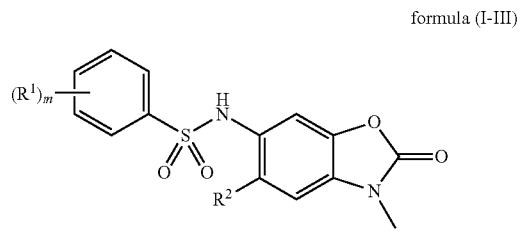

wherein:
m is an integer from 0 to 5;
each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —NO₂, aryl, aralkyl, heteroaryl, —SO₂-aryl, —C(O)—NRᵇ-aryl, —C(O)-aralkyl, —C(O)—$C_{1-6}$ alkoxy, —NRᵇ—SO₂-aryl, wherein each aryl, aralkyl and heteroaryl group is optionally substituted with 0-3 occurrences of Rᶜ and wherein two $R^1$ groups taken together with the carbon atoms to which they are attached form a heterocyclyl ring;
each $R^2$ is independently selected from $C_1$-$C_6$ alkyl and halo;
each Rᵇ is independently selected from hydrogen, $C_{1-6}$ aralkyl, and $C_1$-$C_6$ alkyl substituted with 0-1 occurrences of Rᶜ;
Rᶜ is independently selected from $C_{1-6}$ alkyl, $C_{1-6}$ alkoxy, $C_{1-6}$ haloalkyl, halo, NRᵈRᵈ, and heterocyclyl and wherein two Rᶜ groups taken together with the carbon atoms to which they are attached form a heterocyclyl ring; and
Rᵈ is independently selected from H and $C_{1-6}$ alkyl.

In some embodiments of formula (I-III), each $R^1$ is independently selected from $C_1$-$C_6$ alkyl, $C_1$-$C_6$ alkoxy, $C_1$-$C_6$ haloalkyl, halo, acetyl and —NO₂.

In some embodiments of formula (I-III), each $R^2$ is independently $C_1$-$C_6$ alkyl.

In some embodiments of formula (I-III), m is 0. In some embodiments of formula (I-III), m is 1. In some embodiments of formula (I-III), $R^1$ is halo (e.g., fluoro, chloro or bromo). In some embodiments of formula (I-III), $R^1$ is $C_1$-$C_6$ alkyl (e.g., methyl). In some embodiments of formula (I-III), $R^1$ is $C_1$-$C_6$ alkoxy (e.g., methoxy). In some embodiments of formula (I-III), $R^1$ is acetyl. In some embodiments of formula (I-III), $R^1$ is —NO₂.

In some embodiments of formula (I-III), m is 2. In some embodiments of formula (I-III), one $R^1$ is halo (e.g., fluoro or chloro) and the other is $C_1$-$C_6$ alkoxy (e.g., methoxy). In some embodiments of formula (I-III), both $R^1$ are halo (e.g., fluoro or chloro). In some embodiments of formula (I-III), one $R^1$ is $C_1$-$C_6$ alkyl (e.g., methyl) and the other is $C_1$-$C_6$ alkoxy (e.g., methoxy). In some embodiments of formula (I-III), both $R^1$ are $C_1$-$C_6$ alkoxy (e.g., methoxy). In some embodiments of formula (I-III), both $R^1$ are $C_{1-6}$ alkyl (e.g., methyl).

In some embodiments of formula (I-III), $R^2$ is methyl.

In one aspect, the invention features a pharmaceutical composition comprising a compound of formula (I-IV):

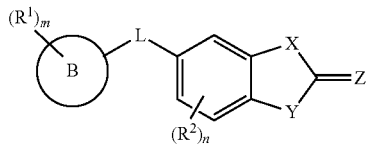

formula (I-IV)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 0 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —$SO_2$—, —$SO_2NR^a$— and —$NR^aSO_2$—;

each $R^a$ is independently selected from hydrogen and $C_1$-$C_6$ alkyl;

X and Y are each independently selected from O, S, $NR^b$ and $CH_2$;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

In some embodiments of formula (I-IV), B is monocyclic aryl (e.g., phenyl). In some embodiments of formula (I-IV), B is unsubstituted phenyl. In some embodiments of formula (I-IV), B is phenyl substituted with 1 $R^1$. In some embodiments of formula (I-IV), $R^1$ is halo (e.g., fluoro, chloro or bromo). In some embodiments of formula (I-IV), $R^1$ is $C_1$-$C_6$ alkyl (e.g., methyl or ethyl). In some embodiments of formula (I-IV), $R^1$ is $C_1$-$C_6$ alkoxy (e.g., methoxy). In some embodiments of formula (I-IV), $R^1$ is haloalkyl (e.g., trifluoromethyl). In some embodiments of formula (I-IV), $R^1$ is acetyl. In some embodiments of formula (I-IV), $R^1$ is —$NR^b$-acetyl (e.g., acetamide). In some embodiments of formula (I-IV), $R^1$ is —$NO_2$. In some embodiments of formula (I-IV), $R^1$ is —$NR^b$—$SO_2$-aryl (e.g., —$NR^b$—$SO_2$-phenyl). In some embodiments of formula (I-IV), $R^b$ is H. In some embodiments of formula (I-IV), $R^1$ is —NH—$SO_2$-phenyl substituted with two occurrences of $R^c$. In some embodiments of formula (I-IV), one $R^c$ is $C_{1-6}$ alkoxy (e.g., methoxy) and one $R^c$ is halo (e.g., fluoro or chloro). In some embodiments of formula (I-IV), both $R^c$ are halo (e.g., fluoro or chloro). In some embodiments of formula (I-IV), one $R^c$ is $C_{1-6}$ alkoxy (e.g., methoxy) and one $R^c$ is $C_{1-6}$ alkyl (e.g., methyl).

In some embodiments of formula (I-IV), B is phenyl substituted with two $R^1$. In some embodiments of formula (I-IV), one $R^1$ is halo (e.g., fluoro or chloro) and the other is $C_1$-$C_6$ alkoxy (e.g., methoxy). In some embodiments of formula (I-IV), both $R^1$ are halo (e.g., fluoro or chloro). In some embodiments of formula (I-IV), one $R^1$ is halo (e.g., fluoro or chloro) and one $R^1$ is haloalkyl (e.g., trifluoromethyl). In some embodiments of formula (I-IV), one $R^1$ is halo (e.g., fluoro or chloro) and one $R^1$ is $C_{1-6}$ alkyl (e.g., methyl or ethyl). In some embodiments of formula (I-IV), one $R^1$ is $C_1$-$C_6$ alkyl (e.g., methyl) and the other is $C_1$-$C_6$ alkoxy (e.g., methoxy). In some embodiments of formula (I-IV), both $R^1$ are $C_1$-$C_6$ alkyl (e.g., methyl). In some embodiments of formula (I-IV), both $R^1$ are $C_1$-$C_6$ alkoxy (e.g., methoxy). In some embodiments of formula (I-IV), two $R^1$ groups taken together with the carbon atoms to which they are attached form a heterocyclyl ring. In some embodiments of formula (I-IV), two $R^1$ groups taken together with the carbon atoms to which they are attached form the following compound:

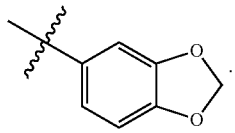 [SMILES: *c1ccc2c(c1)OCO2]

In some embodiments of formula (I-IV), two $R^1$ groups taken together with the carbon atoms to which they are attached form the following compound:

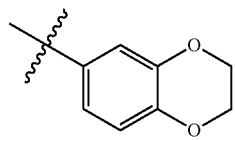 [SMILES: *c1ccc2c(c1)OCCO2]

In some embodiments of formula (I-IV), B is bicyclic aryl (e.g., naphthyl). In some embodiments of formula (I-IV), B is unsubstituted naphthyl.

In some embodiments of formula (I-IV), B is monocyclic heteroaryl, e.g., a 5-membered monocyclic heteroaryl (e.g., thiophenyl). In some embodiments of formula (I-IV), B is a 6-membered monocyclic heteroaryl, e.g., a 6-membered nitrogen-containing monocyclic heteroaryl (e.g., pyridyl). In some embodiments of formula (I-IV), B is unsubstituted pyridyl. In some embodiments of formula (I-IV), B is pyridyl substituted with two $R^1$. In some embodiments of formula (I-IV), one $R^1$ is halo (e.g., chloro) and the other is haloalkyl (e.g., trifluoromethyl).

In some embodiments of formula (I-IV), B is bicyclic heteroaryl, e.g., a 10-membered bicyclic heteroaryl (e.g., a 10-membered nitrogen containing bicyclic heteroaryl). In some embodiments of formula (I-IV), B is a 10-membered nitrogen containing bicyclic heteroaryl (e.g., quinolyl). In some embodiments of formula (I-IV), B is unsubstituted quinolyl.

In some embodiments of formula (I-IV), B is a monocyclic heterocyclyl (e.g., a 6-membered monocyclic heterocyclyl). In some embodiments of formula (I-IV), B is a 6-membered nitrogen containing monocyclic heterocyclyl (e.g., piperazinyl). In some embodiments of formula (I-IV), B is unsubstituted piperazinyl. In some embodiments of formula (I-IV), B is piperazinyl substituted with an $R^1$. In some embodiments of formula (I-IV), $R^1$ is —$SO_2$-aryl (e.g., phenyl or naphthyl). In some embodiments of formula (I-IV), $R^1$ is —$SO_2$-phenyl substituted with 0 occurrences of $R^c$. In some embodiments of formula (I-IV), $R^1$ is —$SO_2$-naphthyl. In some embodiments of formula (I-IV), $R^1$ is —$SO_2$-phenyl substituted with 1 occurrence of $R^c$. In some embodiments of formula (I-IV), $R^c$ is $C_{1-6}$ alkoxy (e.g., methoxy). In some embodiments of formula (I-IV), $R^c$ is halo (e.g., fluoro or chloro).

In some embodiments of formula (I-IV), $R^1$ is —$SO_2$-phenyl substituted with 2 occurrences of $R^c$. In some embodiments of formula (I-IV), one $R^c$ is $C_{1-6}$ alkoxy (e.g., methoxy) and the other $R^c$ is halo (e.g., chloro or fluoro). In some embodiments of formula (I-IV), both $R^c$ are halo (e.g., fluoro or chloro). In some embodiments of formula (I-IV), both $R^c$ taken together form a heterocyclyl. In some embodiments of formula (I-IV), both $R^c$ are taken together to form the compound represented below:

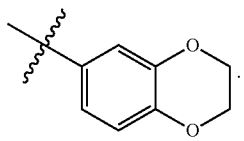 [SMILES: *c1ccc2c(c1)OCCO2]

In some embodiments of formula (I-IV), $R^1$ is aralkyl (e.g., benzyl).

In some embodiments of formula (I-IV), $R^1$ is —C(O)—$C_{1-6}$ alkoxy (e.g., —C(O)-t-butoxy).

In some embodiments of formula (I-IV), $R^1$ is —$SO_2$-heteroaryl (e.g., —$SO_2$-pyridyl). In some embodiments of formula (I-IV), $R^1$ is —$SO_2$-pyridyl substituted with 0 occurrences of $R^c$. In some embodiments of formula (I-IV), $R^1$ is —$SO_2$-pyridyl substituted with 1 occurrence of $R^c$. In some embodiments of formula (I-IV), $R^c$ is haloalkyl (e.g., trifluoromethyl).

In some embodiments of formula (I-IV), $R^1$ is —C(O)-aralkyl (e.g., —C(O)-benzyl). In some embodiments of formula (I-IV), $R^1$ is —C(O)-benzyl substituted with 0 occurrences of $R^c$. In some embodiments of formula (I-IV), $R^1$ is —C(O)-benzyl substituted with 1 occurrence of $R^c$. In some embodiments of formula (I-IV), $R^c$ is haloalkyl (e.g., trifluoromethyl).

In some embodiments of formula (I-IV), B is a monocyclic heterocyclyl (e.g., a 7-membered monocyclic heterocyclyl). In some embodiments of formula (I-IV), B is a 7-membered nitrogen containing monocyclic heterocyclyl (e.g., 1,4-diazepanyl). In some embodiments of formula (I-IV), B is unsubstituted 1,4-diazepanyl. In some embodiments of formula (I-IV), B is 1,4-diazepanyl substituted with an $R^1$. In some embodiments of formula (I-IV), $R^1$ is —$SO_2$-aryl (e.g., phenyl or naphthyl). In some embodiments of formula (I-IV), $R^1$ is —$SO_2$-phenyl substituted with 0 occurrences of $R^c$. In some embodiments of formula (I-IV), $R^1$ is —$SO_2$-naphthyl. In some embodiments of formula (I-IV), $R^1$ is —$SO_2$-phenyl substituted with 1 occurrence of $R^c$. In some embodiments of formula (I-IV), $R^c$ is $C_{1-6}$ alkoxy (e.g., methoxy). In some embodiments of formula (I-IV), $R^c$ is halo (e.g., fluoro or chloro).

In some embodiments of formula (I-IV), $R^1$ is phenyl substituted with 2 occurrences of $R^c$. In some embodiments of formula (I-IV), one $R^c$ is $C_{1-6}$ alkoxy (e.g., methoxy) and the other $R^c$ is halo (e.g., chloro or fluoro). In some embodiments of formula (I-IV), both $R^c$ are halo (e.g., fluoro or chloro). In some embodiments of formula (I-IV), both $R^c$ taken together form a heterocyclyl. In some embodiments of formula (I-IV), both $R^c$ are taken together to form the compound represented below:

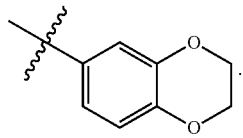 [SMILES: *c1ccc2c(c1)OCCO2]

In some embodiments of formula (I-IV), $R^1$ is aralkyl (e.g., benzyl).

In some embodiments of formula (I-IV), $R^1$ is —C(O)—$C_{1-6}$ alkoxy (e.g., —C(O)-t-butoxy).

In some embodiments of formula (I-IV), $R^1$ is —$SO_2$-heteroaryl (e.g., —$SO_2$-pyridyl). In some embodiments of formula (I-IV), $R^1$ is —$SO_2$-pyridyl substituted with 0 occurrences of $R^c$. In some embodiments of formula (I-IV), $R^1$ is —$SO_2$-pyridyl substituted with 1 occurrence of $R^c$. In some embodiments of formula (I-IV), $R^c$ is haloalkyl (e.g., trifluoromethyl).

In some embodiments of formula (I-IV), B is a monocyclic heterocyclyl (e.g., a 6-membered monocyclic heterocyclyl). In some embodiments of formula (I-IV), B is a 6-membered nitrogen containing monocyclic heterocyclyl (e.g., piperidinyl). In some embodiments of formula (I-IV), B is unsubstituted piperidinyl. In some embodiments of formula (I-IV), B is piperidinyl substituted with an $R^1$. In some embodiments of formula (I-IV), $R^1$ is —C(O)—$NR^b$-aryl (e.g., —C(O)—$NR^b$-phenyl. In some embodiments of formula (I-IV), $R^b$ is H. In some embodiments of formula (I-IV), $R^1$ is —C(O)—NH-phenyl substituted with two occurrences of $R^c$. In some embodiments of formula (I-IV), both $R^c$ are $C_{1-6}$ alkyl (e.g., methyl).

In some embodiments of formula (I-IV), B is cycloalkyl (e.g., cyclohexyl).

In some embodiments of formula (I-IV), B is $C_{1-6}$ aralkyl (e.g., benzyl). In some embodiments of formula (I-IV), B is benzyl substituted with 0 occurrences of $R^1$.

In some embodiments of formula (I-IV), n is 0. In some embodiments of formula (I-IV), n is 1. In some embodiments of formula (I-IV), $R^2$ is $C_1$-$C_6$ alkyl (e.g., methyl). In some embodiments of formula (I-IV), $R^2$ is halo (e.g., fluoro, chloro or bromo).

In some embodiments of formula (I-IV), L is —$SO_2NR^a$—. In some embodiments of formula (I-IV), $R^a$ is hydrogen. In some embodiments of formula (I-IV), $R^a$ is $C_1$-$C_6$ alkyl (e.g., methyl, ethyl or isopropyl). In some embodiments of formula (I-IV), L is —$NR^aSO_2$—. In some embodiments of formula (I-IV), $R^a$ is hydrogen. In some embodiments of formula (I-IV), $R^a$ is $C_1$-$C_6$ alkyl (e.g., methyl, ethyl or isopropyl).

In some embodiments of formula (I-IV), X is S. In some embodiments of formula (I-IV), X is O. In some embodiments of formula (I-IV), X is $NR^b$. In some embodiments of formula (I-IV), $R^b$ is hydrogen. In some embodiments of formula (I-IV), $R^b$ is $C_1$-$C_6$ alkyl substituted with 0 occurrences of $R^c$ (e.g., methyl, ethyl, isopropyl or sec-butyl). In some embodiments of formula (I-IV), $R^b$ is aralkyl (e.g., benzyl or phenethyl). In some embodiments of formula (I-IV), $R^b$ is $C_{1-6}$ alkyl substituted with 1 occurrence of $R^c$ (e.g., methyl, ethyl or propyl). In some embodiments of formula (I-IV), $R^c$ is $C_{1-6}$ alkoxy (e.g., methoxy). In some embodiments of formula (I-IV), $R^c$ is heterocyclyl (e.g., morpholinyl or piperidinyl). In some embodiments of formula (I-IV), $R^c$ is $NR^dR^d$. In some embodiments of formula (I-IV), $R^d$ is selected from $C_{1-6}$ alkyl (e.g., methyl).

In some embodiments of formula (I-IV), Y is S. In some embodiments of formula (I-IV), Y is O. In some embodiments of formula (I-IV), Y is $NR^b$. In some embodiments of formula (I-IV), $R^b$ is hydrogen. In some embodiments of formula (I-IV), $R^b$ is $C_1$-$C_6$ alkyl substituted with 0 occurrences of $R^c$ (e.g., methyl, ethyl, isopropyl or sec-butyl). In some embodiments of formula (I-IV), $R^b$ is aralkyl (e.g., benzyl or phenethyl). In some embodiments of formula (I-IV), $R^b$ is $C_{1-6}$ alkyl substituted with 1 occurrence of $R^c$ (e.g., methyl, ethyl or propyl). In some embodiments of formula (I-IV), $R^c$ is $C_{1-6}$ alkoxy (e.g., methoxy). In some embodiments of formula (I-IV), $R^c$ is heterocyclyl (e.g., morpholinyl or piperidinyl). In some embodiments of formula (I-IV), $R^c$ is $NR^dR^d$. In some embodiments of formula (I-IV), $R^d$ is selected from $C_{1-6}$ alkyl (e.g., methyl).

In some embodiments of formula (I-IV), X and Y are both S. In some embodiments of formula (I-IV), X and Y are both $NR^b$. In some embodiments of formula (I-IV), X and Y are both $NCH_3$. In some embodiments of formula (I-IV), one of X and Y is O and the other is S. In some embodiments of formula (I-IV), one of X and Y is O and the other is $NR^b$. In some embodiments of formula (I-IV), $R^b$ is hydrogen. In some embodiments of formula (I-IV), $R^b$ is $C_1$-$C_6$ alkyl (e.g., methyl, ethyl, isopropyl or sec-butyl).

In some embodiments of formula (I-IV), one of X and Y is S and the other is $NR^b$. In some embodiments of formula (I-IV), $R^b$ is hydrogen. In some embodiments of formula (I-IV), $R^b$ is $C_1$-$C_6$ alkyl (e.g., methyl, ethyl, isopropyl or sec-butyl).

In some embodiments of formula (I-IV), Z is O.

In one aspect, the present invention features a compound or pharmaceutically acceptable salt thereof of formula (II):

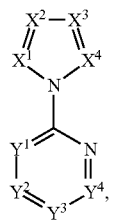

(II)

wherein
$X^1$ is N or CE;
$X^2$ is N or CD;
$X^3$ is N or CB;
$X^4$ is N or CA;
$Y^1$, $Y^2$, $Y^3$ and $Y^4$ are each independently selected from N and $CR^1$;
A, B, D and E are each independently selected from H, $R^3$ and $-SO_2-NR^4R^5$;
wherein at least one of $X^1$, $X^2$, $X^3$, $X^4$, $Y^1$, $Y^2$, $Y^3$ and $Y^4$ is N; and at least one of $X^1$, $X^2$, $X^3$, $X^4$, is C$-SO_2-NR^4R^5$;
each $R^4$ is independently selected from $C_{1-8}$ alkyl, aryl and heteroaryl, each of which is substituted with n occurrences of $R^2$;
each $R^5$ is independently hydrogen or $C_{1-8}$ alkyl;
each $R^1$ is independently selected from hydrogen, $C_{1-8}$ alkyl, $C_{1-8}$ terminal alkynyl, $C_{1-8}$ alkoxy, halogen, haloalkyl and haloalkoxy;

each $R^2$ is independently selected from halo, haloalkyl, $C_{1-4}$ alkyl, $C_{2-4}$ alkenyl, $C_{2-4}$ alknynyl, aryl, heteroaryl, aralkyl, heteroaralkyl, cyano, $-OR^a$, $-COOR^b$ and $-CONR^cR^{c'}$; wherein two $R^2$, together with the carbons to which they are attached, may form an optionally substituted ring, each of which can be further substituted;
each $R^3$ is independently selected from $C_{1-8}$ alkyl, $-OR^a$, halogen, haloalkyl, haloalkoxy and optionally substituted heteroaryl;
each $R^a$ is independently selected from alkyl, haloalkyl, optionally substituted heteroaryl and optionally substituted heterocyclyl;
each $R^b$ is independently alkyl; and
each $R^c$ is independently selected from hydrogen and alkyl; and
n is 0, 1, 2 or 3.

In some embodiments of formula (II), one of $X^1$, $X^2$, $X^3$, $X^4$, is C$-SO_2-NR^4R^5$;

In some embodiments of formula (II), $X^4$ is A and A is $-SO_2-NR^4R^5$. In some embodiments of formula (II), $X^3$ is B and B is $-SO_2-NR^4R^5$. In some embodiments of formula (II), $X^2$ is D and D is $-SO_2-NR^4R^5$. In some embodiments of formula (II), $X^1$ is CE and E is $-SO_2-NR^4R^5$.

In some embodiments of formula (II), the compound is a compound of formula (IIa):

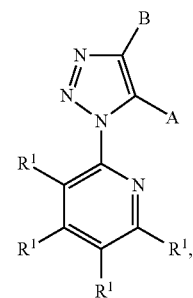

(IIa)

wherein A, B, D, $R^1$, $R^2$, $R^3$, $R^4$, $R^5$ and n are as defined in formula (II).

In some embodiments of formula (IIa), A or B is $-SO_2-NR^4R^5$.

In some embodiments of formula (II), the compound is a compound of formula (IIb):

(IIb)

wherein A, B, $R^1$, $R^2$, $R^3$, $R^4$, $R^5$ and n are as defined in formula (II).

In some embodiments of formula (IIb), A or B is $-SO_2-NR^4R^5$.

In some embodiments of formula (II), the compound is a compound of formula (IIc):

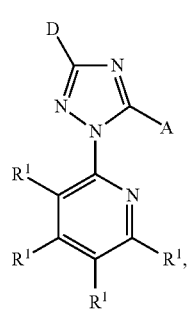

(IIc)

wherein A, D, $R^1$, $R^2$, $R^3$, $R^4$, $R^5$ and n are as defined in formula (II).

In some embodiments of formula (IIc), A or D is $-SO_2-NR^4R^5$.

In some embodiments of formula (II), the compound is a compound of formula (IId):

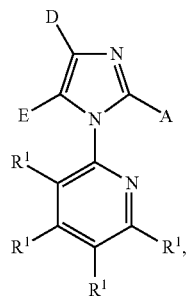

(IId)

wherein A, D, E, $R^1$, $R^2$, $R^3$, $R^4$, $R^5$ and n are as defined in formula (II).

In some embodiments of formula (IId), A is $-SO_2-NR^4R^5$.

In some embodiments of formula (II), the compound is a compound of formula (IIe):

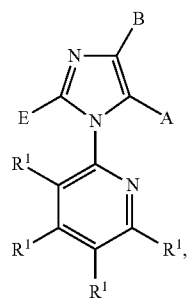

(IIe)

wherein A, B, E, $R^1$, $R^2$, $R^3$, $R^4$, $R^5$ and n are as defined in formula (II).

In some embodiments of formula (IIe), A or B is $-SO_2-NR^4R^5$.

In some embodiments of formula (II), the compound is a compound of formula (IIf):

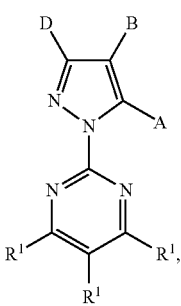

(IIf)

wherein A, B, D, $R^1$, $R^2$, $R^3$, $R^4$, $R^5$ and n are as defined in formula (II).

In some embodiments of formula (II), A or B is $-SO_2-NR^4R^5$.

In some embodiments of formula (II), the compound is a compound of formula (IIg):

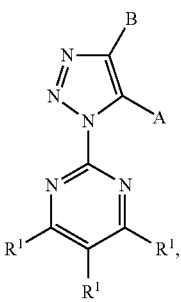

(IIg)

wherein A, B, $R^1$, $R^2$, $R^3$, $R^4$, $R^5$ and n are as defined in formula (II).

In some embodiments of formula (IIg), A is $-SO_2-NR^4R^5$.

In some embodiments of formula (IIg), B is $-SO_2-NR^4R^5$.

In some embodiments of formula (II), the compound is a compound of formula (IIh):

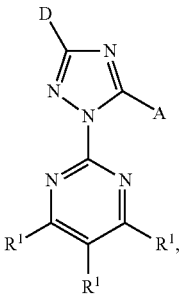

(IIh)

wherein A, D, $R^1$, $R^2$, $R^3$, $R^4$, $R^5$ and n are as defined in formula (II).

In some embodiments of formula (IIh), A is $-SO_2-NR^4R^5$.

In some embodiments of formula (II), the compound is a compound of formula (IIj):

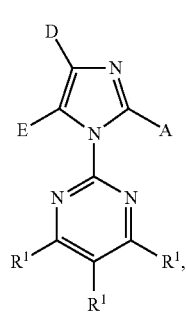
(IIj)

wherein A, D, E, R$^1$, R$^2$, R$^3$, R$^4$, R$^5$ and n are as defined in formula (II).

In some embodiments of formula (IIj), A is —SO$_2$—NR$^4$R$^5$.

In some embodiments of formula (II), the compound is a compound of formula (IIk):

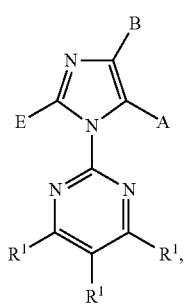
(IIk)

wherein A, B, E, R$^1$, R$^2$, R$^3$, R$^4$, R$^5$ and n are as defined in formula (II).

In some embodiments of formula (IIk), A or B is —SO$_2$—NR$^4$R$^5$.

In some embodiments, the compound is a compound of formula (IIm):

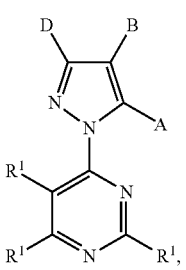
(IIm)

wherein A, B, D, R$^1$, R$^2$, R$^3$, R$^4$, R$^5$ and n are as defined in formula (II).

In some embodiments of formula (IIm), A or B is —SO$_2$—NR$^4$R$^5$.

In some embodiments of formula (II), the compound is a compound of formula (IIn):

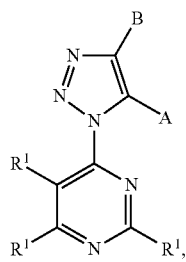
(IIn)

wherein A, B, R$^1$, R$^2$, R$^3$, R$^4$, R$^5$, and n are as defined in formula (II).

In some embodiments of formula (IIn), A is —SO$_2$—NR$^4$R$^5$.

In some embodiments of formula (IIn), B is —SO$_2$—NR$^4$R$^5$.

In some embodiments of formula (II), the compound is a compound of formula (IIo):

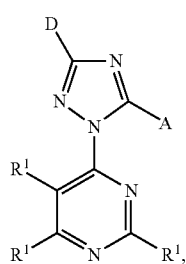
(IIo)

wherein A, D, R$^1$, R$^2$, R$^3$, R$^4$, and n are as defined in formula (II).

In some embodiments of formula (IIo), A is —SO$_2$—NR$^4$R$^5$.

In some embodiments of formula (II), the compound is a compound of formula (IIp):

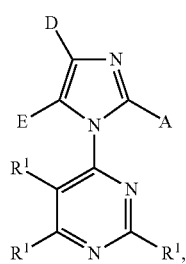
(IIp)

wherein A, D, E, R$^1$, R$^2$, R$^3$, R$^4$, R$^5$ and n are as defined in formula (II).

In some embodiments of formula (IIp), A is —SO$_2$—NR$^4$R$^5$.

In some embodiments of formula (II), the compound is a compound of formula (IIq):

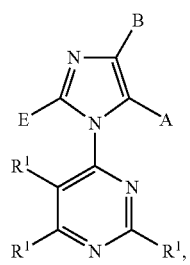

(IIq)

wherein A, B, E, $R^1$, $R^2$, $R^3$, $R^4$, $R^5$ and n are as defined in formula (II).

In some embodiments of formula (IIq), A or B is —$SO_2$—$NR^4R^5$.

In some embodiments of formula (II), the compound is a compound of formula (IIr):

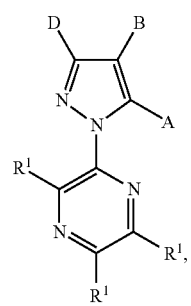

(IIr)

wherein A, B, D, $R^1$, $R^2$, $R^3$, $R^4$, $R^5$ and n are as defined in formula (II).

In some embodiments of formula (IIr), A or B is —$SO_2$—$NR^4R^5$.

In some embodiments of formula (II), the compound is a compound of formula (IIs):

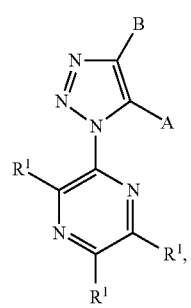

(IIs)

wherein A, B, D, E, $R^1$, $R^2$, $R^3$, $R^4$, $R^5$, m and n are as defined in formula (II).

In some embodiments of formula (IIs), A is —$SO_2$—$NR^4R^5$.

In some embodiments of formula (IIs), B is —$SO_2$—$NR^4R^5$.

In some embodiments of formula (II), the compound is a compound of formula (IIt):

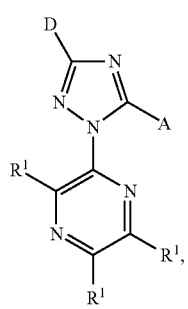

(IIt)

wherein A, D, $R^1$, $R^2$, $R^3$, $R^4$, $R^5$ and n are as defined in formula (II).

In some embodiments of formula (IIt), A is —$SO_2$—$NR^4R^5$.

In some embodiments of formula (II), the compound is a compound of formula (IIu):

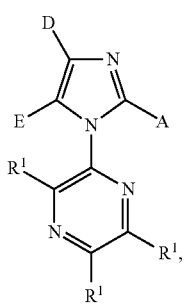

(IIu)

wherein A, D, E, $R^1$, $R^2$, $R^3$, $R^4$, $R^5$ and n are as defined in formula (II).

In some embodiments of formula (IIu), A is —$SO_2$—$NR^4R^5$.

In some embodiments of formula (II), the compound is a compound of formula (IIv):

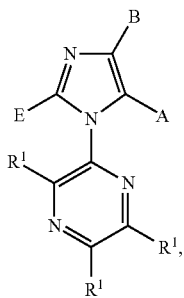

(IIv)

wherein A, B, E, $R^1$, $R^2$, $R^3$, $R^4$, $R^5$ and n are as defined in formula (II).

In some embodiments of formula (IIv), A or B is —$SO_2$—$NR^4R^5$.

In some embodiments of formula (II), the compound is a compound of formula (IIw):

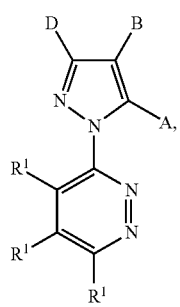

(IIw)

wherein A, B, D, $R^1$, $R^2$, $R^3$, $R^4$, $R^5$ and n are as defined in formula (II).

In some embodiments of formula (IIw), A or B is —$SO_2$—$NR^4R^5$.

In some embodiments of formula (II), the compound is a compound of formula (IIx):

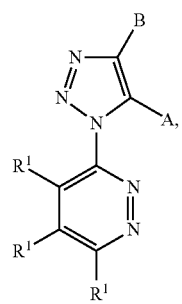

(IIx)

wherein A, B, $R^1$, $R^2$, $R^3$, $R^4$, $R^5$ and n are as defined in formula (II).

In some embodiments of formula (IIx), A is —$SO_2$—$NR^4R^5$.

In some embodiments of formula (IIx), B is —$SO_2$—$NR^4R^5$.

In some embodiments of formula (II), the compound is a compound of formula (IIy):

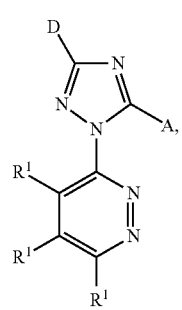

(IIy)

wherein A, D, $R^1$, $R^2$, $R^3$, $R^4$, $R^5$ and n are as defined in formula (II).

In some embodiments of formula (IIy), A is —$SO_2$—$NR^4R^5$.

In some embodiments of formula (II), the compound is a compound of formula (IIz):

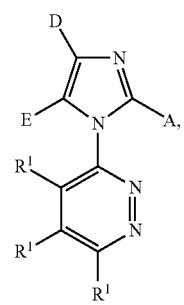

(IIz)

wherein A, D, E, $R^1$, $R^2$, $R^3$, $R^4$, $R^5$ and n are as defined in formula (II).

In some embodiments of formula (IIz), A is —$SO_2$—$NR^4R^5$.

In some embodiments of formula (II), the compound is a compound of formula (IIaa):

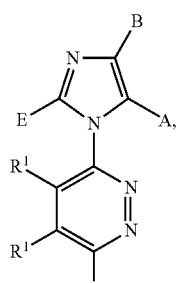

(IIaa)

wherein A, B, E, $R^1$, $R^2$, $R^3$, $R^4$, $R^5$ and n are as defined in formula (II).

In some embodiments of formula (IIaa), A is —$SO_2$—$NR^4R^5$.

In some embodiments of formula (IIaa), B is —$SO_2$—$NR^4R^5$.

In some embodiments of formula (II), the compound is a compound of formula (IIbb):

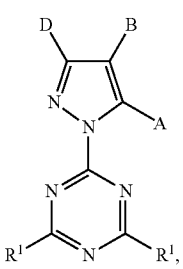

(IIbb)

wherein A, B, D, $R^1$, $R^2$, $R^3$, $R^4$, $R^5$, and n are as defined in formula (II).

In some embodiments of formula (IIbb), A is —$SO_2$—$NR^4R^5$.

In some embodiments of formula (IIbb), B is —SO$_2$—NR$^4$R$^5$.

In some embodiments of formula (II), the compound is a compound of formula (IIcc)

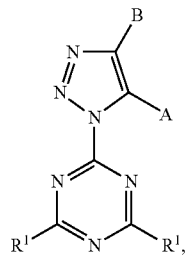
(IIcc)

wherein A, B, R$^1$, R$^2$, R$^3$, R$^4$, R$^5$, and n are as defined in formula (II).

In some embodiments of formula (IIcc), A is —SO$_2$—NR$^4$R$^5$.

In some embodiments of formula (IIcc), B is —SO$_2$—NR$^4$R$^5$.

In some embodiments of formula (II), the compound is a compound of formula (IIdd):

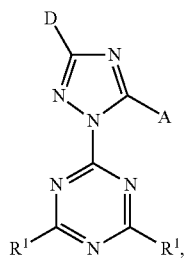
(IIdd)

wherein A, D, R$^1$, R$^2$, R$^3$, R$^4$, R$^5$ and n are as defined in formula (II).

In some embodiments of formula (IIdd), A is —SO$_2$—NR$^4$R$^5$.

In some embodiments of formula (II), the compound is a compound of formula (IIee):

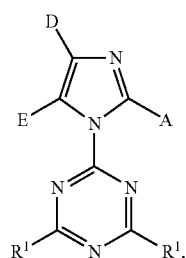
(IIee)

wherein A, D, E, R$^1$, R$^2$, R$^3$, R$^4$, R$^5$ and n are as defined in formula (II).

In some embodiments of formula (IIee), A is —SO$_2$—NR$^4$R$^5$.

In some embodiments of formula (II), the compound is a compound of formula (IIff):

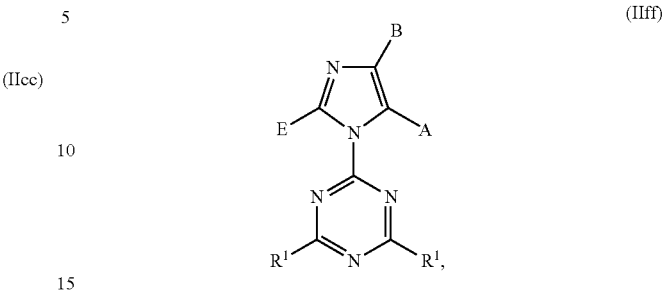
(IIff)

wherein A, B, E, R$^1$, R$^2$, R$^3$, R$^4$, R$^5$ and n are as defined in formula (II).

In some embodiments of formula (IIff), A is —SO$_2$—NR$^4$R$^5$.

In some embodiments of formula (IIff), B is —SO$_2$—NR$^4$R$^5$.

In one aspect, the present invention features a compound or pharmaceutically acceptable salt thereof of formula (II-II):

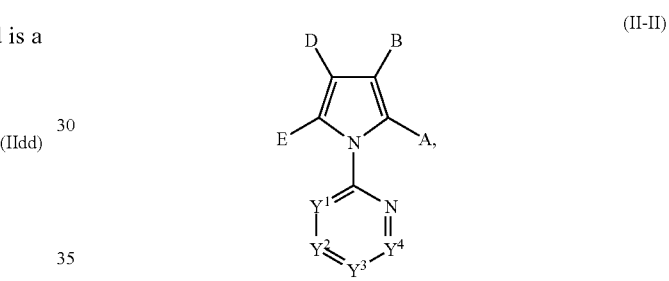
(II-II)

wherein

A, B, D and E are each independently selected from H, —SO$_2$—NR$^4$R$^5$ and R$^3$; wherein at least one of A, B, D, or E is —SO$_2$—NR$^4$R$^5$;

Y$^1$, Y$^2$, Y$^3$ and Y$^4$ are each independently selected from N and CR$^1$, wherein at least one of Y$^1$, Y$^2$, Y$^3$ and Y$^4$ are N;

each R$^4$ is independently selected from C$_{1-8}$ alkyl, aryl and heteroaryl, each of which is substituted with n occurrences of R$^2$;

each R$^5$ is independently hydrogen or C$_{1-8}$ alkyl;

each R$^1$ is independently selected from hydrogen, C$_{1-8}$ alkyl, C$_{1-8}$ terminal alkynyl, C$_{1-8}$ alkoxy, halogen, haloalkyl and haloalkoxy;

each R$^2$ is independently selected from halo, haloalkyl, C$_{1-4}$ alkyl, C$_{2-4}$ alkenyl, C$_{2-4}$ alknynyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;

each R$^3$ is independently selected from C$_{1-8}$ alkyl, —OR$^a$, halogen, haloalkyl, haloalkoxy and optionally substituted heteroaryl;

each R$^a$ is independently selected from alkyl, haloalkyl, optionally substituted heteroaryl and optionally substituted heterocyclyl;

each R$^b$ is independently alkyl; and each R$^c$ is independently selected from hydrogen and alkyl; and n is 0, 1, 2 or 3.

In some embodiments of formula (II-II), at least one of Y$^1$, Y$^2$, Y$^3$ and Y$^4$ is N. In some embodiments of formula (II-II), at least one of $Y^1, Y^2, Y^3$ and $Y^4$ are CH. In some embodiments of formula (II-II), $Y^1$ is N. In some embodiments of formula (II-II), $Y^3$ is N.

In some embodiments of formula (II-II), each $R^1$ is independently hydrogen.

In some embodiments of formula (II-II), the invention features a compound of formula (II-IIa):

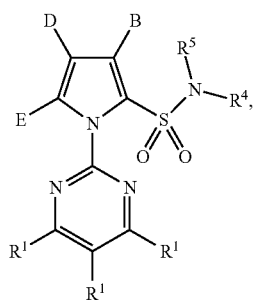

(II-IIa)

wherein n, B, D, E, $R^1, R^2, R^3, R^4$ and $R^5$ are defined as above.

In some embodiments of formula (II-II), the invention features a compound of formula (II-IIb):

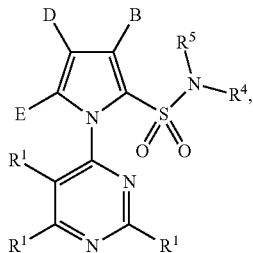

(II-IIb)

wherein n, B, D, E, $R^1, R^2, R^3, R^4$ and $R^5$ are defined as above.

In some embodiments of formula (II-II), B, D and E are each independently selected from H.

In some embodiments of formula (II-II), $R^5$ is hydrogen.

In some embodiments of formula (II-II), each $R^1$ is independently hydrogen. In some embodiments of formula (II-II), each $R^1$ is independently selected from $C_{1-8}$ alkyl, halogen or haloalkyl. In some embodiments of formula (II-II), each $R^1$ is independently selected from halogen or haloalkyl. In some embodiments of formula (II-II), each $R^1$ is independently selected from halogen (e.g., chlorine or fluorine). In some embodiments of formula (II-II), each $R^1$ is independently haloalkyl (e.g., trifluoroalkyl).

In some embodiments of formula (II-II), $R^4$ is selected from aryl or heteroaryl. In some embodiments of formula (II-II), $R^4$ is aryl substituted with n occurrences of $R^2$. In some embodiments of formula (II-II), $R^4$ is $C_{5-8}$ monocyclic aryl or $C_{8-14}$ bicyclic aryl. In some embodiments of formula (II-II), $R^4$ is $C_{5-8}$ monocyclic aryl (e.g., optionally substituted phenyl). In some embodiments of formula (II-II), $R^4$ is phenyl substituted with n occurrences of $R^2$.

In some embodiments of formula (II-II), n is 0. In some embodiments of formula (II-II), n is 1.

In some embodiments of formula (II-II), $R^2$ is halo, $C_{1-4}$ alkyl or haloalkyl, each of which can be further substituted.

In some embodiments of formula (II-II), $R^2$ is $C_{1-4}$ alkyl (e.g., ethyl). In some embodiments of formula (II-II), $R^2$ is halo (e.g., chloro). In some embodiments of formula (II-II), $R^2$ is haloalkyl (e.g., trifluoromethyl).

In some embodiments of formula (II-II), n is 2. In some embodiments of formula (II-II), both $R^2$ are $C_{1-4}$ alkyl (e.g., methyl). In some embodiments of formula (II-II), n is 2. In some embodiments of formula (II-II), both $R^2$ are halo (e.g., fluoro or chloro). In some embodiments of formula (II-II), n is 2. In some embodiments of formula (II-II), one $R^2$ is haloalkyl (e.g., trifluoroalkyl) and the other $R^2$ is —$OR^a$. In some embodiments of formula (II-II), $R^a$ is alkyl (e.g., methyl or ethyl). In some embodiments of formula (II-II), n is 2. In some embodiments of formula (II-II), one $R^2$ is halo (e.g., fluoro or chloro) and the other $R^2$ is $C_{1-4}$ alkyl (e.g., methyl or ethyl).

In some embodiments of formula (II-II), n is 2. In some embodiments of formula (II-II), two $R^2$, together with the carbon atoms to which they are attached, form a 5-membered heterocyclic ring. In some embodiments of formula (II-II), two $R^2$, together with the phenyl ring to which they are attached, form the following structure:

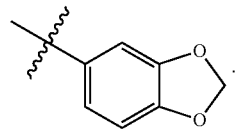 [SMILES: *c1ccc2c(c1)OCO2]

In some embodiments of formula (II-II), n is 3. In some embodiments of formula (II-II), all $R^2$ are halo (e.g., fluoro or chloro).

In one aspect, the present invention features a compound or pharmaceutically acceptable salt thereof of formula (II-III):

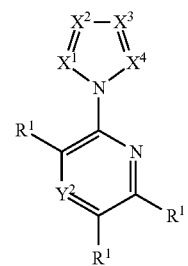

(II-III)

wherein
  $X^1$ is N or CE;
  $X^2$ is N or CD;
  $X^3$ is N or CB;
  $X^4$ is N or CA, wherein at least one of $X^1, X^2, X^3$ and $X^4$ is N and at least one of $X^1, X^2, X^3, X^4$, is C—$SO_2$—$NR^4R^5$;
  A, B, D and E are each independently selected from H, $R^3$ and —$SO_2$—$NR^4R^5$;
  $Y^2$ is selected from N and $CR^1$;
  each $R^4$ is independently selected from $C_{1-8}$ alkyl, aryl and heteroaryl, each of which is substituted with n occurrences of $R^2$;
  $R^5$ is hydrogen or $C_{1-8}$ alkyl;
  each $R^1$ is independently selected from hydrogen, $C_{1-8}$ alkyl, $C_{1-8}$ terminal alkynyl, $C_{1-8}$ alkoxy, halogen, haloalkyl and haloalkoxy;
  each $R^2$ is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;

each R$^3$ is independently selected from C$_{1-8}$ alkyl, —OR$^a$, halogen, haloalkyl, haloalkoxy and optionally substituted heteroaryl;

each R$^a$ is independently selected from alkyl, haloalkyl, optionally substituted heteroaryl and optionally substituted heterocyclyl;

each R$^b$ is independently alkyl; and each R$^c$ is independently selected from hydrogen and alkyl; and n is 0, 1, 2 or 3.

In some embodiments of formula (II-III), the invention features a compound of formula (II-IIIa):

(II-IIIa)

wherein n, B, D, E, R$^1$, R$^4$, R$^2$ and R$^5$ are defined as in formula (II-III).

In some embodiments of formula (II-III), the invention features a compound of formula (II-IIIb):

(II-IIIb)

wherein n, B, E, R$^1$, R$^4$, R$^2$ and R$^5$ are defined as in formula (II-III).

In some embodiments of formula (II-III), the invention features a compound of formula (II-IIIc):

(II-IIIc)

wherein n, B, D, R$^1$, R$^4$, R$^2$ and R$^5$ are defined as in formula (II-III).

In some embodiments of formula (II-III), B and E are each independently selected from H.

In some embodiments of formula (II-III), R$^5$ is hydrogen.

In some embodiments of formula (II-III), each R$^1$ is independently hydrogen. In some embodiments of formula (II-III), each R$^1$ is independently selected from C$_{1-8}$ alkyl, halogen or haloalkyl. In some embodiments of formula (II-III), each R$^1$ is independently selected from halogen or haloalkyl. In some embodiments of formula (II-III), each R$^1$ is independently selected from halogen (e.g., chlorine or fluorine). In some embodiments of formula (II-III), each R$^1$ is independently haloalkyl (e.g., trifluoroalkyl).

In some embodiments of formula (II-III), R$^4$ is selected from aryl or heteroaryl. In some embodiments of formula (II-III), R$^4$ is aryl substituted with n occurrences of R$^2$. In some embodiments of formula (II-III), R$^4$ is C$_{5-8}$ monocyclic aryl or C$_{8-14}$ bicyclic aryl. In some embodiments of formula (II-III), R$^4$ is C$_{5-8}$ monocyclic aryl (e.g., optionally substituted phenyl). In some embodiments of formula (II-III), R$^4$ is phenyl substituted with n occurrences of R$^2$.

In some embodiments of formula (II-III), n is 0. In some embodiments of formula (II-III), n is 1.

In some embodiments of formula (II-III), R$^2$ is halo, C$_{1-4}$ alkyl or haloalkyl, each of which can be further substituted.

In some embodiments of formula (II-III), R$^2$ is C$_{1-4}$ alkyl (e.g., methyl or ethyl).

In some embodiments of formula (II-III), R$^2$ is halo (e.g., chloro).

In some embodiments of formula (II-III), n is 2. In some embodiments of formula (II-III), both R$^2$ are C$_{1-4}$ alkyl (e.g., methyl or ethyl). In some embodiments of formula (II-III), n is 2. In some embodiments of formula (II-III), both R$^2$ are halo (e.g., fluoro or chloro). In some embodiments of formula (II-III), n is 2. In some embodiments of formula (II-III), one R$^2$ is haloalkyl (e.g., trifluoroalkyl) and the other R$^2$ is —OR$^a$. In some embodiments of formula (II-III), R$^a$ is alkyl (e.g., methyl or ethyl). In some embodiments of formula (II-III), n is 2. In some embodiments of formula (II-III), one R$^2$ is C$_{1-4}$ alkyl (e.g., methyl or ethyl) and the other R$^2$ is halo (e.g., fluoro or chloro).

In some embodiments of formula (II-III), n is 2. In some embodiments of formula (II-III), two R$^2$, together with the carbon atoms to which they are attached, form a 5-membered heterocyclic ring. In some embodiments, two R$^2$, together with the phenyl ring to which they are attached, form the following structure:

In some embodiments of formula (II-III), n is 3. In some embodiments of formula (II-III), all R$^2$ are halo (e.g., fluoro or chloro).

In another aspect, the invention features a compound or pharmaceutically acceptable salt thereof selected from the following formula:

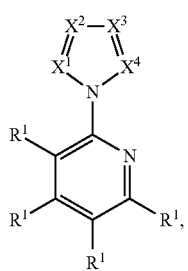

(II-IV)

wherein
n is 0, 1, 2 or 3;
X¹ is N or CE;
X² is N or CD;
X³ is N or CB;
X⁴ is N or CA, wherein at least one of X¹, X², X³ and X⁴ is N; and at least one of X¹, X², X³, X⁴, is C—SO₂—NR⁴R⁵;
A, B, D and E are each independently selected from H and —SO₂—NR⁴R⁵;
each R⁴ is independently selected from $C_{1-8}$ alkyl, aryl and heteroaryl, each of which is substituted with n occurrences of R²;
each R⁵ is independently hydrogen or $C_{1-8}$ alkyl;
each R¹ is independently selected from hydrogen, $C_{1-8}$ alkyl, $C_{1-8}$ alkoxy, halogen, haloalkyl and haloalkoxy;
each R² is independently selected from halo, haloalkyl, $C_{1-4}$alkyl, $C_{2-4}$ alkenyl, $C_{2-4}$ alkynyl heteroaryl, aryl, aralkyl, heteroaralkyl, cyano, —OR$^a$, —COOR$^b$ and —CONR$^c$R$^{c'}$; wherein two R², together with the carbons to which they are attached, may form an optionally substituted ring, each of which can be further substituted;
each R³ is independently selected from $C_{1-8}$ alkyl, —OR$^a$, halogen, haloalkyl, haloalkoxy or optionally substituted heteroaryl;
R$^a$ is independently selected from alkyl, haloalkyl, optionally substituted heteroaryl and optionally substituted heterocyclyl;
each R$^b$ is independently alkyl; and
each R$^c$ is independently selected from hydrogen and alkyl.
In some embodiments of formula (II-IV), at least one of X³ and X⁴ are CH.
In some embodiments of formula (II-IV), at least one of A, B, D and E are H. In some embodiments of formula (II-IV), at least one of A, B, D and E are —SO₂—NH—R⁴. In some embodiments of formula (II-IV), A is —SO₂—NH—R⁴. In some embodiments of formula (II-IV), B is —SO₂—NH—R⁴.
In some embodiments of formula (II-IV), the invention features a compound of formula (II-IVa):

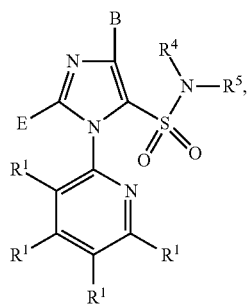

(II-IVa)

wherein n, B, E, R¹, R⁴, R³, R² and R⁵ are defined as above.

In some embodiments of formula (II-IV), the invention features a compound of formula (II-IVb):

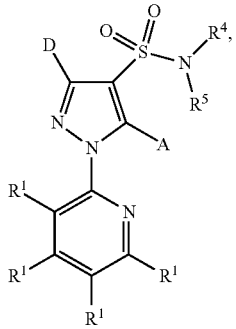

(II-IVb)

wherein n, A, D, E, R¹, R⁴, R³, R², and R⁵ are defined as above.

In some embodiments of formula (II-IV), A, and D are H. In some embodiments of formula (II-IV), B and E are H.
In some embodiments of formula (II-IV), R⁵ is hydrogen.
In some embodiments of formula (II-IV), each R¹ is independently H. In some embodiments of formula (II-IV), each R¹ is independently selected from $C_{1-8}$ alkyl, halogen or haloalkyl. In some embodiments of formula (II-IV), each R¹ is independently selected from halogen or haloalkyl. In some embodiments of formula (II-IV), each R¹ is independently selected from halogen (e.g., chlorine or fluorine). In some embodiments of formula (II-IV), each R¹ is independently haloalkyl (e.g., trifluoroalkyl).
In some embodiments of formula (II-IV), R⁴ is selected from aryl or heteroaryl. In some embodiments of formula (II-IV), R⁴ is aryl substituted with n occurrences of R². In some embodiments of formula (II-IV), R⁴ is $C_{5-8}$ monocyclic aryl or $C_{8-14}$ bicyclic aryl. In some embodiments of formula (II-IV), R⁴ is $C_{5-8}$ monocyclic aryl (e.g., phenyl). In some embodiments of formula (II-IV), R⁴ is phenyl substituted with n occurrences of R². In some embodiments of formula (II-IV), R⁴ is $C_{8-14}$ bicyclic aryl (e.g., napthyl). In some embodiments of formula (II-IV), R⁴ is a 5-8 membered heteroaryl or a 8-14 membered heteroaryl. In some embodiments of formula (II-IV), R⁴ is a 8-14 membered heteroaryl (e.g., 5-quinolyl or 6-quinolyl). In some embodiments of formula (II-IV), R⁴ is quinolyl (e.g., 5-quinolyl or 6-quinolyl) substituted with n occurrences of R².

In some embodiments of formula (II-IV), n is 0. In some embodiments of formula (II-IV), n is 1.
In some embodiments of formula (II-IV), R² is selected from halo, $C_{1-4}$ alkyl, cyano, haloalkyl, —OR$^a$ or two R², taken together with the carbon atoms to which they are attached form an optionally substituted ring, each of which can be further substituted.
In some embodiments of formula (II-IV), R² is halo (e.g., chloro or fluoro). In some embodiments of formula (II-IV), R² is $C_{1-4}$ alkyl (e.g., methyl or ethyl). In some embodiments of formula (II-IV), R² is cyano. In some embodiments of formula (II-IV), R² is haloalkyl (e.g., trifluoromethyl). In some embodiments of formula (II-IV), R² is —OR$^a$. In some embodiments of formula (II-IV), R$^a$ is alkyl (e.g., methyl).

In some embodiments of formula (II-IV), n is 2. In some embodiments of formula (II-IV), both $R^2$ are $C_{1-4}$ alkyl (e.g., methyl). In some embodiments of formula (II-IV), n is 2. In some embodiments of formula (II-IV), both $R^2$ are halo (e.g., fluoro or chloro). In some embodiments of formula (II-IV), n is 2. In some embodiments of formula (II-IV), one $R^2$ is $C_{1-4}$ alkyl and the other is halo (e.g., methyl and chloro or methyl and fluoro). In some embodiments of formula (II-IV), n is 2. In some embodiments of formula (II-IV), both $R^2$ are haloalkyl (e.g., trifluoromethyl). In some embodiments of formula (II-IV), n is 2. In some embodiments of formula (II-IV), both $R^2$ are —$OR^a$. In some embodiments of formula (II-IV), both $R^a$ are alkyl (e.g, methyl). In some embodiments of formula (II-IV), n is 2. In some embodiments of formula (II-IV), one $R^2$ is haloalkyl (e.g., trifluoromethyl) and one is —$OR^a$. In some embodiments of formula (II-IV), $R^a$ is alkyl (e.g., methyl).

In some embodiments of formula (II-IV), n is 2. In some embodiments of formula (II-IV), two $R^2$, taken together with the carbon atoms to which they are attached, form a 6-membered heterocyclic ring. In some embodiments of formula (II-IV), two $R^2$, taken together with the phenyl ring to which they are attached, for the following structure:

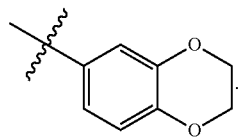 [SMILES: *c1ccc2c(c1)OCCO2]

In some embodiments of formula (II-IV), n is 3. In some embodiments of formula (II-IV), three $R^2$ are halo (e.g., fluoro).

In another aspect, the invention features a pharmaceutical composition comprising a compound of formula (II-V):

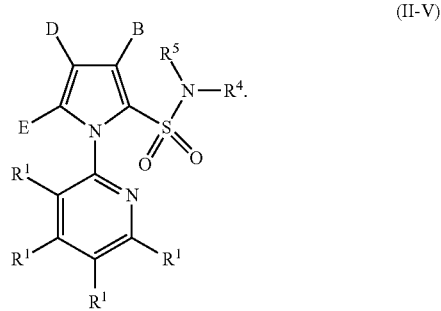

wherein
B, D and E are each independently selected from H and $R^3$;
each $R^1$ is independently selected from hydrogen, halo and haloalkyl;
$R^4$ is hydrogen, $C_{1-8}$ alkyl, and aryl, substituted with n occurrences of $R^2$;
each $R^2$ is independently selected from halo, haloalkyl, alkyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;
each $R^3$ is independently selected from halo, haloalkyl and —$OR^a$;
$R^5$ is hydrogen or $C_{1-8}$ alkyl;

$R^a$ is independently selected from alkyl, haloalkyl, optionally substituted heteroaryl and optionally substituted heterocyclyl;
each $R^b$ is independently alkyl;
each $R^c$ is independently selected from hydrogen and alkyl; and
n is 0, 1, 2, or 3.

In some embodiments of formula (II-V), B, D and E are each independently H.

In some embodiments of formula (II-V), each $R^1$ is independently H. In some embodiments of formula (II-V), each $R^1$ is independently halo (e.g., chloro). In some embodiments of formula (II-V), each $R^1$ is independently haloalkyl (e.g., trifluoromethyl).

In some embodiments of formula (II-V), one $R^1$ is halo and one $R^1$ is haloalkyl. In some embodiments of formula (II-V), one $R^1$ is chloro and one $R^1$ is trifluoromethyl.

In some embodiments of formula (II-V), $R^5$ is hydrogen.
In some embodiments of formula (II-V), $R^5$ is $C_{1-8}$ alkyl (e.g., methyl).

In some embodiments of formula (II-V), $R^4$ is hydrogen.
In some embodiments of formula (II-V), $R^4$ is $C_{1-8}$ alkyl or aryl substituted with n occurrences of $R^2$. In some embodiments of formula (II-V), $R^4$ is $C_{1-8}$ alkyl (e.g., methyl or ethyl) substituted with n occurrences of $R^2$.

In some embodiments of formula (II-V), each $R^2$ is independently selected from halo, haloalkyl, alkyl, aryl, heteroaryl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted.

In some embodiments of formula (II-V), n is 0. In some embodiments of formula (II-V), n is 1. In some embodiments of formula (II-V), $R^2$ is —$OR^a$. In some embodiments of formula (II-V), $R^a$ is alkyl (e.g., methyl). In some embodiments of formula (II-V), $R^2$ is optionally substituted heteroaryl. In some embodiments of formula (II-V), $R^2$ is optionally substituted monocyclic heteroaryl (e.g., 3-pyridyl). In some embodiments of formula (II-V), $R^2$ is optionally substituted aryl. In some embodiments of formula (II-V), $R^2$ is optionally substituted monocyclic aryl (e.g., 4-chlorophenyl).

In some embodiments of formula (II-V), $R^4$ is aryl (e.g., phenyl) substituted with n occurrences of $R^2$. In some embodiments of formula (II-V), $R^4$ is phenyl substituted with n occurrences of $R^2$. In some embodiments of formula (II-V), n is 0.

In some embodiments of formula (II-V), n is 1. In some embodiments of formula (II-V), $R^2$ is halo (e.g., fluoro or chloro). In some embodiments of formula (II-V), $R^2$ is haloalkyl (e.g., trifluoromethyl). In some embodiments of formula (II-V), $R^2$ is alkyl (e.g., methyl or ethyl). In some embodiments of formula (II-V), $R^2$ is heteroaralkyl. In some embodiments of formula (II-V), $R^2$ is optionally substituted monocyclic heteroaralkyl (e.g., methyl-4-trifluoromethyl-2-pyridyl). In some embodiments of formula (II-V), $R^2$ is cyano. In some embodiments of formula (II-V), $R^2$ is —$OR^a$. In some embodiments of formula (II-V), $R^a$ is alkyl (e.g., methyl). In some embodiments of formula (II-V), $R^2$ is $COOR^b$. In some embodiments of formula (II-V), $R^b$ is alkyl (e.g., ethyl). In some embodiments of formula (II-V), $R^2$ is optionally substituted monocyclic heteroaryl. In some embodiments of formula (II-V), $R^2$ is optionally substituted pyridyl. In some embodiments of formula (II-V), $R^2$ is pyridyl substituted with haloalkyl (e.g., trifluoromethyl).

In some embodiments of formula (II-V), n is 2. In some embodiments of formula (II-V), both $R^2$ are halo (e.g., fluoro or chloro). In some embodiments of formula (II-V), n is 2. In some embodiments of formula (II-V), both $R^2$ are alkyl (e.g., methyl). In some embodiments of formula (II-V), n is 2. In some embodiments of formula (II-V), one $R^2$ is halo (e.g., fluoro or chloro) and one is alkyl (e.g., methyl). In some embodiments of formula (II-V), n is 2. In some embodiments of formula (II-V), one $R^2$ is halo and one is —$CONR^cR^{c'}$. In some embodiments of formula (II-V), n is 2. In some embodiments of formula (II-V), one $R^2$ is chloro and one is —$CONHR^{c'}$. In some embodiments of formula (II-V), $R^{c'}$ is alkyl (e.g., methyl or isopropyl). In some embodiments of formula (II-V), n is 2. In some embodiments of formula (II-V), one $R^2$ is alkyl and one is —$CONR^cR^{c'}$. In some embodiments of formula (II-V), n is 2. In some embodiments of formula (II-V), one $R^2$ is methyl and one is —$CONHR^{c'}$. In some embodiments of formula (II-V), $R^{c'}$ is alkyl (e.g., methyl or isopropyl).

In some embodiments of formula (II-V), n is 2. In some embodiments of formula (II-V), one $R^2$ is haloalkyl (e.g., trifluoromethyl) and the other is —$OR^a$. In some embodiments of formula (II-V), $R^a$ is alkyl (e.g., methyl). In some embodiments of formula (II-V), n is 2. In some embodiments of formula (II-V), one $R^2$ is halo and the other is —$OR^a$. In some embodiments of formula (II-V), n is 2. In some embodiments of formula (II-V), one $R^2$ is chloro and the other is —$OR^a$. In some embodiments of formula (II-V), $R^a$ is optionally substituted heteroaryl. In some embodiments of formula (II-V), n is 2. In some embodiments of formula (II-V), both $R^2$ are —$OR^a$. In some embodiments of formula (II-V), $R^a$ is alkyl (e.g., methyl). In some embodiments of formula (II-V), $R^a$ is optionally substituted pyridyl. In some embodiments of formula (II-V), $R^a$ is pyridyl substituted with haloalkyl (e.g., trifluoromethyl). In some embodiments of formula (IT-V), $R^a$ is optionally substituted heterocyclyl. In some embodiments of formula (II-V), $R^a$ is an optionally substituted 5-membered heterocyclyl. In some embodiments of formula (II-V), $R^a$ is optionally substituted pyrrolidinyl. In some embodiments of formula (II-V), $R^a$ is N-methylpyrrolidinyl. In some embodiments of formula (II-V), $R^a$ is:

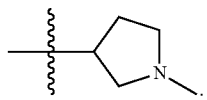

In some embodiments of formula (II-V), n is 2. In some embodiments of formula (II-V), two $R^2$, together with the carbon atoms to which they are attached, form a 5-membered heterocyclic ring. In some embodiments of formula (II-V), two $R^2$, together with the phenyl ring to which they are attached, form the following structure:

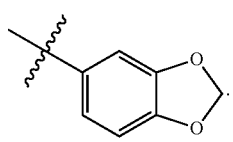 [SMILES: *c1ccc2c(c1)OCO2]

In some embodiments of formula (II-V), n is 3. In some embodiments of formula (II-V), each $R^2$ is halo (e.g., fluoro). In some embodiments of formula (II-V), n is 3. In some embodiments of formula (II-V), two $R^2$ are halo and one $R^2$ is —$CONR^cR^{c'}$. In some embodiments of formula (II-V), two $R^2$ are chloro and one $R^2$ is —$CONHR^{c'}$. In some embodiments of formula (II-V), $R^{c'}$ is alkyl (e.g., methyl or isopropyl). In some embodiments of formula (II-V), one $R^2$ is chloro, one $R^2$ is bromo, and one $R^2$ is —$CONHR^{c'}$. In some embodiments of formula (II-V), $R^{c'}$ is alkyl (e.g., methyl or isopropyl). In some embodiments of formula (II-V), n is 3. In some embodiments of formula (II-V), one $R^2$ is halo, one $R^2$ is alkyl, and one $R^2$ is —$CONR^cR^c$. In some embodiments of formula (II-V), one $R^2$ is chloro, one $R^2$ is methyl, and one $R^2$ is —$CONHR^{c'}$. In some embodiments of formula (II-V), $R^{c'}$ is alkyl (e.g., methyl or isopropyl). In some embodiments of formula (II-V), one $R^2$ is bromo, one $R^2$ is methyl, and one $R^2$ is —$CONHR^{c'}$. In some embodiments of formula (II-V), $R^{c'}$ is alkyl (e.g., methyl or isopropyl).

In some embodiments of formula (II-V), $R^3$ is halo (e.g., chloro or bromo). In some embodiments of formula (II-V), $R^3$ is haloalkyl (e.g., trifluoromethyl). In some embodiments of formula (II-V), $R^3$ is —$OR^a$. In some embodiments of formula (II-V), $R^a$ is haloalkyl (e.g., difluoromethoxy, trifluoromethoxy or trifluoroethoxy). In some embodiments of formula (II-V), $R^a$ is —$CH_2CF_3$.

In another aspect, the invention features a pharmaceutical composition comprising a compound of formula (II-Va):

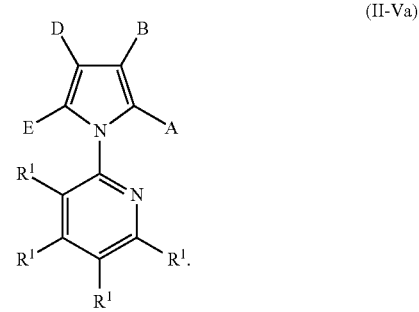

wherein

B and D are each independently selected from H and $SO_2NR^4R^5$; wherein at least one of B or D is —$SO_2$—$NR^4R^5$;

A and E are each independently selected from H and $R^3$;

each $R^1$ is independently selected from hydrogen, halo and haloalkyl;

$R^4$ is hydrogen, $C_{1-8}$ alkyl, and aryl, substituted with n occurrences of $R^2$;

each $R^2$ is independently selected from halo, haloalkyl, alkyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from halo, haloalkyl and —$OR^a$;

$R^5$ is hydrogen or $C_{1-8}$ alkyl;

$R^a$ is independently selected from alkyl, haloalkyl, optionally substituted heteroaryl and optionally substituted heterocyclyl;

each $R^b$ is independently alkyl;

each $R^c$ is independently selected from hydrogen and alkyl; and n is 0, 1, 2, or 3.

In some embodiments of formula (II-Va), A and E are each H.

In some embodiments of formula (II-Va), B is —$SO_2NR^4R^5$ and D is H. In some embodiments of formula (II-Va), B is H and D is —$SO_2NR^4R^5$.

In one aspect, the present invention features a compound or pharmaceutically acceptable salt thereof of formula (II-VI):

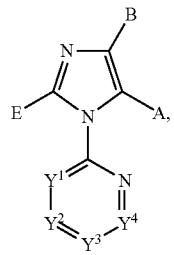

(II-VI)

wherein
A, B and E are each independently selected from H, —SO$_2$—NR$^4$R$^5$ and R$^3$; wherein at least one of A, B or E is —SO$_2$—NR$^4$R$^5$;
Y$^1$, Y$^2$, Y$^3$ and Y$^4$ are each independently selected from N and CR$^1$, wherein at least one of Y$^1$, Y$^2$, Y$^3$ and Y$^4$ are N;
each R$^4$ is independently selected from C$_{1-8}$ alkyl, aryl and heteroaryl, each of which is substituted with n occurrences of R$^2$;
each R$^5$ is independently hydrogen or C$_{1-8}$ alkyl;
each R$^1$ is independently selected from hydrogen, C$_{1-8}$ alkyl, C$_{1-8}$ terminal alkynyl, C$_{1-8}$ alkoxy, halogen, haloalkyl and haloalkoxy;
each R$^2$ is independently selected from halo, haloalkyl, C$_{1-4}$ alkyl, C$_{2-4}$ alkenyl, C$_{2-4}$ alknynyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;
each R$^3$ is independently selected from C$_{1-8}$ alkyl, —OR$^a$, halogen, haloalkyl, haloalkoxy and optionally substituted heteroaryl;
each R$^a$ is independently selected from alkyl, haloalkyl, optionally substituted heteroaryl and optionally substituted heterocyclyl;
each R$^b$ is independently alkyl; and
each R$^c$ is independently selected from hydrogen and alkyl; and
n is 0, 1, 2 or 3.

In some embodiments of formula (II-VI), at least one of Y$^1$, Y$^2$, Y$^3$ and Y$^4$ is N. In some embodiments of formula (II-VI), at least one of Y$^1$, Y$^2$, Y$^3$ and Y$^4$ are CH. In some embodiments of formula (II-VI), Y$^1$ is N. In some embodiments of formula (II-VI), Y$^3$ is N.

In some embodiments of formula (II-VI), each R$^1$ is independently hydrogen.

In some embodiments of formula (II-VI), the invention features a compound of formula (II-VIa):

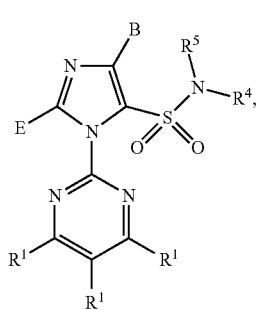

(II-VIa)

wherein n, B, E, R$^1$, R$^2$, R$^3$, R$^4$ and R$^5$ are defined as above.

In some embodiments of formula (II-VI), the invention features a compound of formula (II-VIb):

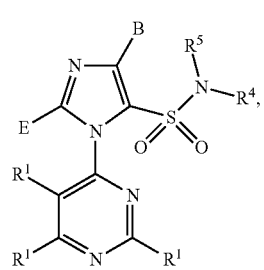

(II-VIb)

wherein n, B, E, R$^1$, R$^2$, R$^3$, R$^4$ and R$^5$ are defined as above.
In some embodiments of formula (II-VI), B and E are each independently selected from H.
In some embodiments of formula (II-VI), R$^5$ is hydrogen.
In some embodiments of formula (II-VI), each R$^1$ is independently hydrogen. In some embodiments of formula (II-VI), each R$^1$ is independently selected from C$_{1-8}$ alkyl, halogen or haloalkyl. In some embodiments of formula (II-VI), each R$^1$ is independently selected from halogen or haloalkyl. In some embodiments of formula (II-VI), each R$^1$ is independently selected from halogen (e.g., chlorine or fluorine). In some embodiments of formula (II-VI), each R$^1$ is independently haloalkyl (e.g., trifluoroalkyl).
In some embodiments of formula (II-VI), R$^4$ is selected from aryl or heteroaryl. In some embodiments of formula (II-VI), R$^4$ is aryl substituted with n occurrences of R$^2$. In some embodiments of formula (II-VI), R$^4$ is C$_{5-8}$ monocyclic aryl or C$_{8-14}$ bicyclic aryl. In some embodiments of formula (II-VI), R$^4$ is C$_{5-8}$ monocyclic aryl (e.g., optionally substituted phenyl). In some embodiments of formula (II-VI), R$^4$ is phenyl substituted with n occurrences of R$^2$. In some embodiments of formula (II-VI), R$^2$ is heteroaryl substituted with n occurrences of R$^2$. In some embodiments of formula (II-VI), R$^4$ is a 5-8 membered heteroaryl or 8-14 membered heteroaryl. In some embodiments of formula (II-VI), R$^4$ is an 8-12 membered heteroaryl (e.g., 5-quinolyl or 6-quinolyl). In some embodiments of formula (II-VI), R$^4$ is quinolyl (e.g., 5-quinolyl or 6-quinolyl) substituted with n occurrences of R$^2$.

In some embodiments of formula (II-VI), n is 0. In some embodiments of formula (II-VI), n is 1.
In some embodiments of formula (II-VI), R$^2$ is halo, C$_{1-4}$ alkyl or haloalkyl, each of which can be further substituted. In some embodiments of formula (II-VI), R$^2$ is C$_{1-4}$ alkyl (e.g., ethyl). In some embodiments of formula (II-VI), R$^2$ is halo (e.g., fluoro or chloro). In some embodiments of formula (II-VI), R$^2$ is haloalkyl (e.g., trifluoromethyl).
In some embodiments of formula (II-VI), n is 2. In some embodiments of formula (II-VI), both R$^2$ are C$_{1-4}$ alkyl (e.g., methyl). In some embodiments of formula (II-VI), n is 2. In some embodiments of formula (II-VI), both R$^2$ are halo (e.g., fluoro or chloro). In some embodiments of formula (II-VI), n is 2. In some embodiments of formula (II-VI), one R$^2$ is haloalkyl (e.g., trifluoroalkyl) and the other R$^2$ is —OR$^a$. In some embodiments of formula (II-VI), R$^a$ is alkyl (e.g., methyl or ethyl). In some embodiments of formula (II-VI), n is 2. In some embodiments of formula (II-VI), on R$^2$ is halo (e.g., fluoro or chloro) and the other R$^2$ is C$_{1-4}$ alkyl (e.g., methyl or ethyl).

In some embodiments of formula (II-VI), n is 2. In some embodiments of formula (II-VI), two $R^2$, together with the carbon atoms to which they are attached, form a 5-membered heterocyclic ring. In some embodiments of formula (II-VI), two $R^2$, together with the phenyl ring to which they are attached, form the following structure:

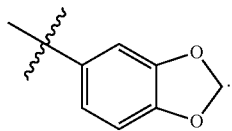 [SMILES: *c1ccc2c(c1)OCO2]

In some embodiments of formula (II-VI), n is 3. In some embodiments of formula (II-VI), all $R^2$ are halo (e.g., fluoro or chloro).

In one aspect, the present invention features a compound or pharmaceutically acceptable salt thereof of formula (II-VII):

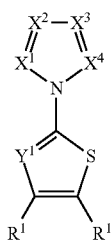

(II-VII)

wherein
$X^1$ is N or CE;
$X^2$ is N or CD;
$X^3$ is N or CB;
$X^4$ is N or CA, wherein at least one of $X^1$, $X^2$, $X^3$ and $X^4$ is N and at least one of $X^1$, $X^2$, $X^3$, $X^4$, is C—SO$_2$—NR$^4$R$^5$;
A, B, D and E are each independently selected from H, $R^3$ and —SO$_2$—NR$^4$R$^5$;
$Y^1$ is selected from N and CR$^1$;
each $R^4$ is independently selected from $C_{1-8}$ alkyl, aryl and heteroaryl, each of which is substituted with n occurrences of $R^2$;
$R^5$ is hydrogen or $C_{1-8}$ alkyl;
each $R^1$ is independently selected from hydrogen, $C_{1-8}$ alkyl, $C_{1-8}$ terminal alkynyl, $C_{1-8}$ alkoxy, halogen, haloalkyl and haloalkoxy;
each $R^2$ is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —OR$^a$, —COOR$^b$ and —CONR$^c$R$^{c'}$; wherein two $R^2$, together with the carbons to which they are attached, may form an optionally substituted ring, each of which can be further substituted;
each $R^3$ is independently selected from $C_{1-8}$ alkyl, —OR$^a$, halogen, haloalkyl, haloalkoxy and optionally substituted heteroaryl;
each $R^a$ is independently selected from alkyl, haloalkyl, optionally substituted heteroaryl and optionally substituted heterocyclyl;
each $R^b$ is independently alkyl; and
each $R^c$ is independently selected from hydrogen and alkyl; and
n is 0, 1, 2 or 3.

In some embodiments of formula (II-VII), the invention features a compound of formula (II-VIIa):

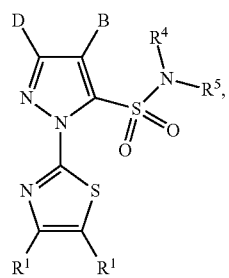

(II-VIIa)

wherein n, B, D, $R^1$, $R^4$, $R^2$ and $R^5$ are defined as in formula (II-VII).

In some embodiments of formula (II-VII), the invention features a compound of formula (II-VIIa):

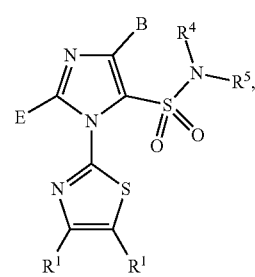

(II-VIIb)

wherein n, B, E, $R^1$, $R^4$, $R^2$ and $R^5$ are defined as in formula (II-VII).

In some embodiments of formula (II-VII), the invention features a compound of formula (II-VIIb):

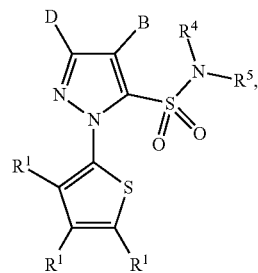

(II-VIIb)

wherein n, B, D, $R^1$, $R^4$, $R^2$ and $R^5$ are defined as in formula (II-VII).

In some embodiments of formula (II-VII), the invention features a compound of formula (II-VIIa):

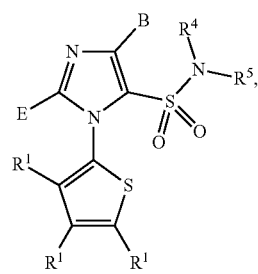

(II-VIId)

wherein n, B, E, $R^1$, $R^4$, $R^2$ and $R^5$ are defined as in formula (II-VII).

In some embodiments of formula (II-VII), B and E are each independently selected from H.

In some embodiments of formula (II-VII), B and D are each independently selected from H.

In some embodiments of formula (II-VII), $R^5$ is hydrogen.

In some embodiments of formula (II-VII), each $R^1$ is independently hydrogen. In some embodiments of formula (II-VII), each $R^1$ is independently selected from $C_{1-8}$ alkyl, halogen or haloalkyl. In some embodiments of formula (II-VII), each $R^1$ is independently selected from halogen or haloalkyl. In some embodiments of formula (II-VII), each $R^1$ is independently selected from halogen (e.g., chlorine or fluorine). In some embodiments of formula (II-VII), each $R^1$ is independently haloalkyl (e.g., trifluoroalkyl).

In some embodiments of formula (II-VII), $R^4$ is selected from aryl or heteroaryl. In some embodiments of formula (II-VII), $R^4$ is aryl substituted with n occurrences of $R^2$. In some embodiments of formula (II-VII), $R^4$ is $C_{5-8}$ monocyclic aryl or $C_{8-14}$ bicyclic aryl. In some embodiments of formula (II-VII), $R^4$ is $C_{5-8}$ monocyclic aryl (e.g., optionally substituted phenyl). In some embodiments of formula (II-VII), $R^4$ is phenyl substituted with n occurrences of $R^2$.

In some embodiments of formula (II-VII), n is 0. In some embodiments of formula (II-VII), n is 1.

In some embodiments of formula (II-VII), $R^2$ is halo, $C_{1-4}$ alkyl or haloalkyl, each of which can be further substituted.

In some embodiments of formula (II-VII), $R^2$ is $C_{1-4}$ alkyl (e.g., methyl or ethyl). In some embodiments of formula (II-VII), $R^2$ is halo (e.g., fluoro or chloro).

In some embodiments of formula (II-VII), n is 2. In some embodiments of formula (II-VII), both $R^2$ are $C_{1-4}$ alkyl (e.g., methyl or ethyl). In some embodiments of formula (II-VII), n is 2. In some embodiments of formula (II-VII), both $R^2$ are halo (e.g., fluoro or chloro). In some embodiments of formula (II-VII), n is 2. In some embodiments of formula (II-VII), one $R^2$ is haloalkyl (e.g., trifluoroalkyl) and the other $R^2$ is —$OR^a$. In some embodiments of formula (II-VII), $R^a$ is alkyl (e.g., methyl or ethyl). In some embodiments of formula (II-VII), n is 2. In some embodiments of formula (II-VII), one $R^2$ is $C_{1-4}$ alkyl (e.g., methyl or ethyl) and the other $R^2$ is halo (e.g., fluoro or chloro).

In some embodiments of formula (II-VII), n is 2. In some embodiments of formula (II-VII), two $R^2$, together with the carbon atoms to which they are attached, form a 5-membered heterocyclic ring. In some embodiments of formula (II-VII), two $R^2$, together with the phenyl ring to which they are attached, form the following structure:

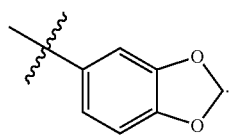 [SMILES: *c1ccc2c(c1)OCO2]

In some embodiments of formula (II-VII), n is 3. In some embodiments of formula (II-VII), all $R^2$ are halo (e.g., fluoro or chloro).

In another aspect, the invention features a pharmaceutical composition comprising a compound of formula (III) or a pharmaceutically acceptable salt thereof:

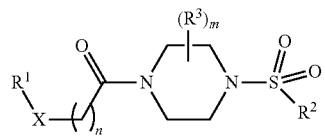

(III)

wherein:
m is 0, 1 or 2;
n is 0, 1 or 2;
X is O, S, $NR^b$, alkylenyl, cycloalkylenyl, or a bond;
$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl;
$R^2$ is an optionally substituted aryl or an optionally substituted heteroaryl;
each $R^3$ is independently selected from halo, alkyl, haloalkyl and —$OR^a$;
each $R^a$ is independently selected from alkyl, haloalkyl and optionally substituted heteroaryl; and
each $R^b$ is independently hydrogen or alkyl.

In some embodiments of formula (III), $R^1$ is an optionally substituted alkyl (e.g., methyl or t-butyl). In some embodiments of formula (III), $R^1$ is optionally substituted cycloalkyl (e.g., cyclopentyl or cyclohexyl).

In some embodiments of formula (III), $R^1$ is aryl (e.g., monocyclic aryl or bicyclic aryl). In some embodiments of formula (III), $R^1$ is an optionally substituted monocyclic aralkyl (e.g., benzyl or methylpyridyl). In some embodiments of formula (III), $R^1$ is an optionally substituted phenyl. In some embodiments of formula (III), $R^1$ is an optionally substituted naphthyl. In some embodiments of formula (III), $R^1$ is phenyl. In some embodiments of formula (III), $R^1$ is naphthyl.

In some embodiments of formula (III), $R^1$ is heteroaryl (e.g., monocyclic N-containing heteroaryl or bicyclic N-containing heteroaryl). In some embodiments of formula (III), $R^1$ is an optionally substituted monocyclic 5-8 membered heteroaryl (e.g., pyridyl, pyrimidyl, pyrazyl, oxazolyl, thiazolyl, triazolyl or imidazolyl). In some embodiments of formula (III), $R^1$ is an optionally substituted 6-12 membered bicyclic heteroaryl (e.g., quinolyl). In some embodiments of formula (III), $R^1$ is optionally substituted pyridyl (e.g., 2-pyridyl, 3-pyridyl or 4-pyridyl). In some embodiments of formula (III), $R^1$ is optionally substituted pyrimidyl (e.g., 2-pyrimidyl). In some embodiments of formula (III), $R^1$ is optionally substituted pyrazyl (e.g., 2-pyrazyl). In some embodiments of formula (III), $R^1$ is optionally substituted oxazolyl (e.g., 4-oxazolyl). In some embodiments of formula (III), $R^1$ is optionally substituted thiazolyl (e.g., 4-thiazolyl). In some embodiments of formula (III), $R^1$ is optionally substituted imidazolyl (e.g., 4-imidazolyl). In some embodiments of formula (III), $R^1$ is optionally substituted triazolyl (e.g., 4-triazolyl).

In some embodiments of formula (III), m is 0.

In some embodiments of formula (III), n is 0. In some embodiments of formula (III), X is oxygen (O). In some embodiments of formula (III), $R^1$ is optionally substituted straight or branched $C_{1-6}$ alkyl (e.g., methyl, ethyl, iso-propyl or t-butyl). In some embodiments of formula (III), $R^1$ is optionally substituted benzyl. In some embodiments of formula (III), $R^1$ is optionally substituted methyl-3-pyridyl). In some embodiments of formula (III), X is a bond. In some embodiments of formula (III), $R^1$ is optionally substituted cyclohexyl. In some embodiments of formula (III), $R^1$ is optionally substituted phenyl. In some embodiments of formula (III), X is cycloalkylenyl (e.g., cyclopropylenyl). In some embodiments of formula (III), R¹ is optionally substituted phenyl (e.g., phenyl or 4-trifluorophenyl).

In some embodiments of formula (III), n is 1. In some embodiments of formula (III), X is oxygen (O). In some embodiments of formula (III), R¹ is optionally substituted phenyl (e.g., phenyl, 4-methylphenyl, 4-methoxycarbonylphenyl, 4-fluorophenyl or 2,4-dichlorophenyl). In some embodiments of formula (III), R¹ is optionally substituted pyridyl (e.g., 3-pyridyl). In some embodiments of formula (III), R¹ is phenyl optionally substituted with heteroaryl (e.g., 4-tetrazolylphenyl). In some embodiments of formula (III), R¹ is optionally substituted benzyl. In some embodiments of formula (III), X is NR$^b$. In some embodiments of formula (III), R$^b$ is hydrogen (H). In some embodiments of formula (III), R¹ is optionally substituted alkyl (e.g., methyl). In some embodiments of formula (III), R¹ is optionally substituted phenyl. In some embodiments of formula (III), X is a bond. In some embodiments of formula (III), R¹ is optionally substituted phenyl (e.g., 2,5-bis(trifluoromethyl)phenyl or 4-trifluoromethylphenyl). In some embodiments of formula (III), R¹ is optionally substituted cyclopropyl. In some embodiments of formula (III), X is sulfur (S). In some embodiments of formula (III), R¹ is optionally substituted phenyl (e.g., phenyl or 4-methylphenyl).

In some embodiments of formula (III), n is 2. In some embodiments of formula (III), X is a bond. In some embodiments of formula (III), R¹ is optionally substituted phenyl (e.g., phenyl or 4-trifluoromethylphenyl).

In some embodiments of formula (III), R² is aryl (e.g., monocyclic aryl or bicyclic aryl). In some embodiments of formula (III), R² is optionally substituted phenyl. In some embodiments of formula (III), R² is optionally substituted naphthyl. In some embodiments of formula (III), R² is naphthyl(1-naphthyl or 2-naphthyl).

In some embodiments of formula (III), R² is optionally substituted heteroaryl (e.g., monocyclic N-containing heteroaryl or bicyclic N-containing heteroaryl). In some embodiments of formula (III), R² is an optionally substituted 5-8 membered monocyclic heteroaryl (e.g., pyridyl, pyrimidyl, or pyrrolyl). In some embodiments of formula (III), R² is an optionally substituted 6-12 membered bicyclic heteroaryl (e.g., quinolyl, isoquinolyl, quinazolinyl, quinaxolinyl, cinnolinyl, indolyl, benzoxazolyl, pyrrolopyridyl, benzimidazolyl, or benzthiazolyl). In some embodiments of formula (III), R² is optionally substituted pyridyl (e.g., 2-pyridyl, 3-pyridyl or 4-pyridyl). In some embodiments of formula (III), R² is optionally substituted pyrimidyl (e.g., 2-pyrimidyl). In some embodiments of formula (III), R² is optionally substituted quinolyl (e.g., 8-quinolyl). In some embodiments of formula (III), R² is optionally substituted isoquinolyl. In some embodiments of formula (III), R² is optionally substituted quinazolinyl (e.g., 2-quinazolinyl or 7-quinazolinyl). In some embodiments of formula (III), R² is optionally substituted quinoxalinyl (e.g., 2-quinoxalinyl, 6-quinoxalinyl). In some embodiments of formula (III), R² is optionally substituted cinnolinyl (e.g., 7-cinnolyl). In some embodiments of formula (III), R² is optionally substituted indolyl (e.g., 6-indolyl). In some embodiments of formula (III), R² is optionally substituted benzoxazolyl (e.g., 5-benzoxazolyl, 6-benzoxazolyl). In some embodiments of formula (III), R² is optionally substituted pyrrolopyridyl (e.g., 5-pyrrolopyridyl). In some embodiments of formula (III), R² is optionally substituted benzimidazolyl (e.g., 6-benzimidazolyl). In some embodiments of formula (III), R² is optionally substituted benzthiazolyl (e.g, 5-benzthiazolyl, 6-benzthiazolyl).

In some embodiments of formula (III), R² is an unsubstituted napthyl. In some embodiments of formula (III), R² is an optionally substituted phenyl. In some embodiments of formula (III), R² is phenyl substituted with halo (e.g., 3,5-dichlorophenyl, 2,6-difluorophenyl or 4-fluorophenyl). In some embodiments of formula (III), R² is phenyl substituted with halo alkyl (e.g., 3-trifluoromethylphenyl). In some embodiments of formula (III), R² is phenyl disubstituted with halo alkyl (e.g., 3,5-bis(trifluoromethyl)phenyl). In some embodiments of formula (III), R² is phenyl substituted with one halo and one alkoxy (e.g., 2-methoxy-5-chlorophenyl). In some embodiments of formula (III), R² is phenyl substituted with one haloalkyl and one halo (e.g., 3-bromo-5-trifluoromethylphenyl). In some embodiments of formula (III), R² is phenyl substituted with one haloalkyl and one cycloalkyl (e.g, 3-cyclopropyl-5-trifluoromethylphenyl). In some embodiments of formula (III), R² is phenyl substituted with one haloalkyl and one acyl group (e.g., 3-trifluoromethyl-5-methoxycarbonylphenyl). In some embodiments of formula (III), R² is disubstituted phenyl, wherein the two substituents, when taken together with the carbon atoms to which they are attached, form an optionally substituted ring. In some embodiments of formula (III), R² is disubstituted phenyl, wherein the two substituents, taken together with the carbon atoms to which they are attached, form a 5-6 membered heterocyclic ring. In some embodiments of formula (III), R² is disubstituted phenyl, wherein the two substituents, taken together with the carbon atoms to which they are attached, form the following structure:

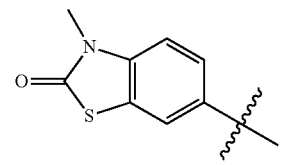 [SMILES: *c1ccc2c(c1)sc(=O)n2C]

In some embodiments of formula (III), R² is disubstituted phenyl, wherein the two substituents, taken together with the carbon atoms to which they are attached, form the following structure:

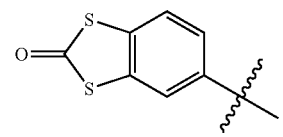 [SMILES: *c1ccc2sc(=O)sc2c1]

In some embodiments of formula (III), R² is disubstituted phenyl, wherein the two substituents, taken together with the carbon atoms to which they are attached, form the following structure:

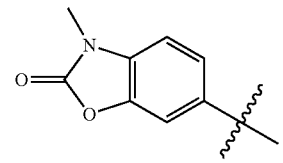 [SMILES: *c1ccc2c(c1)oc(=O)n2C]

In some embodiments of formula (III), R² is disubstituted phenyl, wherein the two substituents, taken together with the carbon atoms to which they are attached, form the following structure:

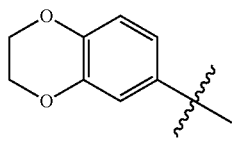 [SMILES: *c1ccc2c(c1)OCCO2]

In some embodiments of formula (III), $R^2$ is an optionally substituted pyrrolyl. In some embodiments of formula (III), $R^2$ is pyrrolyl substituted with an optionally substituted pyrimidyl (e.g., 3-trifluoromethyl-6-chloro-2-pyrimidyl).

In some embodiments of formula (III), $R^2$ is an N-containing monocyclic heteroaryl, m is 0, n is 1, X is O and $R^1$ is optionally substituted aryl.

In some embodiments of formula (III), provided is a compound of formula (III-II) or a pharmaceutically acceptable salt thereof:

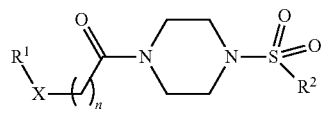
(III-II)

wherein:

n is 0, 1 or 2;

X is O, S, $NR^b$, or cycloalkylenyl;

$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl; provided that when n is 0 and X is O, then $R^1$ is selected from optionally substituted aryl, optionally substituted heteroaryl, optionally substituted heterocyclyl, optionally substituted cycloalkyl, an optionally substituted aralkyl, or optionally substituted heteroaralkyl;

$R^2$ is a bicyclic heteroaryl; and each $R^b$ is independently hydrogen or alkyl.

In some embodiments (e.g., of formula (III), (III-II), (III-II-a), (III-III) or (III-IV)), $R^b$ is H, $CH_3$ or $CH_2CH_3$. In some embodiments (e.g., of formula (III), (III-II), (III-II-a), (III-III) or (III-IV)), cycloalkylenyl is cyclopropylenyl.

In some embodiments of formula (III-II), provided is a compound of formula (III-II-a) or a pharmaceutically acceptable salt thereof:

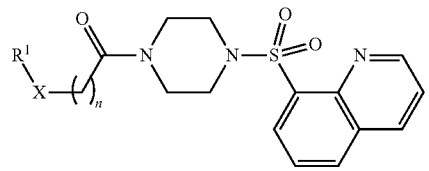
(III-II-a)

where n, X, $R^1$ and $R^b$ are as defined in formula (III-II).

In some embodiments of formula (III), provided is a compound of formula (III-III) or a pharmaceutically acceptable salt thereof:

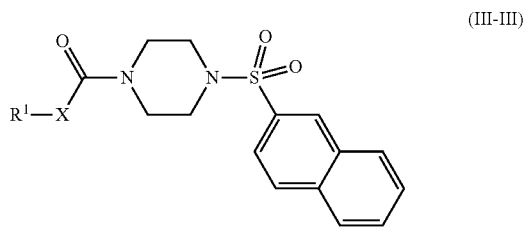
(III-III)

wherein:

when X is S, $NR^b$, or cycloalkylenyl, $R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl;

when X is O, $R^1$ is selected from an optionally substituted aralkyl, or optionally substituted heteroaralkyl; and each $R^b$ is independently hydrogen or alkyl.

In some embodiments of formula (III), provided is a compound of formula (III-IV) or a pharmaceutically acceptable salt thereof:

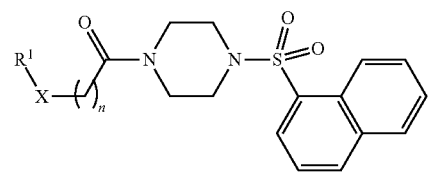
(III-IV)

wherein:

when n is 0, X is S, $NR^b$, or cycloalkylenyl;

when n is 1 or 2, X is O, X is S, $NR^b$, or cycloalkylenyl;

$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl; and each $R^b$ is independently hydrogen or alkyl.

In another aspect, the present invention includes a compound of formula (IV),

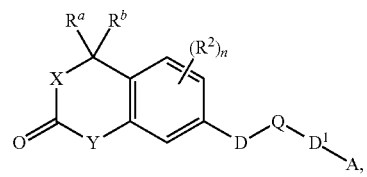
(IV)

wherein

X and Y are each independently selected from O and N(-L-$R^1$);

Q is C(O), $SO_2$, or $—(CH_2)_h—$;

each L is independently selected from a bond, —C(O)—, $—(CR^aR^b)_m—$, $—C(O)N(R^c)—$ or —C(O)O—;

D and $D^1$ are each independently selected from a bond, O and $N(R^c)$, provided that D and $D^1$ are not both a bond;

A is aryl or heteroaryl, each of which is substituted with 0-3 occurrences of $R^d$; and D-Q-$D^1$-A is not $OCH_2$-phenyl;

each $R^1$ is independently selected from hydrogen, $C_{1-4}$ alkyl, halo $C_{1-4}$alkyl, alkyl-O-alkylene, $C_{3-10}$ cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$;

each $R^a$ and each $R^b$ are independently selected from hydrogen, $C_{1-4}$ alkyl, or $R^a$ and $R^b$ bound to the same carbon atom are taken together with the carbon atom to form a cycloalkyl;

each $R^c$ is independently selected from hydrogen and $C_{1-4}$alkyl;

each $R^d$ is independently selected from halo, halo $C_{1-4}$ alkyl, $C_{1-4}$ alkyl, nitro, cyano, —OH and —O($C_{1-4}$ alkyl), or two $R^d$, attached to the same or adjacent carbon atoms, taken together with the atom(s) to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$alkoxy and hydroxyl;

h is 1, 2 or 3;

each m is independently 1, 2 or 3; and each n is independently 0, 1, 2 or 3;

provided that the compound is not 2-chloro-N-(1,4-dihydro-2-oxo-2H-3,1-benzoxazin-7-yl)-5-[[(1-methylethyl) amino]sulfonyl]-benzamide;

4-[2-oxo-7-(phenylmethoxy)-2H-1,3-benzoxazin-3(4H)-yl], Benzoic methyl ester;

2-chloro-5-[[(1-methylethyl)amino]sulfonyl]-N-(1,2,3,4-tetrahydro-2-oxo-7-quinazolinyl)-benzamide; or 2-chloro-5-[[(1-methylethyl)amino]sulfonyl]-N-(1,2,3,4-tetrahydro-3-methyl-2-oxo-7-quinazolinyl)-benzamide.

In certain embodiments of Formula (IV), D is a bond.

In some embodiments of Formula (IV), D is N($R^c$). In one aspect of these embodiments of Formula (IV), $R^c$ is hydrogen.

In certain embodiments of Formula (IV), D is a bond and $D^1$ is N($R^c$). In one aspect of these embodiments of Formula (IV), Q is $SO_2$. In another aspect of these embodiments of Formula (IV), Q is C(O). In a more particular aspect of these embodiments of Formula (IV), $D^1$ is NH and Q is C(O). In another aspect of these embodiments of Formula (IV), Q is $(CH_2)_h$. In a more particular aspect of these embodiments of Formula (IV), Q is $CH_2$. In another more particular aspect of these embodiments of Formula (IV), $D^1$ is NH and Q is $(CH_2)_h$. In an even more particular aspect of these embodiments of Formula (IV), $D^1$ is NH and Q is $CH_2$.

In some embodiments of Formula (IV), $D^1$ is oxygen.

In some embodiments of Formula (IV), D is a bond and $D^1$ is oxygen. In one aspect of these embodiments of Formula (IV), Q is C(O).

In some embodiments of Formula (IV), D is oxygen. In one aspect of these embodiments of Formula (IV), Q is C(O) and $D^1$ is N($R^c$).

In some embodiments of Formula (IV), $D^1$ is N($R^c$). In one aspect of these embodiments of Formula (IV), D is NH. In another aspect of these embodiments of Formula (IV), Q is C(O) and D is oxygen.

In certain embodiments of Formula (IV), Q is $SO_2$.

In some embodiments of Formula (IV), Q is $(CH_2)_h$. In one aspect of these embodiments of Formula (IV), h is 1.

In some embodiments of Formula (IV), Q is C(O).

In certain embodiments of Formula (IV), $R^a$ is hydrogen.

In certain embodiments of Formula (IV), $R^b$ is hydrogen.

In another aspect, the present invention includes a compound of Formula (IV), wherein D is a bond, Q is $S(O)_2$, and $D^1$ is —NH—, the compound having the formula (IVa):

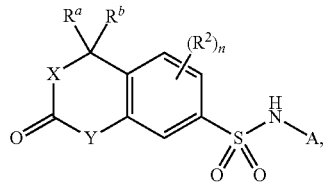

(IVa)

wherein X, Y, L, $R^a$, $R^b$, $R^c$, $R^d$, $R^f$, $R^g$, $R^1$, $R^2$, A, n and m are as described above for Formula (IV).

The following embodiments and aspects thereof relate to both Formula (IV) and Formula (IVa).

In some embodiments of Formulas (IV) and (IVa), Y is N-L-$R^1$.

In certain embodiments of Formulas (IV) and (IVa), Y is N-L-$R^1$ and L is a bond. In one aspect of these embodiments of Formulas (IV) and (IVa), $R^1$ is hydrogen. In still another aspect of these embodiments of Formulas (IV) and (IVa), $R^1$ is $C_{1-4}$ alkyl substituted with 0-3 occurrences of $R^g$. In a more specific aspect of these embodiments of Formulas (IV) and (IVa), $R^1$ is $C_{1-4}$ alkyl substituted with 0 occurrences of $R^g$ (e.g., methyl).

In certain embodiments of Formulas (IV) and (IVa), Y is N-L-$R^1$ and L is —$(CR^aR^b)_m$—. In a specific aspect of these embodiments of Formulas (IV) and (IVa), L is —$CR^aR^b$— (e.g., m is 1). In an even more specific aspect of these embodiments of Formulas (IV) and (IVa), L is —$CH_2$— (e.g, $R^a$ and $R^b$ are hydrogen). In another specific aspect of these embodiments of Formulas (IV) and (IVa), $R^1$ is aryl substituted with 0-3 occurrences of $R^f$. In a more specific aspect of these embodiments of Formulas (IV) and (IVa), $R^1$ is unsubstituted phenyl.

In certain embodiments of Formulas (IV) and (IVa), X is O.

In certain embodiments of Formulas (IV) and (IVa), X is O and Y is N-L-$R^1$.

In certain embodiments of Formulas (IV) and (IVa), X is O, Y is N-L-$R^1$ and L is a bond. In one aspect of these embodiments of Formulas (IV) and (IVa), $R^1$ is hydrogen. In still another aspect of these embodiments of Formulas (IV) and (IVa), $R^1$ is $C_{1-4}$ alkyl substituted with 0-3 occurrences of $R^g$. In a more specific aspect of these embodiments of Formulas (IV) and (IVa), $R^1$ is $C_{1-4}$ alkyl substituted with 0 occurrences of $R^g$ (e.g., methyl).

In certain embodiments of Formulas (IV) and (IVa), X is O, Y is N-L-$R^1$ and L is —$(CR^aR^b)_m$—. In a specific aspect of these embodiments of Formulas (IV) and (IVa), L is —$CR^aR^b$— (e.g., m is 1). In an even more specific aspect of these embodiments of Formulas (IV) and (IVa), L is —$CH_2$— (e.g, $R^a$ and $R^b$ are hydrogen). In another specific aspect of these embodiments of Formulas (IV) and (IVa), $R^1$ is aryl substituted with 0-3 occurrences of $R^f$. In a more specific aspect of these embodiments of Formulas (IV) and (IVa), $R^1$ is unsubstituted phenyl.

In certain embodiments of Formulas (IV) and (IVa), X is N-L-$R^1$.

In certain embodiments of Formulas (IV) and (IVa), X is N-L-R¹, and L is a bond. In one aspect of these embodiments of Formulas (IV) and (IVa), R¹ is hydrogen. In still another aspect of these embodiments of Formulas (IV) and (IVa), R¹ is $C_{1-4}$ alkyl substituted with 0-3 occurrences of $R^g$. In a more specific aspect of these embodiments of Formulas (IV) and (IVa), R¹ is $C_{1-4}$ alkyl substituted with 0 occurrences of $R^g$ (e.g., methyl).

In some embodiments of Formulas (IV) and (IVa), X is N-L-R¹, and L is —$(CR^aR^b)_m$—. In a specific aspect of these embodiments of Formulas (IV) and (IVa), L is —$CR^aR^b$— (e.g., m is 1). In an even more specific aspect of these embodiments of Formulas (IV) and (IVa), L is —$CH_2$— (e.g, $R^a$ and $R^b$ are hydrogen). In another specific aspect of these embodiments of Formulas (IV) and (IVa), R¹ is aryl substituted with 0-3 occurrences of $R^f$. In a more specific aspect of these embodiments of Formulas (IV) and (IVa), R¹ is unsubstituted phenyl.

In some embodiments of Formulas (IV) and (IVa), Y is O.

In some embodiments of Formulas (IV) and (IVa), Y is O and X is N-L-R¹.

In certain embodiments of Formulas (IV) and (IVa), X is N-L-R¹, Y is O and L is a bond. In one aspect of these embodiments of Formulas (IV) and (IVa), R¹ is hydrogen. In still another aspect of these embodiments of Formulas (IV) and (IVa), R¹ is $C_{1-4}$ alkyl substituted with 0-3 occurrences of $R^f$. In a more specific aspect of these embodiments of Formulas (IV) and (IVa), R¹ is $C_{1-4}$ alkyl substituted with 0 occurrences of $R^f$ (e.g., methyl).

In some embodiments of Formulas (IV) and (IVa), X is N-L-R¹, Y is O and L is —$(CR^aR^b)_m$—. In a specific aspect of these embodiments of Formulas (IV) and (IVa), L is —$CR^aR^b$— (e.g., m is 1). In an even more specific aspect of these embodiments of Formulas (IV) and (IVa), L is —$CH_2$— (e.g, $R^a$ and $R^b$ are hydrogen). In another specific aspect of these embodiments of Formulas (IV) and (IVa), R¹ is aryl substituted with 0-3 occurrences of $R^f$. In a more specific aspect of these embodiments of Formulas (IV) and (IVa), R¹ is unsubstituted phenyl.

In certain embodiments of Formulas (IV) and (IVa), n is 0.

In some embodiments of Formulas (IV) and (IVa), n is 1.

In certain embodiments of Formulas (IV) and (IVa), A is aryl (e.g., monocyclic or bicyclic aryl) substituted with 0-3 occurrences of $R^d$. In one aspect of these embodiments of Formulas (IV) and (IVa), A is 5-8 membered monocyclic aryl substituted with 0-3 occurrences of $R^d$. In a more specific aspect of these embodiments of Formulas (IV) and (IVa), A is phenyl substituted with 0-3 occurrences of $R^d$. In an even more specific aspect of these embodiments of Formulas (IV) and (IVa), A is phenyl substituted with 0 occurrences of $R^d$. In another even more specific aspect of these embodiments of Formulas (IV) and (IVa), A is phenyl substituted with 1 occurrence of $R^d$.

In some aspects of embodiments of Formulas (IV) and (IVa), when A is phenyl substituted with 1 occurrence of $R^d$, that $R^d$ is halo (e.g., A is p-fluorophenyl or m-chlorophenyl). In another aspect of these embodiments of Formulas (IV) and (IVa), the $R^d$ substituent on A is alkyl (e.g., methyl or ethyl). In still another aspect of these embodiments of Formulas (IV) and (IVa), the $R^d$ substituent on A is —$OR^a$ (e.g., p-substituted —$OR^a$). In some embodiments of Formulas (IV) and (IVa), the $R^d$ substituent on A is alkoxy (e.g., methoxy).

In certain embodiments of Formulas (IV) and (IVa), A is phenyl substituted with 2 occurrences of $R^d$. In one aspect of these embodiments of Formulas (IV) and (IVa), both $R^d$ substituents on A are halo (e.g., 3-chloro-4-fluorophenyl). In another aspect of these embodiments of Formulas (IV) and (IVa), both $R^d$ substituents on A are alkyl (e.g., 3,5-dimethylphenyl). In still another aspect of these embodiments of Formulas (IV) and (IVa), one $R^d$ substituent on A is alkyl and the other is halo (e.g., 3-methyl-4-fluorophenyl). In yet another aspect of these embodiments of Formulas (IV) and (IVa), two $R^d$ substituents on A, attached to the same or adjacent carbon atoms are taken together with the atoms to which they are attached form an optionally substituted heterocyclyl.

In another aspect, the present invention includes a compound of Formula (V),

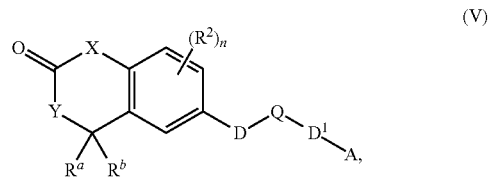

wherein

X and Y are each independently selected from O and N-L-R¹;

Q is C(O), $SO_2$, or —$(CH_2)_h$—;

each L is independently selected from a bond, —C(O)—, —$(CR^aR^b)_m$—, —C(O)NR$^c$— or —C(O)O—;

D and D¹ are each independently selected from a bond, O and NR$^c$, provided that D and D¹ are not both a bond;

A is aryl or heteroaryl, each of which is substituted with 0-3 occurrences of $R^d$;

each R¹ is independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$;

each $R^a$ and each $R^b$ are independently selected from hydrogen, $C_{1-4}$ alkyl, or $R^a$ and $R^b$ bound to the same carbon atom are taken together with the carbon atom to form a cycloalkyl;

each $R^c$ is independently selected from hydrogen and $C_{1-4}$alkyl;

each $R^d$ is independently selected from halo, halo $C_{1-4}$ alkyl, $C_{1-4}$ alkyl, nitro, cyano, —OH and O($C_{1-4}$ alkyl), or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$alkoxy and hydroxyl;

h is 1, 2 or 3;

each m is independently 1, 2 or 3; and each n is independently 0, 1, 2 or 3; provided that 1) D-Q-D¹-A is not i) O-benzyl, ii) $NHSO_2$-2-thiophenyl, iii) NHC(O)-optionally substituted phenyl, or iv) $NHSO_2$-optionally substituted phenyl; and 2) the compound is not:
i) N-(2,6-dimethylphenyl)-1,2,3,4-tetrahydro-1,3-dimethyl-2-oxo-6-Quinazolinesulfonamide;
ii) N-[2-[[[(1S)-2-cyclohexyl-1-methylethyl]amino]methyl]phenyl]-1,4-dihydro-2-oxo-2H-3,1-Benzoxazine-6-sulfonamide; or
iii) N-[2-[[[(1S)-2-cyclopentyl-1-methylethyl]amino]methyl]phenyl]-1,4-dihydro-2-oxo-2H-3,1-Benzoxazine-6-sulfonamide.

In certain embodiments of Formula (V), D is a bond.
In some embodiments of Formula (V), D is N($R^c$). In one aspect of these embodiments of Formula (V), $R^c$ is hydrogen.
In certain embodiments of Formula (V), D is a bond and $D^1$ is N($R^c$). In one aspect of this embodiment of Formula (V), Q is $SO_2$. In another aspect of these embodiments of Formula (V), Q is $SO_2$ and $D^1$ is NH. In another aspect of these embodiments of Formula (V), Q is C(O). In a more particular aspect of these embodiments of Formula (V), $D^1$ is NH and Q is C(O). In another aspect of these embodiments of Formula (V), Q is $(CH_2)_h$. In a more particular aspect of these embodiments of Formula (V), Q is $CH_2$. In another more particular aspect of these embodiments of Formula (V), $D^1$ is NH and Q is $(CH_2)_h$. In an even more particular aspect of these embodiments of Formula (V), $D^1$ is NH and Q is $CH_2$.
In some embodiments of Formula (V), $D^1$ is oxygen.
In some embodiments of Formula (V), D is a bond and $D^1$ is oxygen. In one aspect of these embodiments of Formula (V), Q is C(O).
In some embodiments of Formula (V), D is N($R^c$) and $D^1$ is oxygen. In one aspect of these embodiments of Formula (V), Q is C(O). In a more particular aspect of these embodiments of Formula (V), D is NH and Q is C(O).
In some embodiments of Formula (V), D is oxygen. In one aspect of these embodiments of Formula (V), Q is C(O) and $D^1$ is N($R^c$). In a more particular aspect of these embodiments of Formula (V), Q is C(O) and $D^1$ is NH.
In certain embodiments of Formula (V), Q is $SO_2$. In some embodiments of Formula (V), Q is $(CH_2)_h$. In one aspect of these embodiments of Formula (V), h is 1.
In some embodiments of Formula (V), Q is C(O).
In certain embodiments of Formula (V), $R^a$ is hydrogen.
In certain embodiments of Formula (V), $R^b$ is hydrogen.
In another aspect, the present invention includes a compound of Formula (V), wherein D is a bond, Q is $S(O)_2$ and $D^1$ is —NH—, the compound having the formula (Va):

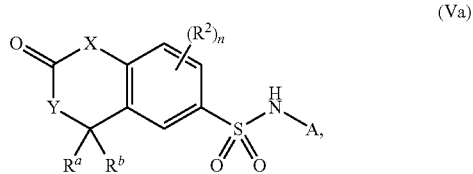

(Va)

wherein X, Y, L, $R^a$, $R^b$, $R^c$, $R^d$, $R^f$, $R^g$, $R^1$, $R^2$, A, n and m are as described for formula (V).

The following embodiments and aspects thereof relate to both formula (V) and formula (Va).

In certain embodiments of Formulas (V) and (Va), Y is N-L-$R^1$.
In some embodiments of Formulas (V) and (Va), Y is N-L-$R^1$ and L is a bond. In one aspect of these embodiments of Formulas (V) and (Va), $R^1$ is hydrogen. In another aspect of these embodiments of Formulas (V) and (Va), $R^1$ is $C_{1-4}$ alkyl substituted with 0-3 occurrences of $R^g$. In a more specific aspect of these embodiments of Formulas (V) and (Va), $R^1$ is $C_{1-4}$ alkyl substituted with 0 occurrences of $R^g$ (e.g., methyl).
In some embodiments of Formulas (V) and (Va), Y is N-L-$R^1$ and L is —$(CR^aR^b)_m$—. In a specific aspect of these embodiments of Formulas (V) and (Va), L is —$CR^aR^b$— (e.g., m is 1). In a more specific aspect of these embodiments of Formulas (V) and (Va), L is —$CH_2$— (e.g., $R^a$ and $R^b$ are hydrogen). In another aspect of these embodiments of Formulas (V) and (Va), $R^1$ is aryl substituted with 0-3 occurrences of $R^f$. In a more specific aspect of these embodiments of Formulas (V) and (Va), $R^1$ is aryl substituted with 0 occurrences of $R^f$. In an even more specific aspect of these embodiments of Formulas (V) and (Va), $R^1$ is unsubstituted phenyl.
In certain embodiments of Formulas (V) and (Va), X is O.
In certain embodiments of Formulas (V) and (Va), X is O and Y is N-L-$R^1$.
In certain embodiments of Formulas (V) and (Va), X is O, Y is N-L-$R^1$ and L is a bond. In one aspect of these embodiments of Formulas (V) and (Va), $R^1$ is hydrogen. In another aspect of these embodiments of Formulas (V) and (Va), $R^1$ is $C_{1-4}$ alkyl substituted with 0-3 occurrences of $R^g$. In a more specific aspect of these embodiments of Formulas (V) and (Va), $R^1$ is $C_{1-4}$ alkyl substituted with 0 occurrences of $R^g$ (e.g., methyl).
In certain embodiments of Formulas (V) and (Va), X is O and Y is N-L-$R^1$ and L is a —$(CR^aR^b)$—. In a specific aspect of these embodiments of Formulas (V) and (Va), L is —$CR^aR^b$— (e.g., m is 1). In a more specific aspect of these embodiments of Formulas (V) and (Va), L is —$CH_2$— (e.g., $R^a$ and $R^b$ are hydrogen). In another specific aspect of these embodiments of Formulas (V) and (Va), $R^1$ is $C_{1-4}$ alkyl substituted with 0-3 occurrences of $R^g$. In a more specific aspect of these embodiments of Formulas (V) and (Va), $R^1$ is $C_{1-4}$ alkyl substituted with 0 occurrences of $R^g$ (e.g., methyl). In another specific aspect of these embodiments of Formulas (V) and (Va), $R^1$ is aryl substituted with 0-3 occurrences of $R^f$. In a more specific aspect of these embodiments of Formulas (V) and (Va), $R^1$ is aryl substituted with 0 occurrences of $R^f$. In an even more specific aspect of these embodiments of Formulas (V) and (Va), $R^1$ is unsubstituted phenyl.
In certain embodiments of Formulas (V) and (Va), X is N-L-$R^1$.
In certain embodiments of Formulas (V) and (Va), X is N-L-$R^1$, and L is a bond. In one aspect of these embodiments of Formulas (V) and (Va), $R^1$ is hydrogen. In still another aspect of these embodiments of Formulas (V) and (Va), $R^1$ is $C_{1-4}$ alkyl substituted with 0-3 occurrences of $R^g$. In a more specific aspect of these embodiments of Formulas (V) and (Va), $R^1$ is $C_{1-4}$ alkyl substituted with 0 occurrences of $R^g$ (e.g., methyl).
In some embodiments of Formulas (V) and (Va), X is N-L-$R^1$, and L is —$(CR^aR^b)_m$—. In a specific aspect of these embodiments of Formulas (V) and (Va), L is —$CR^aR^b$— (e.g., m is 1). In an even more specific aspect of these embodiments of Formulas (V) and (Va), L is —$CH_2$— (e.g, $R^a$ and $R^b$ are hydrogen). In another specific aspect of these embodiments of Formulas (V) and (Va), $R^1$ is aryl substituted with 0-3 occurrences of $R^f$. In a more specific aspect of these embodiments of Formulas (V) and (Va), $R^1$ is unsubstituted phenyl.
In some embodiments of Formulas (V) and (Va), Y is O.
In some embodiments of Formulas (V) and (Va), Y is O and X is N-L-$R^1$.
In certain embodiments of Formulas (V) and (Va), X is N-L-$R^1$, Y is O and L is a bond. In one aspect of these embodiments of Formulas (V) and (Va), $R^1$ is hydrogen. In still another aspect of these embodiments of Formulas (V)

and (Va), $R^1$ is $C_{1-4}$ alkyl substituted with 0-3 occurrences of $R^g$. In a more specific aspect of these embodiments of Formulas (V) and (Va), $R^1$ is $C_{1-4}$ alkyl substituted with 0 occurrences of $R^g$ (e.g., methyl).

In some embodiments of Formulas (V) and (Va), X is N-L-$R^1$, Y is O and L is —$(CR^aR^b)_m$—. In a specific aspect of these embodiments of Formulas (V) and (Va), L is —$CR^aR^b$— (e.g., m is 1). In an even more specific aspect of these embodiments of Formulas (V) and (Va), L is —$CH_2$— (e.g, $R^a$ and $R^b$ are hydrogen). In another specific aspect of these embodiments of Formulas (V) and (Va), $R^1$ is aryl substituted with 0-3 occurrences of $R^f$. In a more specific aspect of these embodiments of Formulas (V) and (Va), $R^1$ is unsubstituted phenyl.

In certain embodiments of Formulas (V) and (Va), n is 0.

In certain embodiments of Formulas (V) and (Va), A is aryl (e.g., monocyclic or bicyclic aryl) substituted with 0-3 occurrences of $R^d$. In some embodiments of Formulas (V) and (Va), A is 5-8 membered monocyclic aryl (e.g., phenyl) substituted with 0-3 occurrences of $R^d$. In some embodiments of Formulas (V) and (Va), A is phenyl substituted with 0-3 occurrences of $R^d$.

In some embodiments of Formulas (V) and (Va), A is phenyl substituted with 2 occurrences of $R^d$. In certain embodiments of Formulas (V) and (Va), both $R^d$ are halo (e.g., 3-chloro-4-fluorophenyl). In some embodiments of Formulas (V) and (Va), one $R^d$ is alkyl and one $R^d$ is halo (e.g., 3-methyl-4-fluorophenyl).

In another aspect, the present invention includes a compound of formula (VI),

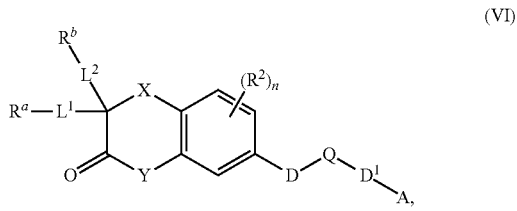

wherein

X and Y are each independently selected from O and N—$R^1$;

Q is C(O), $SO_2$, or —$(CH_2)_h$—;

$L^1$ and $L^2$ are each independently selected from a bond, —O—, C(O)—, —C(O)O—, —OC(O)—, —C(O)$NR^c$—, —$NR^cC(O)$—, —S—, —SO— and —$SO_2$—;

D and $D^1$ are each independently selected from a bond, O and $NR^c$, provided that D and $D^1$ are not both a bond;

A is aryl or heteroaryl, each of which is substituted with 0-3 occurrences of $R^f$;

each $R^1$ is independently selected from hydrogen or $C_{1-4}$ alkyl, wherein each $C_{1-4}$ alkyl is substituted with 0-3 occurrences of $R^f$;

$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or one of $R^a$ or $R^b$ is taken together with $R^1$ and the atoms to which they are respectively attached to form an optionally substituted five-membered heterocyclyl;

each $R^c$ is independently selected from hydrogen and $C_{1-4}$alkyl;

each $R^d$ is independently selected from halo, halo $C_{1-4}$ alkyl, $C_{1-4}$ alkyl, nitro, —$NR^cR^c$, —NHCH($NR^cR^c$) $NR^cR^{c'}$—NHC(=$NR^cR^c$)$NR^cR^c$, —C(O)$NR^cR^c$, cyano, —$SR^c$ and —$R^c$, or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$alkoxy and hydroxyl;

h is 1, 2 or 3; and n is 0, 1, 2 or 3; provided that

1) D-Q-$D^1$-A is not —$SO_3$-phenyl or —$SO_3$-p-methylphenyl;

2) when Y is $NR^c$, then Q is not C(O);

3) when Y is NH, D-Q-$D^1$- is not $SO_2NR^c$ or $NR^cSO_2$; and 4) the compound is not:

i) N-(3-fluoro-2-methylphenyl)-3,4-dihydro-4-methyl-3-oxo-2H-1,4-benzoxazine-6-sulfonamide;

ii) methyl 4,5-dimethoxy-2-(4-methyl-3-oxo-3,4-dihydro-2H-benzo[b][1,4]oxazine-6-sulfonamido)-phenethylcarbamate;

iii) 1-(difluoromethyl)-N-(3,4-dihydro-4-methyl-3-oxo-2H-1,4-benzoxazin-6-yl)-5-methyl-1H-pyrazole-4-sulfonamide;

iv) N-(3,4-dihydro-4-methyl-3-oxo-2H-1,4-benzoxazin-6-yl)-4-fluoro-3-methyl-benzenesulfonamide;

v) 7-chloro-N-(3,4-dihydro-4-methyl-3-oxo-2H-1,4-benzoxazin-6-yl)-2,3-dihydro-1,4-benzodioxin-6-sulfonamide;

vi) N-(3,4-dihydro-4-methyl-3-oxo-2H-1,4-benzoxazin-6-yl)-1,5-dimethyl-1H-pyrazole-4-sulfonamide;

vii) N-(3,4-dihydro-4-methyl-3-oxo-2H-1,4-benzoxazin-6-yl)-2-fluoro-5-methyl-benzenesulfonamide; or viii) 5-chloro-N-(3,4-dihydro-4-methyl-3-oxo-2H-1,4-benzoxazin-6-yl)-2,4-dimethoxy-benzenesulfonamide.

In certain embodiments of Formula (VI), D is a bond.

In some embodiments of Formula (VI), D is oxygen.

In some embodiments of Formula (VI), D is $NR^c$. In one aspect of these embodiments of Formula (VI), D is NH. In another aspect of these embodiments of Formula (VI), D is N($C_{1-4}$ alkyl). In a more specific aspect of these embodiments of Formula (VI), D is N($CH_3$).

In certain embodiments of Formula (VI), $D^1$ is O.

In certain embodiments of Formula (VI), $D^1$ is $NR^c$. In one aspect of these embodiments of Formula (VI), $D^1$ is NH. In a more specific aspect of these embodiments of Formula (VI), $D^1$ is N($C_{1-4}$ alkyl). In a more specific aspect of these embodiments of Formula (VI), $D^1$ is N($CH_3$).

In certain embodiments of Formula (VI), Q is $SO_2$.

In some embodiments of Formula (VI), Q is $(CH_2)_h$. In one aspect of these embodiments of Formula (VI), h is 1 (i.e., Q is $CH_2$).

In some embodiments of Formula (VI), Q is C(O).

In certain embodiments of Formula (VI), D is a bond, $D^1$ is $NR^c$ and Q is $SO_2$. In one aspect of these embodiments of Formula (VI), $D^1$ is NH. In another aspect of these embodiments of Formula (VI), $D^1$ is N($C_{1-4}$ alkyl). In a more specific aspect of these embodiments of Formula (VI), $D^1$ is N(CH$_3$).

In certain embodiments of Formula (VI), D is a bond, $D^1$ is NR$^c$ and Q is C(O). In one aspect of these embodiments of Formula (VI), $D^1$ is NH. In another aspect of these embodiments of Formula (VI), $D^1$ is ($C_{1-4}$ alkyl). In a more specific aspect of these embodiments of Formula (VI), $D^1$ is N(CH$_3$).

In certain embodiments of Formula (VI), D is a bond, $D^1$ is NR$^c$ and Q is (CH$_2$)$_h$. In one aspect of these embodiments of Formula (VI), h is 1. In one aspect of these embodiments of Formula (VI), $D^1$ is NH. In another aspect of these embodiments of Formula (VI), $D^1$ is N($C_{1-4}$ alkyl). In a more specific aspect of these embodiments of Formula (VI), $D^1$ is N(CH$_3$).

In certain embodiments of Formula (VI), D is oxygen, Q is C(O) and $D^1$ is NR$^c$. In one aspect of these embodiments of Formula (VI), $D^1$ is NH.

In certain embodiments of Formula (VI), D is NR$^c$, Q is C(O) and $D^1$ is oxygen. In one aspect of these embodiments of Formula (VI), D is NH. In another aspect of these embodiments of Formula (VI), D is N($C_{1-4}$ alkyl). In a more specific aspect of these embodiments of Formula (VI), D is N(CH$_3$).

In certain embodiments of Formula (VI), D is a bond, Q is C(O) and $D^1$ is oxygen.

In another embodiment, the present invention includes a compound of formula (VI), wherein D is a bond, Q is S(O)$_2$ and $D^1$ is —NH—, the compound having the formula (VIa):

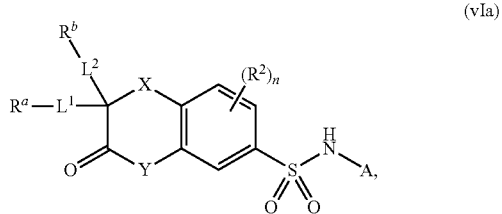
(VIa)

wherein X, Y, $R^a$, $R^b$, $R^c$, $R^d$, $R^f$, $R^g$, $L^1$, $L^2$, $R^1$, $R^2$, A and n are as described above.

The following embodiments and aspects thereof relate to both Formula (VI) and Formula (VIa).

In certain embodiments of Formulas (VI) and (VIa), X is O. In one aspect of these embodiments of Formulas (VI) and (VIa), Y is N—$R^1$. In a more specific aspect of these embodiments of Formulas (VI) and (VIa), Y is NH. In another aspect of these embodiments of Formulas (VI) and (VIa), Y is N($C_{1-4}$ alkyl), wherein the $C_{1-4}$ alkyl is substituted with 0-3 occurrences of $R^f$. In a more specific aspect of these embodiments of Formulas (VI) and (VIa), Y is N($C_{1-4}$ alkyl), wherein the alkyl is substituted with 0 occurrences of $R^f$. In an even more specific aspect of these embodiments of Formulas (VI) and (VIa), Y is N(CH$_3$).

In some embodiments of Formulas (VI) and (VIa), X is N—$R^1$. In one aspect of these embodiments of Formulas (VI) and (VIa), $R^1$ is hydrogen.

In some embodiments of Formulas (VI) and (VIa), Y is N—$R^1$. In one aspect of these embodiments of Formulas (VI) and (VIa), $R^1$ is hydrogen.

In certain embodiments of Formulas (VI) and (VIa), Y is O. In one aspect of these embodiments of Formulas (VI) and (VIa), X is N—$R^1$. In a more specific aspect of these embodiments of Formulas (VI) and (VIa), X is NH. In another aspect of these embodiments of Formulas (VI) and (VIa), X is N($C_{1-4}$ alkyl), wherein the $C_{1-4}$ alkyl is substituted with 0-3 occurrences of $R^f$. In a more specific aspect of these embodiments of Formulas (VI) and (VIa), X is N($C_{1-4}$ alkyl) wherein the alkyl is substituted with 0 occurrences of $R^f$. In a more specific aspect of these embodiments of Formulas (VI) and (VIa), X is N(CH$_3$).

In certain embodiments of Formulas (VI) and (VIa), n is 0.
In certain embodiments of Formulas (VI) and (VIa), n is 1.
In certain embodiments of Formulas (VI) and (VIa), $R^a$ is hydrogen.

In some embodiments of Formulas (VI) and (VIa), $R^b$ is hydrogen.

In certain embodiments of Formulas (VI) and (VIa), $L^1$ is a bond. In one aspect of this embodiment of Formulas (VI) and (VIa), $R^a$ is hydrogen.

In some embodiments of Formulas (VI) and (VIa), $L^2$ is a bond. In one aspect of this embodiment of Formulas (VI) and (VIa), $R^b$ is hydrogen.

In certain embodiments of Formulas (VI) and (VIa), A is aryl (e.g., monocyclic or bicyclic aryl) substituted with 0-3 occurrences of $R^d$. In one aspect of these embodiments of Formulas (VI) and (VIa), A is 5-8 membered monocyclic aryl (e.g., phenyl) substituted with 0-3 occurrences of $R^d$. In a more specific aspect of these embodiments of Formulas (VI) and (VIa), A is phenyl substituted with 0-3 occurrences of $R^d$. In an even more specific aspect of these embodiments of Formulas (VI) and (VIa), A is phenyl substituted with 0 occurrences of $R^d$.

In certain specific embodiments of Formulas (VI) and (VIa), A is phenyl substituted with 1 occurrence of $R^d$. In one aspect of these embodiments of Formulas (VI) and (VIa), $R^d$ is halo (e.g., p-fluorophenyl or m-chlorophenyl). In some embodiments of Formulas (VI) and (VIa), $R^d$ is alkyl (e.g., methyl). In another aspect of these embodiments of Formulas (VI) and (VIa), $R^d$ is —OR$^c$ (e.g., p-substituted —OR$^c$). In a more specific aspect of these embodiments of Formulas (VI) and (VIa), $R^d$ is p-substituted —OR$^c$. In another more specific aspect of these embodiments of Formulas (VI) and (VIa), $R^d$ is O-alkyl (e.g., —O-methyl).

In certain embodiments of Formulas (VI) and (VIa), A is phenyl substituted with 2 occurrences of $R^d$. In one aspect of these embodiments of Formulas (VI) and (VIa), both $R^d$ are halo (e.g., 3-chloro-4-fluorophenyl). In another aspect of these embodiments of Formulas (VI) and (VIa), both $R^d$ are alkyl (e.g., 3,5-dimethylphenyl). In another aspect of these embodiments of Formulas (VI) and (VIa), one $R^d$ is alkyl and one $R^d$ is halo (e.g., 3-methyl-4-fluorophenyl). In yet another aspect of these embodiments of Formulas (VI) and (VIa), two $R^d$, attached to the same or adjacent carbon atoms, taken together with the atoms to which they are attached form an optionally substituted heterocyclyl. In a more specific aspect of these embodiments of Formulas (VI) and (VIa), each $R^d$ is —OR$^c$ and the two —OR$^c$ taken together with the carbon atoms to which they are attached form an optionally substituted heterocyclyl. In another more specific aspect of these embodiments of Formulas (VI) and (VIa), two —OR$^c$ form 3,4-ethylenedioxy. In another even more specific aspect of these embodiments of Formulas (VI) and (VIa), two —OR$^c$ form 3,4-methylenedioxy.

In another aspect, the present invention includes a compound of formula (VII),

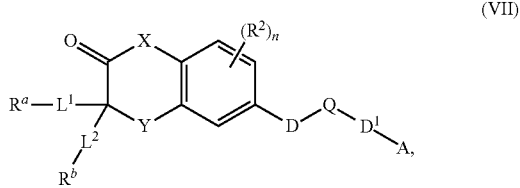
(VII)

wherein

X and Y are each independently selected from O and N—$R^1$;

Q is C(O), $SO_2$, or —$(CH_2)_h$—;

$L^1$ and $L^2$ are each independently selected from a bond, —O—, C(O)—, —C(O)O—, —OC(O)—, —C(O)$NR^c$—, —$NR^cC(O)$—, —S—, —SO— and —$SO_2$—;

D and $D^1$ are each independently selected from a bond, O and $NR^c$, provided that D and $D^1$ are not both a bond;

A is aryl or heteroaryl, each of which is substituted with 0-3 occurrences of $R^d$;

each $R^1$ is independently selected from hydrogen or $C_{1-4}$ alkyl; wherein each $C_{1-4}$ alkyl is substituted with 0-3 occurrences of $R^f$;

$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocloalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or one of $R^a$ or $R^b$ is taken together with a Y—$R^1$ or X—$R^1$ and the atoms to which they are respectively attached to form an optionally substituted five-membered heterocyclyl;

each $R^c$ is independently selected from hydrogen and $C_{1-4}$alkyl;

each $R^d$ is independently selected from halo, halo $C_{1-4}$ alkyl, $C_{1-4}$ alkyl, nitro, —$NR^cR^c$, —$NHCH(NR^cR^c)NR^cR^c$, —$NHC(=NR^cR^c)NR^cR^c$, —$C(O)NR^cR^c$, cyano, —$SR^c$ and —$OR^c$, or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$alkoxy and hydroxyl;

h is 1, 2 or 3; and n is 0, 1, 2 or 3; provided that:

1) D-Q-$D^1$-A is not O-benzyl;
2) when Y is O, X is not N—$R^1$; and
3) the compound of formula (IV) is not:
(E)-N-(3,3-dimethyl-2-oxo-3,4-dihydro-2H-benzo[b][1,4]oxazin-6-yl)-4-(3,3,3-trifluoroprop-1-en-1-yl)benzamide;
(E)-N-(3,3-dimethyl-2-oxo-3,4-dihydro-2H-benzo[b][1,4]oxazin-6-yl)-N-methyl-4-(3,3,3-trifluoroprop-1-en-1-yl)benz amide;
3-[2-(4-bromophenyl)-2-oxoethyl]-3,4-dihydro-6-methyl-2H-1,4-benzoxazin-2-one; or
4-[[(3,4-dihydro-2-oxo-2H-1,4-benzoxazin-6-yl)amino]sulfonyl]-5-methyl-2-furancarboxylic acid ethyl ester.

In certain embodiments of Formula (VII), D is a bond.

In some embodiments of Formula (VII), D is oxygen.

In some embodiments of Formula (VII), D is $NR^c$. In one aspect of these embodiments of Formula (VII), D is NH. In another aspect of these embodiments of Formula (VII), D is N($C_{1-4}$ alkyl). In a more specific aspect of these embodiments of Formula (VII), D is N($CH_3$).

In certain embodiments of Formula (VII), $D^1$ is O.

In certain embodiments of Formula (VII), $D^1$ is $NR^c$. In one aspect of these embodiments of Formula (VII), $D^1$ is NH. In a more specific aspect of these embodiments of Formula (VII), $D^1$ is N($C_{1-4}$ alkyl). In a more specific aspect of these embodiments of Formula (VII), $D^1$ is N($CH_3$).

In certain embodiments of Formula (VII), Q is $SO_2$.

In some embodiments of Formula (VII), Q is $(CH_2)_h$. In one aspect of these embodiments of Formula (VII), h is 1 (i.e., Q is $CH_2$).

In some embodiments of Formula (VII), Q is C(O).

In certain embodiments of Formula (VII), D is a bond, $D^1$ is $NR^c$ and Q is $SO_2$. In one aspect of these embodiments of Formula (VII), $D^1$ is NH. In another aspect of these embodiments of Formula (VII), $D^1$ is N($C_{1-4}$ alkyl). In a more specific aspect of these embodiments of Formula (VII), $D^1$ is N($CH_3$).

In certain embodiments of Formula (VII), D is a bond, $D^1$ is $NR^c$ and Q is C(O). In one aspect of these embodiments of Formula (VII), $D^1$ is NH. In another aspect of these embodiments of Formula (VII), $D^1$ is ($C_{1-4}$ alkyl). In a more specific aspect of these embodiments of Formula (VII), $D^1$ is N($CH_3$).

In certain embodiments of Formula (VII), D is a bond, $D^1$ is $NR^c$ and Q is $(CH_2)_h$. In one aspect of these embodiments of Formula (VII), h is 1. In one aspect of these embodiments of Formula (VII), $D^1$ is NH. In another aspect of these embodiments of Formula (VII), $D^1$ is N($C_{1-4}$ alkyl). In a more specific aspect of these embodiments of Formula (VII), $D^1$ is N($CH_3$).

In certain embodiments of Formula (VII), D is oxygen, Q is C(O) and $D^1$ is $NR^c$. In one aspect of these embodiments of Formula (VII), $D^1$ is NH.

In certain embodiments of Formula (VII), D is $NR^c$, Q is C(O) and $D^1$ is oxygen. In one aspect of these embodiments of Formula (VII), D is NH. In another aspect of these embodiments of Formula (VII), D is N($C_{1-4}$ alkyl). In a more specific aspect of these embodiments of Formula (VII), D is N($CH_3$).

In certain embodiments of Formula (VII), D is a bond, Q is C(O) and $D^1$ is oxygen.

In another aspect, the present invention includes a compound of formula (VII), wherein D is a bond, Q is $S(O)_2$ and $D^1$ is —NH—, the compound having the formula (VIIa):

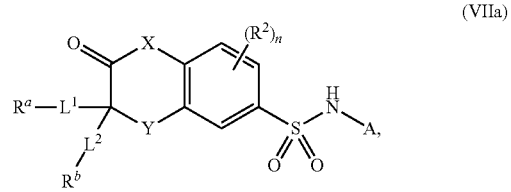

(VIIa)

wherein X, Y, $R^a$, $R^b$, $R^c$, $R^d$, $R^f$, $R^g$, $L^1$, $L^2$, $R^1$, $R^2$, A and n are as described above.

The following embodiments and aspects thereof relate to both Formula (VII) and Formula (VIIa).

In certain embodiments of Formulas (VII) and (VIIa), X is O. In one aspect of these embodiments of Formulas (VII) and (VIIa), Y is N—$R^1$. In a more specific aspect of these embodiments of Formulas (VII) and (VIIa), Y is NH. In another aspect of these embodiments of Formulas (VII) and (VIIa), Y is N($C_{1-4}$ alkyl), wherein the $C_{1-4}$ alkyl is substituted with 0-3 occurrences of $R^f$. In a more specific aspect of these embodiments of Formulas (VII) and (VIIa), Y is N($C_{1-4}$ alkyl, wherein the alkyl is substituted with 0 occurrences of $R^f$. In an even more specific aspect of these embodiments of Formulas (VII) and (VIIa), Y is N($CH_3$).

In some embodiments of Formulas (VII) and (VIIa), X is N—$R^1$. In one aspect of these embodiments of Formulas (VII) and (VIIa), $R^1$ is hydrogen.

In some embodiments of Formulas (VII) and (VIIa), Y is N—$R^1$. In one aspect of these embodiments of Formulas (VII) and (VIIa), $R^1$ is hydrogen.

In certain embodiments of Formulas (VII) and (VIIa), Y is O. In one aspect of these embodiments of Formulas (VII) and (VIIa), X is N—$R^1$. In a more specific aspect of these embodiments of Formulas (VII) and (VIIa), X is NH. In another aspect of these embodiments of Formulas (VII) and (VIIa), X is N($C_{1-4}$ alkyl), wherein the $C_{1-4}$ alkyl is substituted with 0-3 occurrences of $R^f$. In a more specific aspect of these embodiments of Formulas (VII) and (VIIa), X is N($C_{1-4}$ alkyl) wherein the alkyl is substituted with 0 occurrences of $R^f$. In a more specific aspect of these embodiments of Formulas (VII) and (VIIa), X is N($CH_3$).

In certain embodiments of Formulas (VII) and (VIIa), n is 0.

In certain embodiments of Formulas (VII) and (VIIa), n is 1.

In certain embodiments of Formulas (VII) and (VIIa), $R^a$ is hydrogen.

In some embodiments of Formulas (VII) and (VIIa), $R^b$ is hydrogen.

In certain embodiments of Formulas (VII) and (VIIa), $L^1$ is a bond. In one aspect of this embodiment of Formulas (VII) and (VIIa), $R^a$ is hydrogen.

In some embodiments of Formulas (VII) and (VIIa), $L^2$ is a bond. In one aspect of this embodiment of Formulas (VII) and (VIIa), $R^b$ is hydrogen.

In certain embodiments of Formulas (VII) and (VIIa), A is aryl (e.g., monocyclic or bicyclic aryl) substituted with 0-3 occurrences of $R^d$. In one aspect of these embodiments of Formulas (VII) and (VIIa), A is 5-8 membered monocyclic aryl (e.g., phenyl) substituted with 0-3 occurrences of $R^d$. In a more specific aspect of these embodiments of Formulas (VII) and (VIIa), A is phenyl substituted with 0-3 occurrences of $R^d$. In an even more specific aspect of these embodiments of Formulas (VII) and (VIIa), A is phenyl substituted with 0 occurrences of $R^d$.

In certain specific embodiments of Formulas (VII) and (VIIa), A is phenyl substituted with 1 occurrence of $R^d$. In one aspect of these embodiments of Formulas (VII) and (VIIa), $R^d$ is halo (e.g., p-fluorophenyl or m-chlorophenyl). In some embodiments of Formulas (VII) and (VIIa), $R^d$ is alkyl (e.g., methyl). In another aspect of these embodiments of Formulas (VII) and (VIIa), $R^d$ is —$OR^c$ (e.g., p-substituted —$OR^c$). In a more specific aspect of these embodiments of Formulas (VII) and (VIIa), $R^d$ is p-substituted —$OR^c$. In another more specific aspect of these embodiments of Formulas (VII) and (VIIa), $R^d$ is O-alkyl (e.g., —O-methyl).

In certain embodiments of Formulas (VII) and (VIIa), A is phenyl substituted with 2 occurrences of $R^d$. In one aspect of these embodiments of Formulas (VII) and (VIIa), both $R^d$ are halo (e.g., 3-chloro-4-fluorophenyl). In another aspect of these embodiments of Formulas (VII) and (VIIa), both $R^d$ are alkyl (e.g., 3,5-dimethylphenyl). In another aspect of these embodiments of Formulas (VII) and (VIIa), one $R^d$ is alkyl and one $R^d$ is halo (e.g., 3-methyl-4-fluorophenyl). In yet another aspect of these embodiments of Formulas (VII) and (VIIa), two $R^d$, attached to the same or adjacent carbon atoms, taken together with the carbon atoms to which they are attached form an optionally substituted heterocyclyl. In a more specific aspect of these embodiments of Formulas (VII) and (VIIa), each $R^d$ is —$OR^c$ and the two —$OR^c$ taken together with the carbon atoms to which they are attached form an optionally substituted heterocyclyl. In another more specific aspect of these embodiments of Formulas (VII) and (VIIa), two —$OR^c$ form 3,4-ethylenedioxy. In another even more specific aspect of these embodiments of Formulas (VII) and (VIIa), two —$OR^c$ form 3,4-methylenedioxy.

In another embodiment, the present invention includes a pharmaceutically acceptable salt of a compound of formulas (IV), (V), (VI) or (VII). In another aspect, the present invention includes a pharmaceutically acceptable salt of a compound of formulas (IVa), (Va), (VIa) or (VIIa).

In another embodiment, the present invention includes a composition (e.g., a pharmaceutical composition) comprising a compound of formulas (IV), (V), (VI) or (VII). In some embodiments, the composition further comprises a pharmaceutically acceptable carrier. In another aspect, the present invention includes a composition (e.g., a pharmaceutical composition) comprising a compound of formulas (IVa), (Va), (VIa) or (VIIa).

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to NH(alkyl) and NH(alkyl)$_2$ radicals respectively. The term "aralkylamino" refers to a NH(aralkyl) radical. The term alkylaminoalkyl refers to a (alkyl)NH-alkyl- radical; the term dialkylaminoalkyl refers to a (alkyl)$_2$N-alkyl- radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The terms "hetaralkyl" and "heteroaralkyl", as used herein, refers to an alkyl group substituted with a heteroaryl group.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "activator" as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that activate mutant PKRs (for example, specific PKR mutants as those described herein) and/or wild type PKR.

In one aspect, exemplary compounds include the compounds of formula (I), formula (I-II), formula (I-III), and formula (I-IV) described in the International Patent Publication WO2010/129596 (published Nov. 11, 2010), the content of which is hereby incorporated by reference in its entirety, and for example, in Table 1 of the International Patent Publication WO2010/129596.

In another aspect, exemplary compounds include the compounds of formula (II), formula (II-II), formula (II-III), formula (II-IV), formula (II-V), formula (II-VI) and formula (II-VII) described in the International Patent Publication WO2010/118063 (published Oct. 14, 2010), the content of which is hereby incorporated by reference in its entirety, and for example, in Table 1 of the International Patent Publication WO2010/118063.

In another aspect, exemplary compounds include the compounds of formula (III), formula (III-II), formula (III-III), and formula (III-IV) described in the International Patent Publication WO2011/002816 (published Jan. 6, 2011), the content of which is hereby incorporated by reference in its entirety, and for example, in Table 1 of the International Patent Publication WO2011/002816.

In another aspect, exemplary compounds include compounds of formula (IV), formula (V), formula (VI) and formula (VII), such as those described in Tables A-D below.

TABLE A

| Compound |
| --- |
| *structure* |
| *structure* |

TABLE B

| Compound |
| --- |
| *structure* |
| *structure* |
| *structure* |

TABLE B-continued

| Compound |
| --- |
| *structure* |
| *structure* |

TABLE C

| Compound |
| --- |
| *structure* |
| *structure* |
| *structure* |
| *structure* |
| *structure* |

TABLE C-continued
Compound
TABLE D
Compound
The compounds described herein can be made using a variety of synthetic techniques, such as those described in the International Patent Publications WO2010/129596, WO2010/118063 and WO2011/002816 (the content of which is hereby incorporated herein by reference) and Schemes and Examples depicted below.
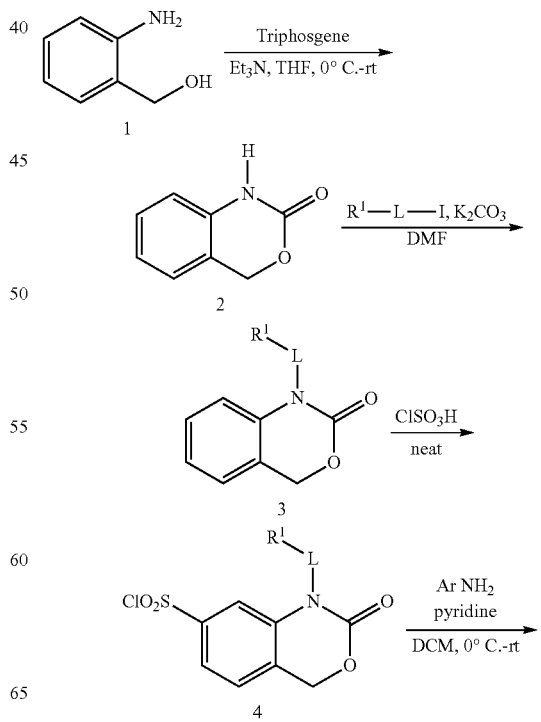
Scheme 1.

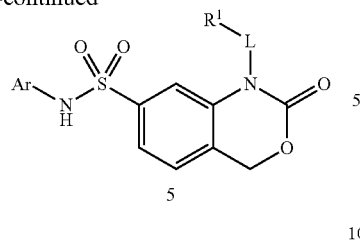

Scheme 1 above is an exemplary scheme that depicts a representative synthesis of certain compounds described herein. Aniline 1 is reacted with triphosgene and base to produce bicycle 2. Treatment of 2 with the appropriate halide and base generates the alkylated bicycle (3). Reaction of 3 with chlorosulfonic acid provided sulfonyl chloride 4. Treatment of 4 with the appropriate aniline provides the target molecule (5).

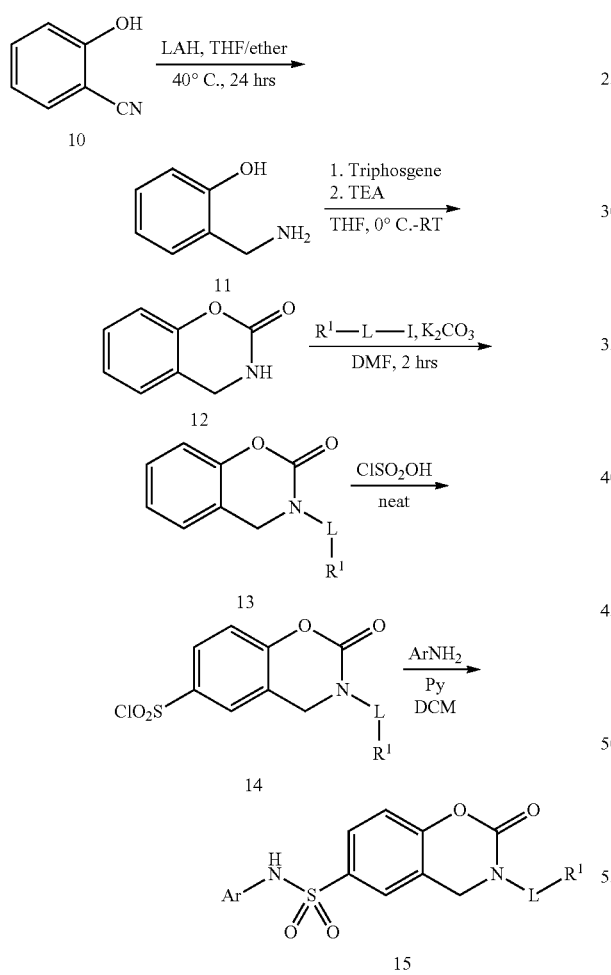

Scheme 2 above is an exemplary scheme that depicts a representative synthesis of certain compounds described herein. Cyanophenol (10) is reacted lithium aluminum hydride to provide aniline 11. Aniline 11 is treated with triphosgene and base to produce bicycle 12. Treatment of 12 with the appropriate halide and base generates the alkylated bicycle (13). Reaction of 13 with chlorosulfonic acid provided sulfonyl chloride 14. Treatment of 14 with the appropriate aniline provides the target molecule (15).

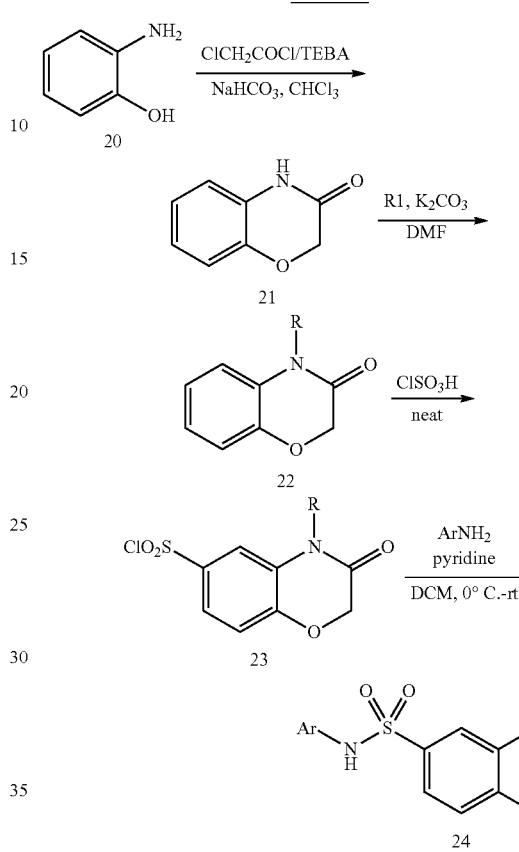

Scheme 3 above is an exemplary scheme that depicts a representative synthesis of certain compounds described herein. Aniline 20 is reacted with TEBA, chloroacetyl chloride and base to produce bicycle 21. Treatment of 21 with the appropriate halide and base generates the alkylated bicycle (22). Reaction of 22 with chlorosulfonic acid provided sulfonyl chloride 23. Treatment of 23 with the appropriate aniline provides the target molecule (24).

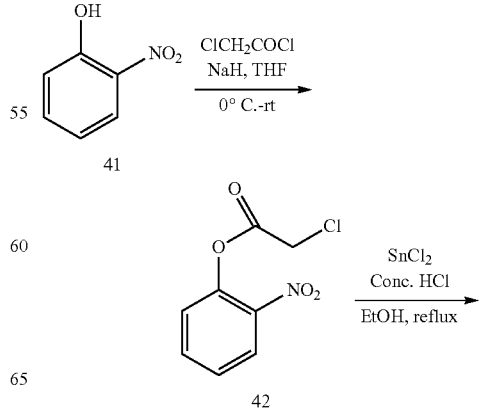

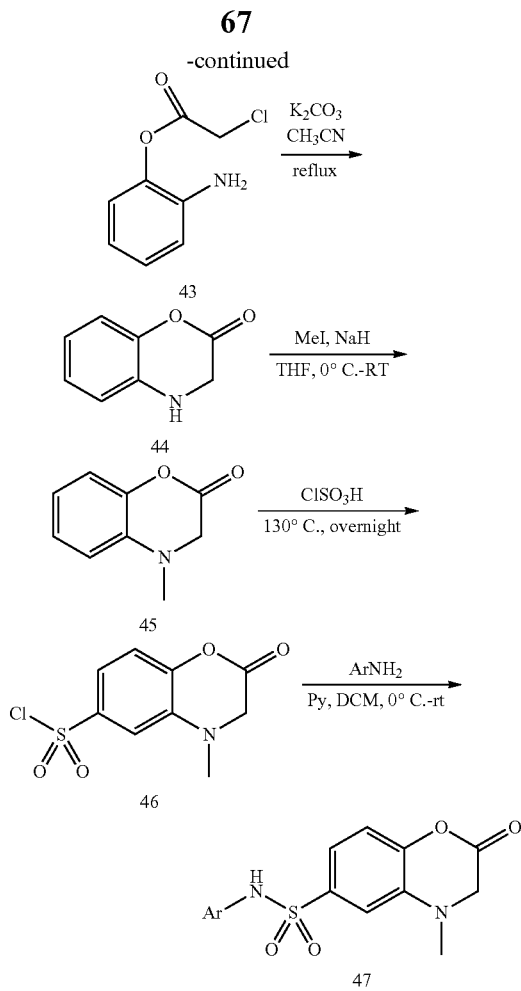

Scheme 4 above is an exemplary scheme that depicts a representative synthesis of certain compounds described herein. Phenol 41 is reacted with chloroacetyl chloride and base to produce 42. Treatment of 43 with Tin chloride in acid yielded the desired aniline (43). Treatment of aniline 43 with base produced bicycle 44. Reaction of 44 with the appropriate halide and base generates the alkylated bicycle (45). Reaction of 45 with chlorosulfonic acid provided sulfonyl chloride 46. Treatment of 46 with the appropriate aniline provides the target molecule (47).

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention.

The compounds provided herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$ and $^{14}C$; O may be in any isotopic form, including $^{16}O$ and $^{18}O$; and the like.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Certain activator compounds useful as PKR wild type and/or mutant activators are those that demonstrate specificity and activation of PKR enzyme (wild type and/or mutant) in the absence of FBP to a level greater than that of 10, 15, 20, 25, 30, 35, 40, 45, 50, 55, 60, 65, 70, 75, 80, 85, 90, 95, 99, or 100% in the presence of FBP.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkyl cyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

Example 1

PKR Mutant Assay

Procedure:
  PKR or PKR mutant enzyme solution was diluted in assay buffer.
  2 µL of test compound was added into wells first, and then 180 µL reaction mix was added.
  Reactions mixture with test compound was assembled except for ADP, and plates were stored for 60 minutes at room temperature.
  20 uL ADP was added to start reaction at room temperature and reaction progress was measured as changes in absorbance at 340 nm wavelength at room temperature.
Test Compound Preparation:
  Test compound stock was made at 100× concentration in 100% DMSO (10 mM)
  1 to 3 dilutions were made for 11 points (i.e. 50 µl of first concentration added to 100 µl 100% DMSO to yield 3.33 mM, 50 µl of this added to 100 µl DMSO to yield 1.11 mM, and so forth)
  1 to 100 dilution into assay (2 µl in 200 µl) yielded starting concentration of 100 µM, decreasing 3 fold for 11 points.
Assay Buffer:
  100 mM KCl, 50 mM Tris 7.5, 5 mM MgCl2, 1 mM DTT, 0.03% BSA
Reaction Mixture:
  PKR mutant enzyme: 80-400 ng/well; ADP: 0.22-1.65 mM; PEP: 0.1-0.5 mM; NADH: 180 uM; LDH: 0.5 units (Sigma#59023); DTT: 1 mM; BSA: 0.03%.
PKR Wide Type Single Point Percent Activation Assay
  A compound described herein was diluted with DMSO and tested at 1 µM concentration. The enzyme was diluted in 1× Buffer: (100 mM KCl, 50 mM Tris 7.5, 5 mM $MgCl_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final Concentration:
  PKR wt (100 ng/well), Tris pH 7.5 (50 mM), KCl (100 mM), $MgCl_2$ (5 mM), ADP (0.48 mM), PEP (0.15 mM), NADH (180 µM), LDH (0.5 units, Sigma 59023), DTT (1 mM) and BSA (0.03%).
PKR R510Q Single Point Percent Activation Assay
  A compound described herein was diluted with DMSO and tested at 1 µM concentration. The enzyme was diluted in 1× Buffer: (100 mM KCl, 50 mM Tris 7.5, 5 mM $MgCl_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final Concentration:
  PKR R510Q (40 ng/well), Tris pH 7.5 (50 mM), KCl (100 mM), $MgCl_2$ (5 mM), ADP (0.2 mM), PEP (0.11 mM), NADH (180 µM), LDH (0.5 units, Sigma 59023), DTT (1 mM) and BSA (0.03%).
PKR R532W Single Point Percent Activation Assay
  A compound described herein was diluted with DMSO and tested at 1 µM concentration. The enzyme was diluted in 1×

Buffer: (100 mM KCl, 50 mM Tris 7.5, 5 mM MgCl$_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:
PKR R532W (100 ng/well), Tris pH 7.5 (50 mM), KCl (100 mM), MgCl2 (5 mM), ADP (0.36 mM), PEP (0.1 mM), NADH (180 μM), LDH (0.5 units, Sigma 59023), DTT (1 mM) and BSA (0.03%).

PKR T384W Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl$_2$, 1 mM DTT, 0.03% BSA). 2 μL of compound solution was first added into wells, and then 180 μL enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:
PKR T384W soluble (300 ng/well), Tris pH 7.5 (50 mM), KCl (100 mM), MgCl2 (5 mM), ADP (0.08 mM), PEP (0.23 mM), NADH (180 μM), LDH (0.5 units, Sigma 59023), DTT (1 mM) and BSA (0.03%).

Representative compounds of formula (I), formula (I-II), formula (I-III), and formula (I-IV) were tested to be activators of wild type PKR, PKRR532W, PKRR479H, and PKRG332S with an AC$_{50}$ less than 800 nM against each wild type/mutant enzyme.

A representative compound of formula (II), formula (II-II), formula (II-III), formula (II-IV), formula (II-V), formula (II-VI) and formula (II-VII) was tested to be an activator of wild type PKR, PKRR532W, PKRR479H, and PKRG332S with an AC50 less than 600 nM against each wild type/mutant enzyme.

The activation activities against PKR wild type and mutants of other exemplary are shown in Table A below. As shown in Table A, A refers to a compound that has a % activation at 1 μM of from 1 to 100. B refers to a compound that has a % activation at 1 μM of from 101 to 500. C refers to a compound that has a % activation at 1 μM of greater than 500.

TABLE A

| Structure | % Act. R510Q | % Act. R532W | % Act. T384W | % Act. WT |
|---|---|---|---|---|
| | B | B | B | B |
| | B | B | B | B |
| | B | B | B | B |
| | B | A | A | A |

TABLE A-continued

| Structure | % Act. R510Q | % Act. R532W | % Act. T384W | % Act. WT |
|---|---|---|---|---|
| (benzyl-dihydroquinoxalinone sulfonamide with 3-F phenyl) | B | B | B | B |
| (N-methyl benzyl-dihydroquinoxalinone sulfonamide with 3-F phenyl) | B | B | B | B |
| (benzyl-benzoxazinone sulfonamide with 3-F phenyl) | B | A | B | B |

Example 2

Compounds of Formulae (IV), (V), (VI) and (VII) and their Preparation

Scheme 5:

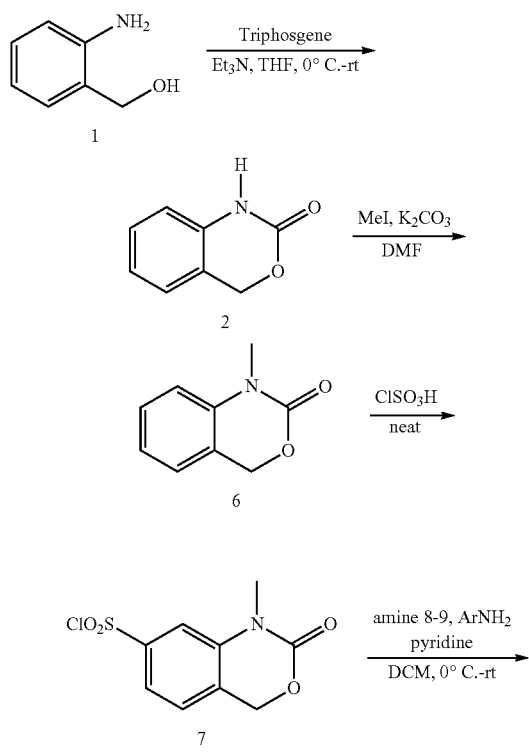

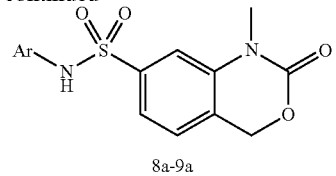

TABLE 5

| Amine | Ar = | Product |
|---|---|---|
| 8 | 3-Cl, 4-F phenyl | 8a |
| 9 | 3-Me, 4-F phenyl | 9a |

General Procedure for Compound 2:

To a solution of starting material 1 (1.5 gm, 12.10 mmoles) in dry THF, triphosgene (4.3 gm, 14.6 mmoles) in THF was added slowly at 0° C. The resulting mixture was allowed to stir at the same temperature for 10 min. Triethyl amine (6.1 mL, 42.6 mmoles) was then added dropwise at 0° C. and the reaction mixture was allowed to stir at room temperature for another 30 min. After completion of reaction, the reaction mixture was added to crushed ice and extracted with ethyl acetate and water. The organic layer was dried over $Na_2SO_4$ and concentrated under reduced pressure to afford solid product 2 in 66.66% yield (1.81 gm).

General Procedure for Compound 6:

To a solution of compound 2 (3.0 gm, 20.1 mmol) in DMF, potassium carbonate (8.3 gm, 60.4 moles) was added followed by methyl iodide (2 mL, 30.1 mmol) at room temperature. The resulting mixture was stirred for 2 hrs at the same temperature. After completion of the reaction, the mixture was washed with ethylacetate and water and the organic layer was dried over $Na_2SO_4$ and concentrated under reduced pressure to obtain a residue which turned into a solid compound 6 (2.5 gm, 78.12% yield) on washing with pentane solvent. The obtained product was used for further step directly without purification.

General Procedure for Compound 7:

Compound 6 (3.0 gm, 20.13 mmol) was added to a stirred solution of chlorosulfonic acid (6 mL/gm starting material) at 0° C. and the resulting solution was allowed to stir for 2 hrs at room temperature. After completion of reaction, the mixture was poured into ice cold water and added EtOAc and extracted. The aqueous layer was washed with EtOAc (2×50 ml) and the combined organic layer was washed with brine, dried over $Na_2SO_4$ and concentrated under reduced pressure to obtain a crude residue. The residue was washed with n-hexane to get a solid compound 7 (3.2 gm, 65.30% yield) which was pure enough for the next reaction.

Synthesis of Compound 8a:

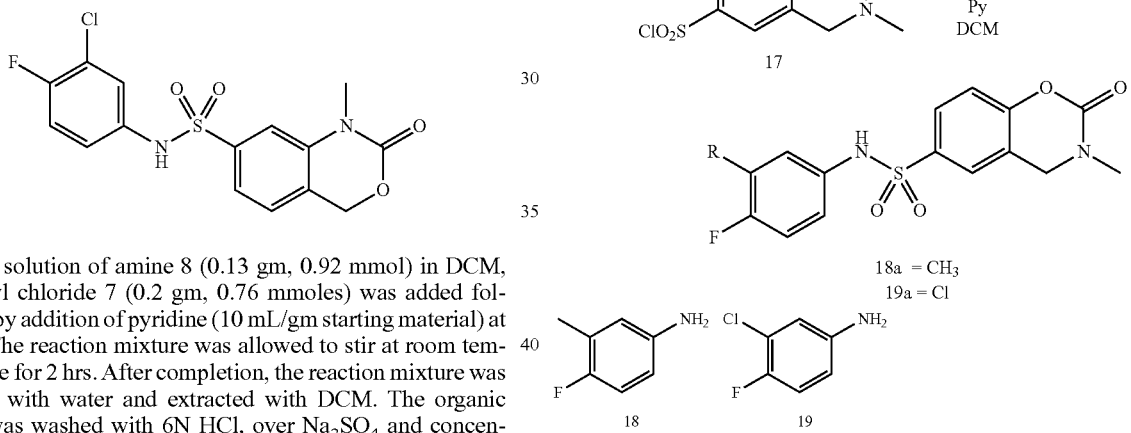

To a solution of amine 8 (0.13 gm, 0.92 mmol) in DCM, sulfonyl chloride 7 (0.2 gm, 0.76 mmoles) was added followed by addition of pyridine (10 mL/gm starting material) at 0° C. The reaction mixture was allowed to stir at room temperature for 2 hrs. After completion, the reaction mixture was diluted with water and extracted with DCM. The organic layer was washed with 6N HCl, over $Na_2SO_4$ and concentrated under reduced pressure to afford product 8a in 70% yield (0.28 gm).

$^1$H NMR (400 MHz, DMSO-$d_6$) δ 3.21 (s, 3H), 5.31 (s, 1H), 7.04 (br s, 1H), 7.20-7.35 (3H), 7.75-7.68 (m, 2H), 10.45 (s, 1H); MS: 369 (M−1 peak).

Synthesis of Compound 9a:

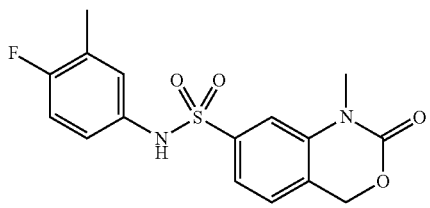 [SMILES: Cc1cc(NS(=O)(=O)c2ccc3c(c2)N(C)C(=O)OC3)ccc1F]

The synthesis of compound 9a was done from compound 7 (0.2 gm, 0.76 mmol) by following the similar procedure carried out to synthesize compound 8a mentioned above by using amine 9 in 74% yield (0.27 gm).

$^1$H NMR (500 MHz, DMSO-$d_6$) δ 2.18 (s, 3H), 3.22 (s, 3H), 5.30 (s, 2H), 6.89 (br s, 1H), 6.99 (d, 2H), 7.21 (d, 1H), 7.72-7.65 (m, 2H), 10.18 (s, 1H); MS: 349 (M−1 peak).

Scheme 6:

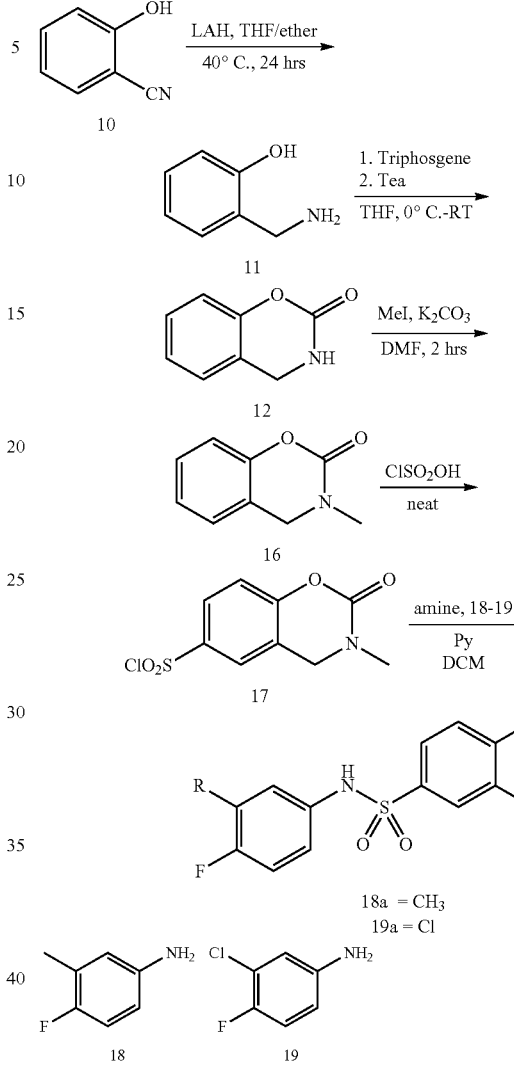

General Procedure for Compound 11:

To a solution of 2-cyano phenol 10 (0.2 gm, 0.075 mmoles) in a dry solvent mixture of THF and ether, $LiAlH_4$ (0.13 gm, 0.018 mmoles) was added at 0° C. portion wise. The resulting mixture was allowed to stir at room temperature for 30 min followed by stirring at 40° C. for 24 hrs. After completion of reaction, the mixture was quenched with saturated $NH_4Cl$ solution and extracted with ethyl acetate and water. The organic layer was dried over $Na_2SO_4$ and concentrated under reduced pressure to obtain product 11 as a solid in 75% yield. (0.2 gm).

General Procedure for Compound 12:

To a solution of starting material 11 (0.1 gm, 0.081 mmoles) in dry THF, triphosgene (0.29 gm, 0.098 mmoles) was added at 0° C. slowly. The resulting mixture was allowed to stir at the same temperature for 10 min followed by addition of triethyl amine drop wise. The reaction mixture was allowed warm to at room temperature and stirred for 30 min. After completion of reaction, the reaction mixture was added to ice and extracted with ethyl acetate and water. The organic layer was dried over $Na_2SO_4$ and concentrated under reduced pressure to obtain product 12 as a solid (0.1 gm, 81.96% yield).

General Procedure for Compound 16:

To a solution of compound 12 (3.0 gm, 20.1 mmol) in DMF, potassium carbonate (8.3 gm, 60.4 moles) was added followed by methyl iodide (2 mL, 30.1 mmol) at room temperature. The resulting mixture was stirred for 2 hrs at the same temperature. After completion of the reaction, the mixture was washed with ethylacetate and water and the organic layer was dried over $Na_2SO_4$ and concentrated under reduced pressure to obtain a residue which turned into a solid compound 16 (2.5 gm, 78.12% yield) on washing with pentane solvent. The obtained product was used for further step directly without purification.

General Procedure for Compound 17:

Compound 16 (3.0 gm, 20.13 mmol) was added to a stirred solution of chlorosulfonic acid (6 mL/gm starting material) at 0° C. and the resulting solution was allowed to stir for 2 hrs at room temperature. After completion of reaction, the mixture was poured into ice cold water and added EtOAc and extracted. The aqueous layer was washed with EtOAc (2×50 ml) and the combined organic layer was washed with brine, dried over $Na_2SO_4$ and concentrated under reduced pressure to obtain a crude residue. The residue was washed with n-hexane to get a solid compound 17 (3.2 gm, 65.30% yield) which was pure enough for the next reaction.

Synthesis of Compound 18a:

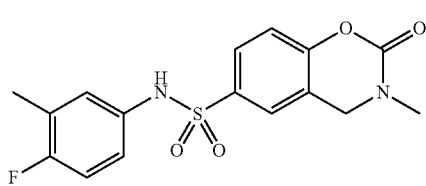 [SMILES: Cc1cc(NS(=O)(=O)c2ccc3c(c2)CN(C)C(=O)O3)ccc1F]

To a solution of amine 18 (0.13 gm, 0.92 mmol) in DCM, sulfonyl chloride 17 (0.2 gm, 0.76 mmoles) was added followed by addition of pyridine (10 mL/gm starting material) at 0° C. The reaction mixture was allowed to stir at room temperature for 2 hrs. After completion, the reaction mixture was diluted with water and extracted with DCM. The organic layer was washed with 6N HCl, over $Na_2SO_4$ and concentrated under reduced pressure to afford product 18a in 74% yield (0.2 gm).

$^1$H NMR (400 MHz, DMSO-$d_6$) δ 2.16 (s, 3H), 2.98 (s, 3H), 4.53 (s, 2H), 6.88 (br s, 1H), 7.02-6.98 (m, 3H), 7.19 (d, 1H), 7.61 (s, 2H), 10.19 (s, 1H); MS: 349 (M−1 peak).

Synthesis of Compound 19a:

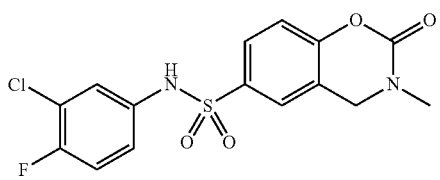 [SMILES: CN1Cc2cc(S(=O)(=O)Nc3ccc(F)c(Cl)c3)ccc2OC1=O]

The synthesis of compound 19a was done from compound 17 (0.2 gm, 0.76 mmol) by following the similar procedure mentioned for compound 19a in scheme 1 in 71% yield (0.2 gm).

$^1$H NMR (500 MHz, DMSO-$d_6$) δ 2.98 (s, 3H), 4.55 (s, 2H), 7.06 (br s, 1H), 7.29-7.20 (m, 2H), 7.35 (t, 1H), 7.65 (t, 2H), 10.52 (s, 1H); MS: 369 (M−1 peak).

Scheme 7:

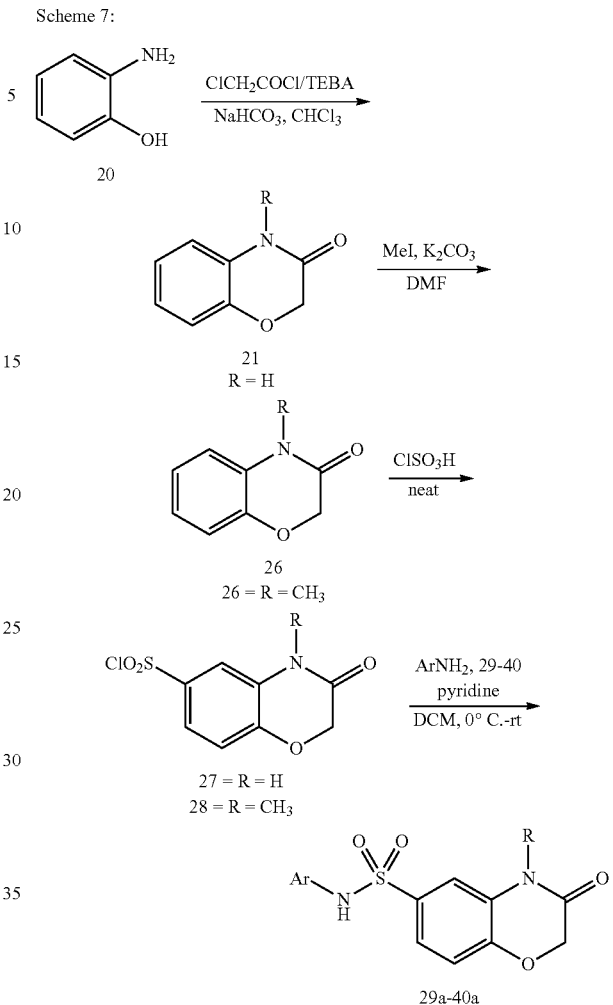

TABLE 6

| Amine | Ar = | R = | Product |
|---|---|---|---|
| 29 | benzo[1,4]dioxin-6-yl | $CH_3$ | 29a |
| 30 | 3,5-dimethylphenyl | $CH_3$ | 30a |
| 31 | 4-fluorophenyl | $CH_3$ | 31a |
| 32 | 4-methoxyphenyl | $CH_3$ | 32a |

TABLE 6-continued

| Amine | Ar = | R = | Product |
|---|---|---|---|
| 33 | 3-methyl-4-fluorophenyl | CH₃ | 33a |
| 34 | 3-chloro-4-fluorophenyl | CH₃ | 34a |
| 35 | 3-chlorophenyl | CH₃ | 35a |
| 36 | benzo[1,3]dioxol-5-yl | CH₃ | 36a |
| 37 | 3,5-dimethylphenyl | H | 37a |
| 38 | 4-fluorophenyl | H | 38a |
| 39 | 2,3-dihydrobenzo[1,4]dioxin-6-yl | H | 39a |
| 40 | 4-methoxyphenyl | H | 40a |

General Procedure for Compound 21:

To a solution of 2-amino phenol 20 (3.0 gm, 27.5 mmoles) in chloroform, TEBA (3.1 gm, 13.7 mmol) and NaHCO₃ was added at 0° C. Then a solution of chloro acetyl chloride (4.6 gm, 41.2 m moles) in chloroform was added over 20 minutes at the same temperature and the resulting mixture was allowed to stir at 60° C. for 16 hrs. After completion of the reaction, solvent was evaporated and washed with DCM and water. The organic layer was dried over Na₂SO₄ and concentrated under vacuum. The resulting solution was washed with pentane and ether as a co-solvent to get compound 21 (3.2 gm, 78.04% yield) as solid which was pure enough to use directly for further reaction.

General Procedure for Compound 26:

To a solution of compound 21 (3.0 gm, 20.1 mmol) in DMF, potassium carbonate (8.3 gm, 60.4 moles) was added followed by methyl iodide (2 mL, 30.1 mmol) at room temperature. The resulting mixture was stirred for 2 hrs at the same temperature. After completion of the reaction, the mixture was washed with ethylacetate and water and the organic layer was dried over Na₂SO₄ and concentrated under reduced pressure to obtain a residue which turned into a solid compound 26 (2.5 gm, 78.12% yield) on washing with pentane solvent. The obtained product was used for further step directly without purification.

General Procedure for Compound 27:

Compound 26 (3.0 gm, 20.13 mmol) was added to a stirred solution of chlorosulfonic acid (6 mL/gm starting material) at 0° C. and the resulting solution was allowed to stir for 2 hrs at room temperature. After completion of reaction, the mixture was poured into ice cold water and added EtOAc and extracted. The aqueous layer was washed with EtOAc (2×50 ml) and the combined organic layer was washed with brine, dried over Na₂SO₄ and concentrated under reduced pressure to obtain a crude residue. The residue was washed with n-hexane to get a solid compound 27 (3.2 gm, 65.30% yield) which was pure enough for the next reaction.

General Procedure for Compound 28:

Starting material 26 (2.0 gm, 12.2 mmol) was added to a stirred solution of chlorosulfonic acid (6 mL/gm starting material) at 0° C. and the resulting solution was allowed to stir for 2 hrs at room temperature. After completion of reaction, mixture was poured into ice cold water and added ethylacetate and extracted. The aqueous layer was washed with EtOAc (2×50 ml) and the combined organic layers was washed with brine and dried over Na₂SO₄ and concentrated under reduced pressure to obtain residue. The residue was washed with n-hexane to get solid compound 28 (2.5 gm, 78.1% yield). Thus obtained product was used for further step directly.

Synthesis of Compound 29a:

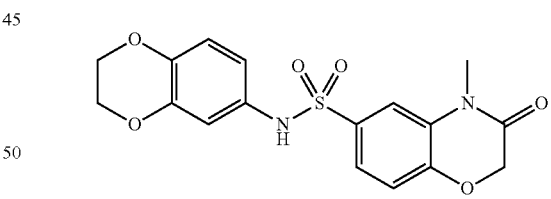

To a solution of amine 29 (0.07 gm, 0.463 mmol) in DCM, sulfonyl chloride 28 (0.14 gm, 0.35 mmoles) was added followed by pyridine (10 mL/gm starting material) at 0° C. and the reaction mixture was allowed to stir at room temperature for 2 hrs. After completion, the reaction mixture was diluted with water and extracted with DCM. The organic layer was washed with 6N HCl and dried over Na₂SO₄ and concentrated under reduced pressure to obtain product 29a (0.10 gm, 58.8% yield).

$^1$H NMR (500 MHz, DMSO-d$_6$) δ 3.21 (s, 3H), 4.19 (s, 4H), 4.78 (s, 2H), 6.58 (d, 1H), 6.6 (s, 1H), 6.71 (d, 1H), 7.15 (d, 1H), 7.34 (d, 1H), 7.29 (s, 1H), 9.83 (s, 1H). MS: 375 (M−1 peak).

Synthesis of Compound 30a:

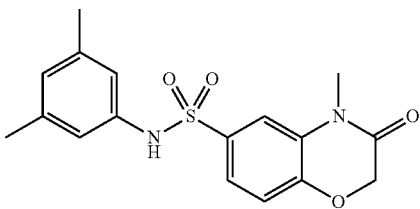 [SMILES: Cc1cc(C)cc(NS(=O)(=O)c2ccc3c(c2)N(C)C(=O)CO3)c1]

The synthesis of compound 30a was done by following the similar procedure as mentioned for compound 29a by using amine 30 to afford product 30a in 60% yield (0.12 gm) from compound 28 (0.18 gm, 0.69 mmoles).

$^1$H NMR (500 MHz, DMSO-d$_6$) δ 2.18 (s, 6H), 3.21 (s, 3H), 4.78 (s, 2H), 6.65 (s, 1H), 6.78 (s, 2H), 7.15 (d, 1H), 7.39 (d, 1H), 7.41 (s, 1H), 10.08 (s, 1H); MS: 345 (M−1 peak).

Synthesis of Compound 31a:

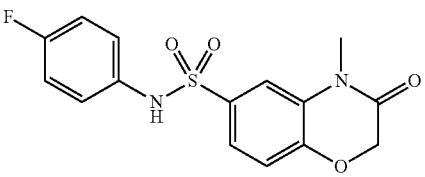 [SMILES: CN1C(=O)COc2ccc(S(=O)(=O)Nc3ccc(F)cc3)cc21]

The synthesis of compound 31a was done by following the similar procedure as mentioned for compound 29a by using amine 31 to afford product 31a in 61.1% yield (0.13 gm) from compound 28 (0.2 gm, 0.76 mmol).

$^1$H NMR (500 MHz, DMSO-d$_6$) δ 3.21 (s, 3H), 4.78 (s, 2H), 7.15-7.04 (m, 5H), 7.35 (d, 1H), 7.39 (s, 1H), 10.10 (s, 1H); MS: 335 (M−1 peak).

Synthesis of Compound 32a:

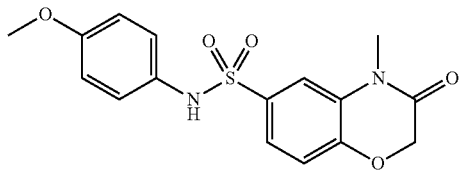 [SMILES: COc1ccc(NS(=O)(=O)c2ccc3c(c2)N(C)C(=O)CO3)cc1]

The synthesis of compound 32a was done by following the similar procedure as mentioned for compound 29a by using amine 32 to afford product 32a in 63.15% yield (0.12 gm) from compound 28 (0.18 gm, 0.68 mmol).

$^1$H NMR (500 MHz, DMSO-d$_6$) δ 3.20 (s, 3H), 3.66 (s, 3H), 4.78 (s, 2H), 6.81 (d, 2H), 7.01 (d, 2H), 7.09 (d, 1H), 7.29 (dd, 1H), 7.35 (d, 1H), 9.81 (s, 1H); MS: 349 (M+1 peak).

Synthesis of Compound 33a:

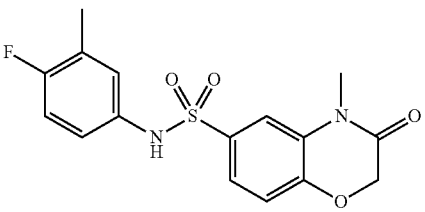 [SMILES: Cc1cc(NS(=O)(=O)c2ccc3c(c2)N(C)C(=O)CO3)ccc1F]

The synthesis of compound 33a was done by following the similar procedure as mentioned for compound 29a by using amine 33 to afford product 33a in 53% yield (0.15 gm) from compound 28 (0.25 gm, 0.96 mmol).

$^1$H NMR (400 MHz, DMSO-d$_6$) δ 2.16 (s, 3H), 3.21 (s, 3H), 4.75 (s, 3H), 6.91 (br s, 7.14-6.90 (m, 4H), 7.40-7.32 (m, 2H), 10.15 (s, 1H).

Synthesis of Compound 34a:

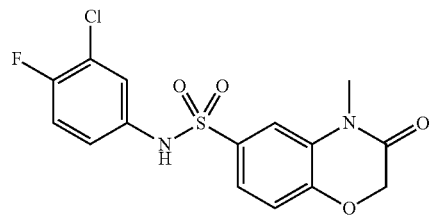 [SMILES: CN1C(=O)COc2ccc(S(=O)(=O)Nc3ccc(F)c(Cl)c3)cc21]

The synthesis of compound 34a was done by following the similar procedure as mentioned for compound 29a by using amine 34 to afford product 34a in 48% yield (0.12 gm) from compound 28 (0.21 gm, 0.82 mmol).

1H NMR (400 MHz, DMSO-d$_6$) δ 3.21 (s, 3H), 4.78 (s, 2H), 7.18-7.03 (m, 2H), 7.27-7.22 (m, 4H), 10.42 (s, 1H).

Synthesis of Compound 35a:

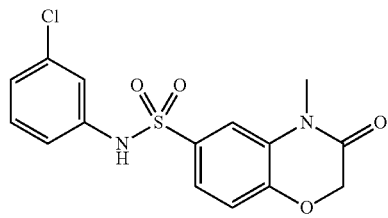 [SMILES: CN1C(=O)COc2ccc(S(=O)(=O)Nc3cccc(Cl)c3)cc21]

The synthesis of compound 35a was done by following the similar procedure as mentioned for compound 29a by using amine 35 to afford product 35a in 48.14% yield (0.13 gm) from compound 28 (0.24 gm, 0.94 mmol).

$^1$H NMR (400 MHz, DMSO-d$_6$) δ 3.22 (s, 3H), 4.78 (s, 2H), 7.21-7.02 (m, 4H), 7.29 (t, 1H), 7.41 (d, 2H), 10.55 (s, 1H).

Synthesis of Compound 36a:

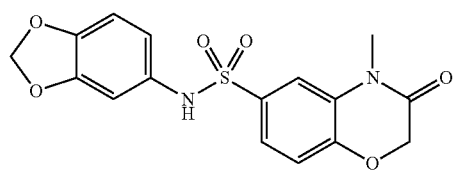 [SMILES: CN1C(=O)COc2ccc(S(=O)(=O)Nc3ccc4c(c3)OCO4)cc21]

The synthesis of compound 36a was done by following the similar procedure as mentioned for compound 29a by using amine 36 to afford product 36a in 63% yield (0.10 gm) from compound 28 (0.15 gm, 0.56 mmol).

$^1$H NMR (400 MHz, DMSO-d$_6$) δ 3.21 (s, 3H), 4.76 (s, 2H), 5.98 (s, 2H), 6.51 (d, 1H), 6.71 (s, 1H), 6.79 (d, 1H), 7.11 (d, 1H), 7.34 (d, 1H), 7.39 (s, 1H), 9.93 (s, 1H); MS: 361 (M−1 peak).

Synthesis of Compound 37a:

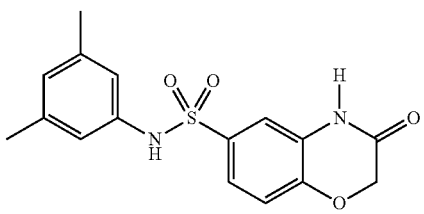 [SMILES: Cc1cc(C)cc(NS(=O)(=O)c2ccc3c(c2)NC(=O)CO3)c1]

To a solution of amine 37 (0.07 gm, 0.57 mmoles) in DCM, sulfonyl chloride 27 (0.17 gm, 0.69 mmoles) was added followed by pyridine (10 mL/gm starting material) at 0° C. and the reaction mixture was allowed to stir at room temperature for 2 hrs. After completion, the reaction mixture was diluted with water and extracted with DCM. The organic layer was washed with 6N HCl and dried over $Na_2SO_4$ and concentrated under reduced pressure to afford product 37a (0.12 gm, 63.15% yield).

$^1$H NMR (500 MHz, DMSO-$d_6$) δ 2.18 (s, 6H), 4.63 (s, 2H), 6.64 (s, 1H), 6.74 (s, 2H), 7.04 (d, 1H), 7.31 (d, 2H), 10.05 (s, 1H), 10.97 (s, 1H); MS: 333 (M+1 peak).

Synthesis of Compound 38a:

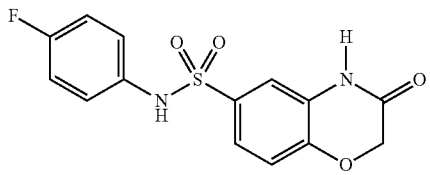 [SMILES: O=C1COc2ccc(S(=O)(=O)Nc3ccc(F)cc3)cc2N1]

The synthesis of compound 38a was done by following the similar procedure as mentioned for compound 37a by using amine 38 to afford product 38a in 65% yield (0.13 gm) from compound 27 (0.19 gm, 0.756 mmol).

$^1$H NMR (500 MHz, DMSO-$d_6$) δ 4.65 (s, 2H), 7.13-7.03 (m, 5H), 7.25 (s, 2H), 10.09 (s, 1H), 10.97 (s, 1H); MS: 320 (M−2 peak).

Synthesis of Compound 39a:

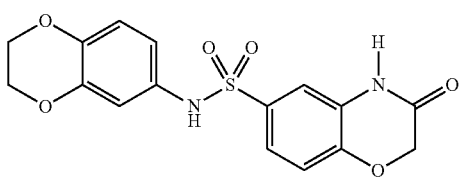 [SMILES: O=C1COc2ccc(S(=O)(=O)Nc3ccc4c(c3)OCCO4)cc2N1]

The synthesis of compound 39a was done by following the similar procedure as mentioned for compound 37a by using amine 39 to afford product 39a in 62% yield (0.10 gm) from compound 27 (0.14 gm, 0.56 mmol).

$^1$H NMR (500 MHz, DMSO-$d_6$) δ 4.18 (s, 4H), 4.66 (s, 2H), 6.53 (d, 1H), 6.60 (s, 1H), 6.74 (s, 1H), 7.06 (d, 1H), 7.2 (d, 2H), 9.92 (s, 1H), 10.93 (s, 1H); MS: 361 (M−1 peak).

Synthesis of Compound 40a:

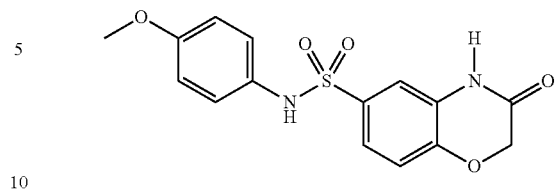

The synthesis of compound 40a was done by following the similar procedure as mentioned for compound 37a by using amine 40 to afford product 40a in 63.15% yield (0.12 gm) from compound 27 (0.17 gm, 0.68 mmol).

$^1$H NMR (500 MHz, DMSO-$d_6$) δ 3.65 (s, 3H), 4.64 (s, 2H), 6.8 (d, 2H), 6.97 (d, 2H), 7.03 (d, 1H), 7.25-7.20 (m, 2H), 9.93 (s, 1H), 10.93 (s, 1H); MS: 332 (M−2 peak).

Scheme 2:

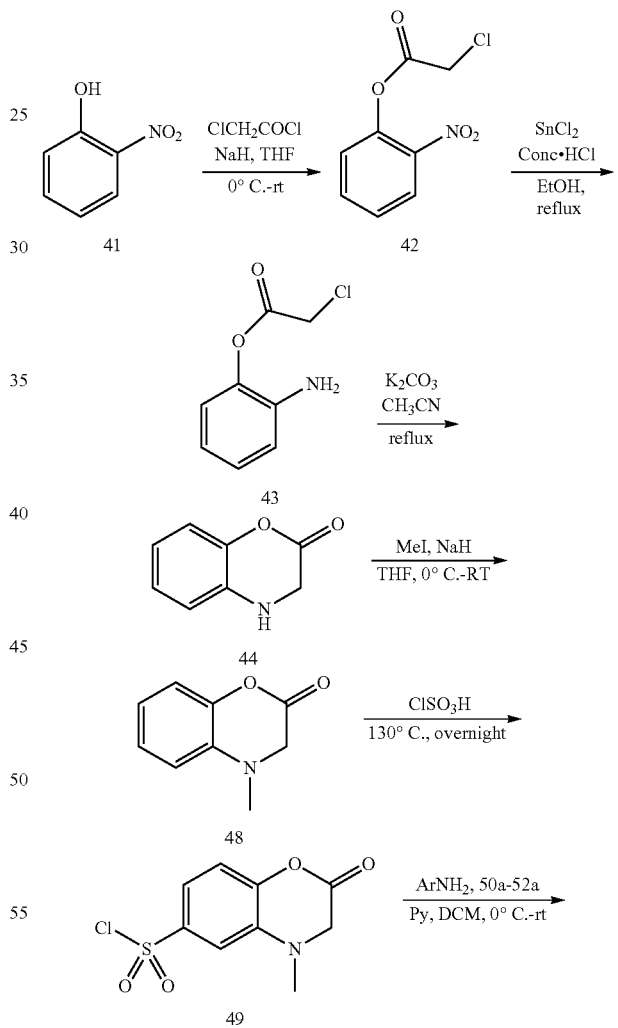

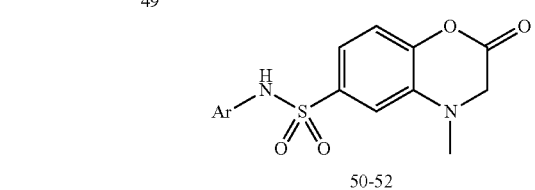

Ar = 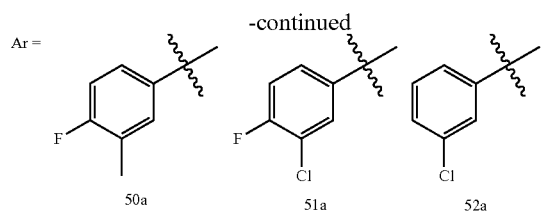

General Procedure for Compound 42:

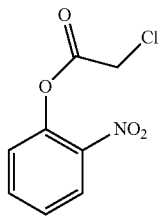

To a stirred suspension of activated NaH (0.24 gm, 10.00 mmol) in THF, 2-nitrophenol (41) (1.0 gm, 7.1 mmol) was added at 0° C. under N$_2$ atmosphere and stirred for 15 min followed by addition of chloroacetyl chloride (1.2 gm, 10.0 mmoles) at the same temperature and allowed to stir at room temperature for 1 hr. After completion of reaction, the mixture was poured into ice and extracted with ethyl acetate. The organic layer dried over Na$_2$SO$_4$ and concentrated under reduced pressure to obtain product 42 in 71% yield (1.1 gm).

General Procedure for Compound 43:

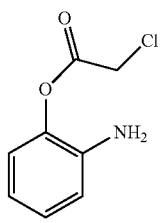 [SMILES: O=C(CCl)Oc1ccccc1[N+](=O)[O-]]

To a stirred solution of nitro compound 42 (6.3 gm, 29.3 mmol) in ethanol was added conc. HCl (5 mL) followed by addition of SnCl$_2$ (33.0 gm, 146.5 mmol) and refluxed for 2 hrs under nitrogen atmosphere. After completion of reaction, ethanol was removed under reduced pressure and the obtained mass was dissolved in water and neutralized with saturated sodium bicarbonate solution and extracted with ethyl acetate. The organic layer dried over Na$_2$SO$_4$ and concentrated to obtain product 43 (1.3 gm; 24.07% yield).

General Procedure for Compound 44:

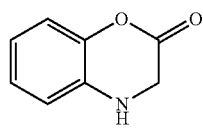 [SMILES: O=C1CNc2ccccc2O1]

To the stirred solution of aniline 43 (1.0 gm, 5.4 mmoles) in acrylonitrile K$_2$CO$_3$ (3.7 gm, 27.0 mmol) was added at room temperature under N$_2$ atmosphere and the resulting mixture was allowed to reflux overnight. After completion of reaction, the mixture was diluted with water and extracted with ethyl acetate. The organic layer dried over Na$_2$SO$_4$ and concentrated under reduced pressure to obtain product (0.80 gm, 100% yield).

General Procedure for Compound 48:

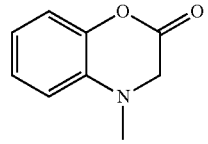

To a solution of NaH (0.072 gms, 3.0 mmol) in THF, amino lactone 44 (0.31 gm, 2.0 mmol) was added at 0° C. slowly and stirred for 30 min followed by addition of MeI (0.21 ml, 3.0 moles) at the same temperature and the resulting mixture was stirred for 1 hr. After completion of reaction, the mixture was poured in ice water and extracted with ethylacetate, dried over Na$_2$SO$_4$, and concentrated under reduced pressure to obtain the product (0.9 gm, 90.0% yield).

General Procedure for Compound 49:

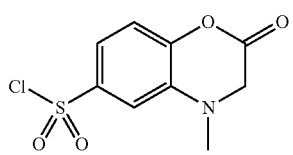

Chlorosulfonic acid (10 ml/gm starting material) was added slowly to amino lactone 48 (1.1 gm, 6.0 moles) in de-aerated RB flask at 0° C. and resulting mixture was heated to 160° C. for overnight. After completion of reaction, the mixture was added to ice and extracted with ethylacetate and the organic layer dried over Na$_2$SO$_4$, and concentrated under reduced pressure to obtain product. (1.0 gm, 58.8% yield).

Synthesis of Compound 50:

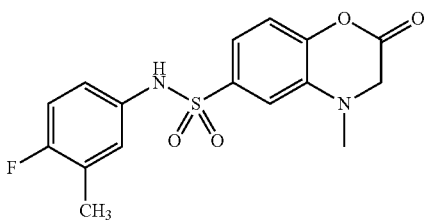 [SMILES: Cc1cc(NS(=O)(=O)c2ccc3c(c2)N(C)CC(=O)O3)ccc1F]

To a solution of sulfonyl chloride 49 (0.2 gm, 0.76 moles) and pyridine (0.15 gm, 1.91 mmol) in DCM, amine 50a (0.14 gm, 1.07 mmoles) was added at 0° C. and the resulting mixture was allowed to stir at room temperature for 3 hrs. After completion of reaction, DCM was removed under reduced pressure and the residue was extracted with ethyl acetate and water. The organic layer was washed with brine and dried over Na$_2$SO$_4$. The organic layer was concentrated to afford product 50 in 74% yield (0.1 gm).

$^1$H NMR (500 MHz, DMSO-d$_6$) δ 2.21 (s, 3H), 3.24 (s, 3H), 4.70 (s, 2H), 6.37 (s, 1H), 6.96-6.80 (m, 3H), 7.00 (d, 1H), 7.39 (d, 1H); MS: 349 (M−1 peak).

Synthesis of Compound 51:

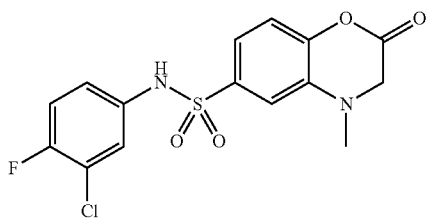 [SMILES: CN1CC(=O)Oc2ccc(S(=O)(=O)Nc3ccc(F)c(Cl)c3)cc21]

The synthesis of compound 51 was done by following the same procedure similar to compound 50 using the compound 51a instead of 50a to get the compound 51 (0.13 gm, 92.19% yield) from compound 49 (0.1 gm, 0.38 mmoles).

$^1$H NMR (500 MHz, DMSO-d$_6$) δ 3.30 (s, 3H), 4.70 (s, 2H), 6.55 (s, 1H), 6.99-6.92 (m, 1H), 7.08-7.01 (m, 3H), 7.20 (br s, 1H), 7.35 (s, 1H), 7.40 (d, 1H); MS: 369 (M−1 peak).

Synthesis of Compound 52:

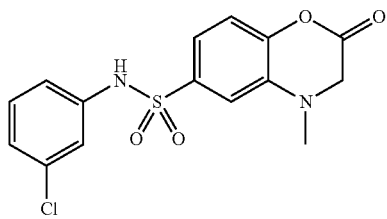 [SMILES: CN1CC(=O)Oc2ccc(S(=O)(=O)Nc3cccc(Cl)c3)cc21]

The synthesis of compound 52 was done from compound 49 (0.2 gm, 0.76 mmol) by following the same procedure similar to compound 50 using the amine 52a instead of 50a to get the compound 52 (0.2 gm, 74.34% yield).

$^1$H NMR (500 MHz, DMSO-d$_6$) δ 3.21 (s, 3H), 4.75 (s, 2H), 7.18-7.02 (m, 3H), 7.28 (t, 1H), 7.41 (d, 2H); MS: 351 (M+1 peak).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method for increasing lifetime of the red blood cells (RBCs) in need thereof comprising contacting blood with an effective amount of (1) a compound of formula (I), (I-II), (I-III), or (I-IV) or a pharmaceutically acceptable salt thereof; (2) a composition comprising a compound of formula (I), (I-II), (I-III), or (I-IV) or a salt thereof, and a carrier or (3) a pharmaceutically acceptable composition comprising a compound of formula (I), (I-II), (I-III), or (I-IV) or a pharmaceutically acceptable salt thereof, and a pharmaceutically acceptable carrier:

formula (I):

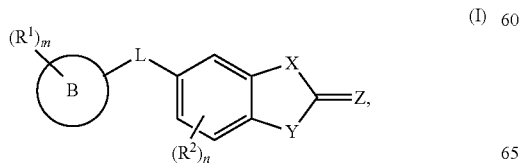

(I)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —NO$_2$, aryl, aralkyl, heteroaryl, —SO$_2$-aryl, —C(O)—NR$^b$-aryl, —C(O)-aralkyl, —C(O)—$C_{1-6}$ alkoxy, —NR$^b$—SO$_2$-aryl, wherein each aryl, aralkyl and heteroaryl group is optionally substituted with 0-3 occurrences of R$^c$ and wherein two $R^1$ groups taken together with the carbon atoms to which they are attached form a heterocyclyl ring;

n is an integer from 1 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —SO$_2$—, —SO$_2$NR$^a$— and —NR$^a$SO$_2$—;

each $R^a$ is independently selected from hydrogen and $C_1$-$C_6$ alkyl;

X and Y are each independently selected from O, S, NR$^b$ and CH$_2$, wherein at least one of X and Y is O or S;

Z is O or S;

each $R^b$ is independently selected from hydrogen, $C_{1-6}$ aralkyl, and $C_1$-$C_6$ alkyl substituted with 0-1 occurrences of R$^c$; and R$^c$ is independently selected from $C_{1-6}$ alkyl, $C_{1-6}$ alkoxy, $C_{1-6}$ haloalkyl, halo, NR$^d$R$^d$, and heterocyclyl and wherein two R$^c$ groups taken together with the carbon atoms to which they are attached form a heterocyclyl ring; and R$^d$ is independently selected from H and $C_{1-6}$ alkyl;

formula (I-II):

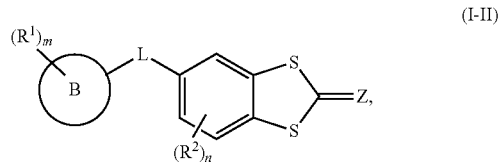

(I-II)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —NO$_2$, aryl, aralkyl, heteroaryl, —SO$_2$-aryl, —C(O)—NR$^b$-aryl, —C(O)-aralkyl, —C(O)—$C_{1-6}$ alkoxy, —NR$^b$—SO$_2$-aryl, wherein each aryl, aralkyl and heteroaryl group is optionally substituted with 0-3 occurrences of R$^c$ and wherein two $R^1$ groups taken together with the carbon atoms to which they are attached form a heterocyclyl ring;

n is an integer from 1 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —SO$_2$—, —SO$_2$NR$^a$— and —NR$^a$SO$_2$—;

each $R^a$ is independently selected from hydrogen and $C_1$-$C_6$ alkyl;

Z is O or S;

each $R^b$ is independently selected from hydrogen, $C_{1-6}$ aralkyl, and $C_1$-$C_6$ alkyl substituted with 0-1 occurrences of R$^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl;

formula (I-III):

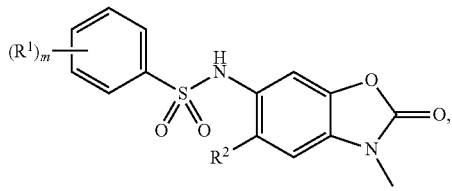

(I-III)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

each $R^2$ is independently selected from $C_1$-$C_6$ alkyl and halo;

each $R^b$ is independently selected from hydrogen, $C_{1-6}$ aralkyl, and $C_1$-$C_6$ alkyl substituted with 0-1 occurrences of $R^c$;

$R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl;

formula (I-IV):

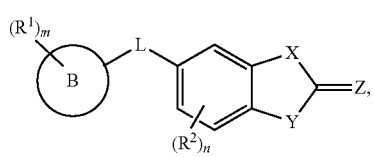

(I-IV)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 0 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —$SO_2$—, —$SO_2NR^a$— and —$NR^aSO_2$—;

each $R^a$ is independently selected from hydrogen and $C_1$-$C_6$ alkyl;

X and Y are each independently selected from O, S, $NR^b$ and $CH_2$;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

2. The method of claim 1, wherein the compound is added directly to whole blood or packed cells extracorporeally.

3. The method of claim 1, wherein the pharmaceutical composition is administered to a subject in need thereof.

4. A method for regulating 2,3-diphosphoglycerate levels in blood in need thereof comprising contacting blood with an effective amount of (1) a compound of formula (I), (I-II), (I-III), or (I-IV) or a pharmaceutically acceptable salt thereof; (2) a composition comprising a compound of formula (I), (I-II), (I-III), or (I-IV) or a salt thereof, and a carrier or (3) a pharmaceutically acceptable composition comprising a compound of formula (I), (I-II), (I-III), or (I-IV) or a pharmaceutically acceptable salt thereof, and a pharmaceutically acceptable carrier; wherein formulae (I), (I-II), (I-III), or (I-IV) are as defined in claim 1.

5. A method for treating hereditary non-spherocytic hemolytic anemia comprising administering to a subject in need thereof a therapeutically effective amount of an effective amount of (1) a compound of formula (I), (I-II), (I-III), or (I-IV) or a pharmaceutically acceptable salt thereof; or (2) a pharmaceutically acceptable composition comprising a compound of formula (I), (I-II), (I-III), or (I-IV) or a pharmaceutically acceptable salt thereof, and a pharmaceutically acceptable carrier; wherein formulae (I), (I-II), (I-III), or (I-IV) are as defined in claim 1.

6. A method for treating sickle cell anemia comprising administering to a subject in need thereof a therapeutically effective amount of an effective amount of (1) a compound of formula (I), (I-II), (I-III), or (I-IV) or a pharmaceutically acceptable salt thereof; or (2) a pharmaceutically acceptable composition comprising a compound of formula (I), (I-II), (I-III), or (I-IV) or a pharmaceutically acceptable salt thereof, and a pharmaceutically acceptable carrier; wherein formulae (I), (I-II), (I-III), or (I-IV) are as defined in claim 1.

7. The method of claim 1, wherein B is monocyclic heteroaryl, cycloalkyl, heterocyclyl, $C_{1-6}$ aralkyl or $C_{1-6}$ heteroaralkyl.

8. The method of claim 7, wherein B is heterocyclyl.

9. The method of claim 8, wherein B is a monocyclic heterocyclyl.

10. The method of claim 9, wherein B is piperizinyl or 1,4-diazepam.

11. The method of claim 9, wherein B is substituted with one $R^1$.

12. The method of claim 1, wherein B is a monocyclic heteroaryl or monocyclic aryl.

13. The method of claim 12, wherein B is pyridyl.

14. The method of claim 12, wherein B is phenyl.

15. The method of claim 13, wherein B is substituted with one or two $R^1$s.

16. The method of claim 1, wherein n is 1.

17. The method of claim 16, wherein the compound of formula (I) is represented by the following formula:

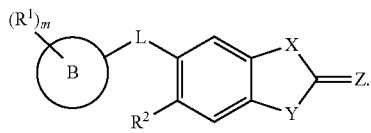

18. The method of claim 16, wherein the compound of formula (I-II) is represented by the following formula:

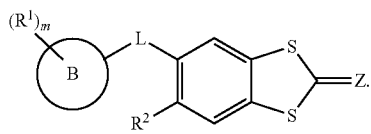

19. The method of claim 1, wherein L is —SO—NR$^a$—.
20. The method of claim 19, wherein R$^a$ is H.
21. The method of claim 1, wherein L is —SO$_2$—.
22. The method of claim 1, wherein each R$^1$ is independently selected from C$_{1-6}$ alkyl, C$_{1-6}$ alkoxy, C$_{1-6}$ haloalkyl, halo, acetyl and —NO$_2$.
23. The method of claim 1, wherein Z is O.
24. The method of claim 1, wherein one of X and Y is O and the other is S.
25. The method of claim 1, wherein one of X and Y is O and the other is NR$^b$.
26. The method of claim 1, wherein one of X and Y is S and the other is NR$^b$.
27. The method of claim 1, wherein m is 0.
28. The method of claim 1, wherein m is 1 or 2.
29. The method of claim 1, wherein each R$^1$ is independently selected from C$_{1-6}$ alkyl, C$_{1-6}$ alkoxy, C$_{1-6}$ haloalkyl, halo, acetyl and —NO$_2$.
30. The method of claim 1, wherein R$^2$ is methyl.
31. A method for increasing lifetime of the red blood cells (RBCs) in need thereof comprising contacting blood with an effective amount of (1) a compound of formula (II), (II-II), (II-III), (II-IV), (II-V), (II-VI), or (II-VII), or a pharmaceutically acceptable salt thereof; (2) a composition comprising a compound of formula (II), (II-II), (II-III), (II-IV), (II-V), (II-VI), or (II-VII), or a salt thereof, and a carrier or (3) a pharmaceutically acceptable composition comprising a compound of formula (II), (II-II), (II-III), (II-IV), (II-V), (II-VI), or (II-VII), or a pharmaceutically acceptable salt thereof, and a pharmaceutically acceptable carrier:

formula (II):

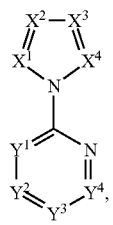

wherein
X$^1$ is N or CE;
X$^2$ is N or CD;
X$^3$ is N or CB;
X$^4$ is N or CA;
Y$^1$, Y$^2$, Y$^3$ and Y$^4$ are each independently selected from N and CR$^1$;
A, B, D and E are each independently selected from H, R$^3$ and —SO$_2$—NR$^4$R$^5$;
wherein at least one of X$^1$, X$^2$, X$^3$, X$^4$, Y$^1$, Y$^2$, Y$^3$ and Y$^4$ is N; and at least one of X$^1$, X$^2$, X$^3$, X$^4$, is C—SO$_2$—NR$^4$R$^5$;
each R$^4$ is independently selected from C$_{1-8}$ alkyl, aryl and heteroaryl, each of which is substituted with n occurrences of R$^2$;
each R$^5$ is independently hydrogen or C$_{1-8}$ alkyl;
each R$^1$ is independently selected from hydrogen, C$_{1-8}$ alkyl, C$_{1-8}$ terminal alkynyl, C$_{1-8}$ alkoxy, halogen, haloalkyl and haloalkoxy;
each R$^2$ is independently selected from halo, haloalkyl, C$_{1-4}$ alkyl, C$_{2-4}$ alkenyl, C$_{2-4}$ alknynyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;
each R$^3$ is independently selected from C$_{1-8}$ alkyl, —OR$^a$, halogen, haloalkyl, haloalkoxy and optionally substituted heteroaryl;
each R$^a$ is independently selected from alkyl, haloalkyl, optionally substituted heteroaryl and optionally substituted heterocyclyl;
each R$^b$ is independently alkyl; and
each R$^c$ is independently selected from hydrogen and alkyl; and
n is 0, 1, 2 or 3;

formula (II-II):

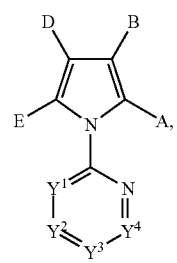

wherein
A, B, D and E are each independently selected from H, —SO$_2$—NR$^4$R$^5$ and R$^3$; wherein at least one of A, B, D, or E is —SO$_2$—NR$^4$R$^5$;
Y$^1$, Y$^2$, Y$^3$ and Y$^4$ are each independently selected from N and CR$^1$, wherein at least one of Y$^1$, Y$^2$, Y$^3$ and Y$^4$ are N;
each R$^4$ is independently selected from C$_{1-8}$ alkyl, aryl and heteroaryl, each of which is substituted with n occurrences of R$^2$;
each R$^5$ is independently hydrogen or C$_{1-8}$ alkyl;
each R$^1$ is independently selected from hydrogen, C$_{1-8}$ alkyl, C$_{1-8}$ terminal alkynyl, C$_{1-8}$ alkoxy, halogen, haloalkyl and haloalkoxy;
each R$^2$ is independently selected from halo, haloalkyl, C$_{1-4}$ alkyl, C$_{2-4}$ alkenyl, C$_{2-4}$ alknynyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy and optionally substituted heteroaryl;

each $R^a$ is independently selected from alkyl, haloalkyl, optionally substituted heteroaryl and optionally substituted heterocyclyl;

each $R^b$ is independently alkyl; and each $R^c$ is independently selected from hydrogen and alkyl; and n is 0, 1, 2 or 3;

formula (II-III):

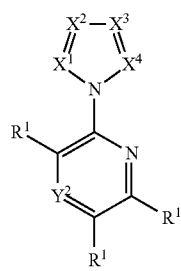

(II-III)

wherein $X^1$ is N or CE;
$X^2$ is N or CD;
$X^3$ is N or CB;
$X^4$ is N or CA, wherein at least one of $X^1$, $X^2$, $X^3$ and $X^4$ is N and at least one of $X^1$, $X^2$, $X^3$, $X^4$, is C—$SO_2$—$NR^4R^5$;

A, B, D and E are each independently selected from H, $R^3$ and —$SO_2$—$NR^4R^5$;

$Y^2$ is selected from N and $CR^1$;

each $R^4$ is independently selected from $C_{1-8}$ alkyl, aryl and heteroaryl, each of which is substituted with n occurrences of $R^2$;

$R^5$ is hydrogen or $C_{1-8}$ alkyl;

each $R^1$ is independently selected from hydrogen, $C_{1-8}$ alkyl, $C_{1-8}$ terminal alkynyl, $C_{1-8}$ alkoxy, halogen, haloalkyl and haloalkoxy;

each $R^2$ is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy and optionally substituted heteroaryl;

each $R^a$ is independently selected from alkyl, haloalkyl, optionally substituted heteroaryl and optionally substituted heterocyclyl;

each $R^b$ is independently alkyl; and each $R^c$ is independently selected from hydrogen and alkyl; and n is 0, 1, 2 or 3;

formula (II-IV):

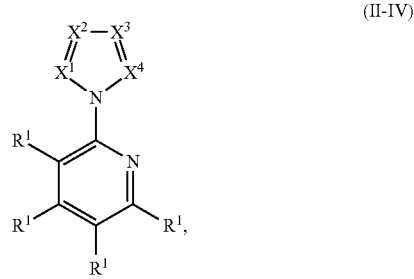

(II-IV)

wherein n is 0, 1, 2 or 3;
$X^1$ is N or CE;
$X^2$ is N or CD;
$X^3$ is N or CB;
$X^4$ is N or CA, wherein at least one of $X^1$, $X^2$, $X^3$ and $X^4$ is N; and and at least one of $X^1$, $X^2$, $X^3$, $X^4$, is C—$SO_2$—$NR^4R^5$;

A, B, D and E are each independently selected from H and —$SO_2$—$NR^4R^5$;

each $R^4$ is independently selected from $C_{1-8}$ alkyl, aryl and heteroaryl, each of which is substituted with n occurrences of $R^2$;

each $R^5$ is independently hydrogen or $C_{1-8}$ alkyl;

each $R^1$ is independently selected from hydrogen, $C_{1-8}$ alkyl, $C_{1-8}$ alkoxy, halogen, haloalkyl and haloalkoxy;

each $R^2$ is independently selected from halo, haloalkyl, $C_{1-4}$alkyl, $C_{2-4}$ alkenyl, $C_{2-4}$ alkynylheteroaryl, aryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy or optionally substituted heteroaryl;

$R^a$ is independently selected from alkyl, haloalkyl, optionally substituted heteroaryl and optionally substituted heterocyclyl;

each $R^b$ is independently alkyl; and each $R^c$ is independently selected from hydrogen and alkyl;

formula (II-V):

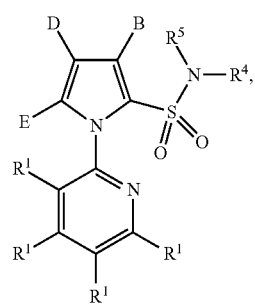

(II-V)

wherein

B, D and E are each independently selected from H and $R^3$;

each $R^1$ is independently selected from hydrogen, halo and haloalkyl;

$R^4$ is hydrogen, $C_{1-8}$ alkyl, and aryl, substituted with n occurrences of $R^2$;

each $R^2$ is independently selected from halo, haloalkyl, alkyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from halo, haloalkyl and —$OR^a$;

$R^5$ is hydrogen or $C_{1-8}$ alkyl;

$R^a$ is independently selected from alkyl, haloalkyl, optionally substituted heteroaryl and optionally substituted heterocyclyl;

each $R^b$ is independently alkyl;

each $R^c$ is independently selected from hydrogen and alkyl; and n is 0, 1, 2 or 3;

formula (II-VI):

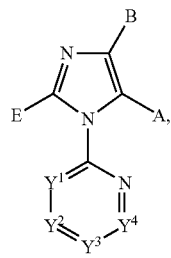

wherein
A, B and E are each independently selected from H, —$SO_2$—$NR^4R^5$ and $R^3$; wherein at least one of A, B or E is —$SO_2$—$NR^4R^5$;

$Y^1, Y^2, Y^3$ and $Y^4$ are each independently selected from N and $CR^1$, wherein at least one of $Y^1, Y^2, Y^3$ and $Y^4$ are N;

each $R^4$ is independently selected from $C_{1-8}$ alkyl, aryl and heteroaryl, each of which is substituted with n occurrences of $R^2$;

each $R^5$ is independently hydrogen or $C_{1-8}$ alkyl;

each $R^1$ is independently selected from hydrogen, $C_{1-8}$ alkyl, $C_{1-8}$ terminal alkynyl, $C_{1-8}$ alkoxy, halogen, haloalkyl and haloalkoxy;

each $R^2$ is independently selected from halo, haloalkyl, $C_{1-4}$ alkyl, $C_{2-4}$ alkenyl, $C_{2-4}$ alknynyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy and optionally substituted heteroaryl;

each $R^a$ is independently selected from alkyl, haloalkyl, optionally substituted heteroaryl and optionally substituted heterocyclyl;

each $R^b$ is independently alkyl; and each $R^c$ is independently selected from hydrogen and alkyl; and n is 0, 1, 2 or 3;

formula (II-VII):

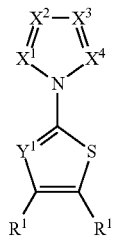

wherein
$X^1$ is N or CE;
$X^2$ is N or CD;
$X^3$ is N or CB;
$X^4$ is N or CA, wherein at least one of $X^1, X^2, X^3$ and $X^4$ is N and at least one of $X^1, X^2, X^3, X^4$, is C—$SO_2$—$NR^4R^5$;

A, B, D and E are each independently selected from H, $R^3$ and —$SO_2$—$NR^4R^5$;

$Y^1$ is selected from N and $CR^1$;

each $R^4$ is independently selected from $C_{1-8}$ alkyl, aryl and heteroaryl, each of which is substituted with n occurrences of $R^2$;

$R^5$ is hydrogen or $C_{1-8}$ alkyl;

each $R^1$ is independently selected from hydrogen, $C_{1-8}$ alkyl, $C_{1-8}$ terminal alkynyl, $C_{1-8}$ alkoxy, halogen, haloalkyl and haloalkoxy;

each $R^2$ is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy and optionally substituted heteroaryl;

each $R^a$ is independently selected from alkyl, haloalkyl, optionally substituted heteroaryl and optionally substituted heterocyclyl;

each $R^b$ is independently alkyl; and each $R^c$ is independently selected from hydrogen and alkyl; and n is 0, 1, 2 or 3.

32. The method of claim 31, wherein the compound is added directly to whole blood or packed cells extracorporeally.

33. The method of claim 31, wherein the pharmaceutical composition is administered to a subject in need thereof.

34. A method for regulating 2,3-diphosphoglycerate levels in blood in need thereof comprising contacting blood with an effective amount of (1) a compound of formula (II), (II-II), (II-III), (II-IV), (II-V), (II-VI), or (II-VII), or a pharmaceutically acceptable salt thereof; (2) a composition comprising a compound of formula (II), (II-II), (II-III), (II-IV), (II-V), (II-VI), or (II-VII), or a salt thereof, and a carrier; or (3) a pharmaceutically acceptable composition comprising a compound of formula (II), (II-II), (II-III), (II-IV), (II-V), (II-VI), or (II-VII), or a pharmaceutically acceptable salt thereof, and a pharmaceutically acceptable carrier; wherein formulae (II), (II-II), (II-III), (II-IV), (II-V), (II-VI), and (II-VII), are as defined in claim 31.

35. A method for treating hereditary non-spherocytic hemolytic anemia comprising administering to a subject in need thereof a therapeutically effective amount of an effective amount of (1) a compound of formula (II), (II-II), (II-III), (II-IV), (II-V), (II-VI), or (II-VII), or a pharmaceutically acceptable salt thereof; or (2) a pharmaceutically acceptable composition comprising a compound of formula (II), (II-II), (II-III), (II-IV), (II-V), (II-VI), or (II-VII), or a pharmaceutically acceptable salt thereof, and a pharmaceutically acceptable carrier; wherein formulae (II), (II-II), (II-III), (II-IV), (II-V), (II-VI), and (II-VII) are as defined in claim 31.

36. A method for treating sickle cell anemia comprising administering to a subject in need thereof a therapeutically effective amount of an effective amount of (1) a compound of formula (II), (II-II), (II-III), (II-IV), (II-V), (II-VI), or (II-VII), or a pharmaceutically acceptable salt thereof; or (2) a pharmaceutically acceptable composition comprising a compound of formula (II), (II-II), (II-III), (II-IV), (II-V), (II-VI), or (II-VII), or a pharmaceutically acceptable salt thereof, and a pharmaceutically acceptable carrier; wherein formulae (II), (II-II), (II-III), (II-IV), (II-V), (II-VI), and (II-VII), are as defined in claim 31.

37. The method of claim 31, wherein the compound is selected from formula (II-II):

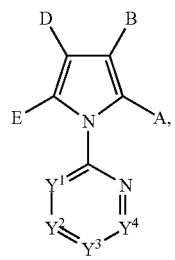

(II-II)

wherein
A, B, D and E are each independently selected from H, —SO$_2$—NR$^4$R$^5$ and R$^3$; wherein at least one of A, B, D, or E is —SO$_2$—NR$^4$R$^5$;
Y$_1$, Y$^2$, Y$^3$ and Y$^4$ are each independently selected from N and CR$^1$, wherein at least one of Y$^1$, Y$^2$, Y$^3$ and Y$^4$ are N;
each R$^4$ is independently selected from C$_{1-8}$ alkyl, aryl and heteroaryl, each of which is substituted with n occurrences of R$^2$;
each R$^5$ is independently hydrogen or C$_{1-8}$ alkyl;
each R$^1$ is independently selected from hydrogen, C$_{1-8}$ alkyl, C$_{1-8}$ terminal alkynyl, C$_{1-8}$ alkoxy, halogen, haloalkyl and haloalkoxy;
each R$^2$ is independently selected from halo, haloalkyl, C$_{1-4}$ alkyl, C$_{2-4}$ alkenyl, C$_{2-4}$ alknynyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;
each R$^3$ is independently selected from C$_{1-8}$ alkyl, —OR$^a$, halogen, haloalkyl, haloalkoxy and optionally substituted heteroaryl;
each R$^a$ is independently selected from alkyl, haloalkyl, optionally substituted heteroaryl and optionally substituted heterocyclyl;
each R$^b$ is independently alkyl; and
each R$^c$ is independently selected from hydrogen and alkyl; and
n is 0, 1, 2 or 3.

38. The method of claim 31, wherein the compound is selected from formula (II-Va):

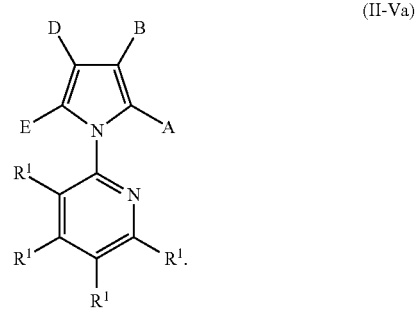

(II-Va)

wherein
B and D are each independently selected from H and SO$_2$NR$^4$R$^5$; wherein at least one of B or D is —SO$_2$—NR$^4$R$^5$;
A and E are each independently selected from H and R$^3$;
each R$^1$ is independently selected from hydrogen, halo and haloalkyl;
R$^4$ is hydrogen, C$_{1-8}$ alkyl, and aryl, substituted with n occurrences of R$^2$;
each R$^2$ is independently selected from halo, haloalkyl, alkyl, aryl, heteroaryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;
each R$^3$ is independently selected from halo, haloalkyl and —OR$^a$;
R$^5$ is hydrogen or C$_{1-8}$ alkyl;
R$^a$ is independently selected from alkyl, haloalkyl, optionally substituted heteroaryl and optionally substituted heterocyclyl;
each R$^b$ is independently alkyl;
each R$^c$ is independently selected from hydrogen and alkyl; and
n is 0, 1, 2, or 3.

39. A method for increasing lifetime of the red blood cells (RBCs) in need thereof comprising contacting blood with an effective amount of (1) a compound of formula (III), or a pharmaceutically acceptable salt thereof; (2) a composition comprising a compound of formula (III) or a salt thereof, and a carrier or (3) a pharmaceutically acceptable composition comprising a compound of formula (III) or a pharmaceutically acceptable salt thereof, and a pharmaceutically acceptable carrier:

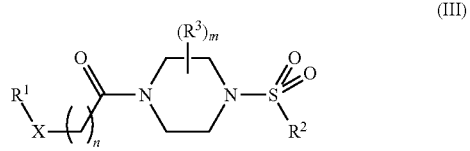

(III)

wherein:
m is 0, 1 or 2;
n is 0, 1 or 2;
X is O, S, NR$^b$, alkylenyl, cycloalkylenyl, or a bond;
R$^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl;

$R^2$ is an optionally substituted aryl or an optionally substituted heteroaryl;

each $R^3$ is independently selected from halo, alkyl, haloalkyl and —$OR^a$;

each $R^a$ is independently selected from alkyl, haloalkyl and optionally substituted heteroaryl; and each $R^b$ is independently hydrogen or alkyl.

40. The method of claim 39, wherein the compound is added directly to whole blood or packed cells extracorporeally.

41. The method of claim 39, wherein the pharmaceutical composition is administered to a subject in need thereof.

42. A method for regulating 2,3-diphosphoglycerate levels in blood in need thereof comprising contacting blood with an effective amount of (1) a compound of formula (III), or a pharmaceutically acceptable salt thereof; (2) a composition comprising a compound of formula (III) or a salt thereof, and a carrier or (3) a pharmaceutically acceptable composition comprising a compound of formula (III) or a pharmaceutically acceptable salt thereof, and a pharmaceutically acceptable carrier; wherein formula (III) is as defined in claim 39.

43. A method for treating hereditary non-spherocytic hemolytic anemia comprising administering to a subject in need thereof a therapeutically effective amount of an effective amount of (1) a compound of formula (III), or a pharmaceutically acceptable salt thereof; or (2) a pharmaceutically acceptable composition comprising a compound of formula (III) or a pharmaceutically acceptable salt thereof, and a pharmaceutically acceptable carrier; wherein formula (III) is as defined in claim 39.

44. A method for treating sickle cell anemia comprising administering to a subject in need thereof a therapeutically effective amount of an effective amount of (1) a compound of formula (III), or a pharmaceutically acceptable salt thereof; or (2) a pharmaceutically acceptable composition comprising a compound of formula (III) or a pharmaceutically acceptable salt thereof, and a pharmaceutically acceptable carrier; wherein formula (III) is as defined in claim 39.

45. The method of claim 39, wherein the compound is selected from formula (III-II)

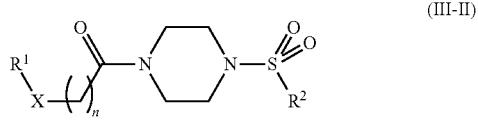

(III-II)

wherein:
n is 0, 1 or 2;
X is O, S, $NR^b$, or cycloalkylenyl;
$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl; provided that when n is 0 and X is O, then $R^1$ is selected from optionally substituted aryl, optionally substituted heteroaryl, optionally substituted heterocyclyl, optionally substituted cycloalkyl, an optionally substituted aralkyl, or optionally substituted heteroaralkyl;
$R^2$ is a bicyclic heteroaryl; and
each $R^b$ is independently hydrogen or alkyl.

46. The method of claim 39, wherein the compound is selected from formula (III-II-a):

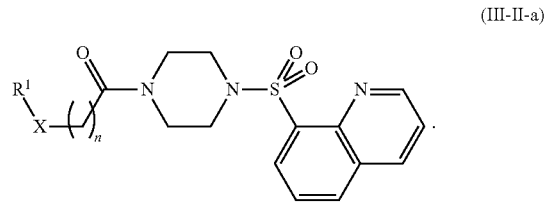

(III-II-a)

47. The method of claim 39, wherein the compound is selected from formula (III-III):

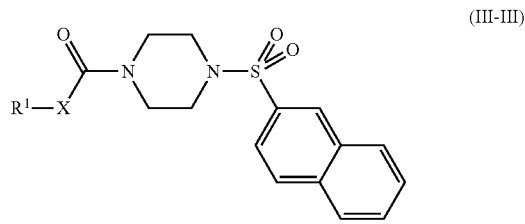

(III-III)

wherein:
when X is S, $NR^b$, or cycloalkylenyl, $R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl;
when X is O, $R^1$ is selected from an optionally substituted aralkyl, or optionally substituted heteroaralkyl; and
each $R^b$ is independently hydrogen or alkyl.

48. The method of claim 39, wherein the compound is selected from formula (III-IV):

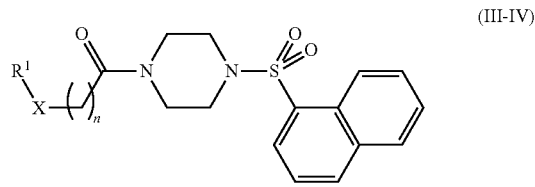

(III-IV)

or a pharmaceutically acceptable salt thereof, wherein:
when n is 0, X is S, $NR^b$, or cycloalkylenyl;
when n is 1 or 2, X is O, X is S, $NR^b$, or cycloalkylenyl;
$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl; and
each $R^b$ is independently hydrogen or alkyl.

49. The method of claim 39, wherein m is 0.

50. The method of claim 39, wherein X is oxygen (O), sulfur (S), or cycloalkylenyl.

51. The method of claim 39, wherein $R^1$ is an optionally substituted aryl, an optionally substituted aralkyl or an optionally substituted heteroaryl.

52. The method of claim 51, wherein $R^1$ is optionally substituted phenyl.

53. The method of claim 51, wherein $R^1$ is optionally substituted benzyl.

54. The method of claim 51, wherein $R^1$ is optionally substituted pyridyl.

55. The method of claim 51, wherein $R^1$ is optionally substituted naphthyl.

56. The method of claim 39, wherein $R^2$ is optionally substituted phenyl.

57. The method of claim 39, wherein $R^2$ is optionally substituted naphthyl.

58. The method of claim 39, wherein $R^2$ is optionally substituted quinolyl.

59. A method for increasing lifetime of the red blood cells (RBCs) in need thereof comprising contacting blood an effective amount of (1) a compound of formula (IV), (V), (VI), or (VII), or a pharmaceutically acceptable salt thereof; (2) a composition comprising a compound of formula (IV), (V), (VI), or (VII), or a salt thereof, and a carrier or (3) a pharmaceutically acceptable composition comprising a compound of formula (IV), (V), (VI), or (VII), or a pharmaceutically acceptable salt thereof, and a pharmaceutically acceptable carrier:

formula (IV):

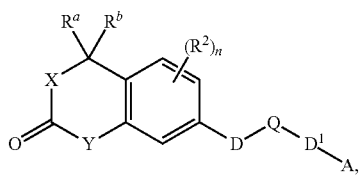

(I)

or a pharmaceutically acceptable salt thereof, wherein:
X and Y are each independently selected from O and N(-L-$R^1$);
Q is C(O), SO$_2$, or —(CH$_2$)$_h$—;
each L is independently selected from a bond, —C(O)—, —(CR$^a$R$^b$)$_m$—, —C(O)N(R$^c$)— or —C(O)O—;
D and D$^1$ are each independently selected from a bond, O and N(R$^c$), provided that D and D$^1$ are not both a bond;
A is aryl or heteroaryl, each of which is substituted with 0-3 occurrences of R$^d$; and D-Q-D$^1$-A is not OCH$_2$-phenyl;
each $R^1$ is independently selected from hydrogen, C$_{1-4}$ alkyl, halo C$_{1-4}$alkyl, alkyl-O-alkylene, C$_{3-10}$ cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of R$^f$ and each alkyl and haloalkyl is substituted with 0-3 occurrences of R$^g$;
each R$^a$ and each R$^b$ are independently selected from hydrogen, C$_{1-4}$ alkyl, or R$^a$ and R$^b$ bound to the same carbon atom are taken together with the carbon atom to form a cycloalkyl;
each R$^c$ is independently selected from hydrogen and C$_{1-4}$ alkyl;
each R$^d$ is independently selected from halo, halo C$_{1-4}$ alkyl, C$_{1-4}$ alkyl, nitro, cyano, —OH and —O(C$_{1-4}$ alkyl), or two R$^d$, attached to the same or adjacent carbon atoms, taken together with the atom(s) to which they are attached form an optionally substituted heterocyclyl;
each R$^f$ is independently selected from halo, halo C$_{1-4}$alkyl, C$_{1-4}$ alkyl, nitro, cyano, —OH and —O(C$_{1-4}$ alkyl), or two R$^f$, attached to the same or adjacent carbon atoms, taken together with the atoms to which they are attached form an optionally substituted heterocyclyl;
each R$^g$ is independently selected from nitro, cyano, —OH, —O(C$_{1-4}$ alkyl) or two R$^g$, attached to the same or adjacent carbon atoms, taken together with the atoms to which they are attached form an optionally substituted heterocyclyl;
each $R^2$ is independently selected from halo, halo C$_{1-4}$ alkyl, C$_{1-4}$ alkyl, C$_{1-4}$ alkoxy and hydroxyl;
h is 1, 2 or 3;
each m is independently 1, 2 or 3; and
each n is independently 0, 1, 2 or 3;
provided that the compound is not 2-chloro-N-(1,4-dihydro-2-oxo-2H-3,1-benzoxazin-7-yl)-5-[[(1-methylethyl)amino]sulfonyl]-benzamide;
4-[2-oxo-7-(phenylmethoxy)-2H-1,3-benzoxazin-3(4H)-yl], Benzoic methyl ester;
2-chloro-5-[[(1-methylethyl)amino]sulfonyl]-N-(1,2,3,4-tetrahydro-2-oxo-7-quinazolinyl)-benzamide; or
2-chloro-5-[[(1-methylethyl)amino]sulfonyl]-N-(1,2,3,4-tetrahydro-3-methyl-2-oxo-7-quinazolinyl)-benzamide;

formula (V):

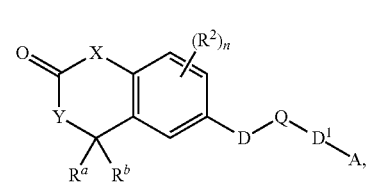

(V)

or a pharmaceutically acceptable salt thereof, wherein:
X and Y are each independently selected from O and N-L-$R^1$;
Q is C(O), SO$_2$, or —(CH$_2$)$_h$—;
each L is independently selected from a bond, —C(O)—, —(CR$^a$R$^b$)$_m$—, —C(O)NR$^c$— or —C(O)O—;
D and D$^1$ are each independently selected from a bond, O and NR$^c$, provided that D and D$^1$ are not both a bond;
A is aryl or heteroaryl, each of which is substituted with 0-3 occurrences of R$^d$;
each $R^1$ is independently selected from hydrogen, C$_{1-4}$ alkyl, haloC$_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of R$^f$ and each alkyl and haloalkyl is substituted with 0-3 occurrences of R$^g$;
each R$^a$ and each R$^b$ are independently selected from hydrogen, C$_{1-4}$ alkyl, or R$^a$ and R$^b$ bound to the same carbon atom are taken together with the carbon atom to form a cycloalkyl;
each R$^c$ is independently selected from hydrogen and C$_{1-4}$ alkyl;
each R$^d$ is independently selected from halo, halo C$_{1-4}$ alkyl, C$_{1-4}$ alkyl, nitro, cyano, —OH and —O(C$_{1-4}$ alkyl), or two R$^d$, attached to the same or adjacent carbon atoms, taken together with the atoms to which they are attached form an optionally substituted heterocyclyl;
each R$^f$ is independently selected from halo, halo C$_{1-4}$ alkyl, C$_{1-4}$ alkyl, nitro, cyano, —OH and —O(C$_{1-4}$ alkyl), or two R$^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3;

each m is independently 1, 2 or 3; and each n is independently 0, 1, 2 or 3; provided that 1) D-Q-$D^1$-A is not i) O-benzyl, ii) NHSO$_2$-2-thiophenyl, iii) NHC(O)-optionally substituted phenyl, or iv) NHSO$_2$-optionally substituted phenyl; and 2) the compound is not:
  i) N-(2,6-dimethylphenyl)-1,2,3,4-tetrahydro-1,3-dimethyl-2-oxo-6-Quinazolinesulfonamide;
  ii) N-[2-[[[(1S)-2-cyclohexyl-1-methylethyl]amino]methyl]phenyl]-1,4-dihydro-2-oxo-2H-3,1-Benzoxazine-6-sulfonamide; or
  iii) N-[2-[[[(1S)-2-cyclopentyl-1-methylethyl]amino]methyl]phenyl]-1,4-dihydro-2-oxo-2H-3,1-Benzoxazine-6-sulfonamide;

formula (VI):

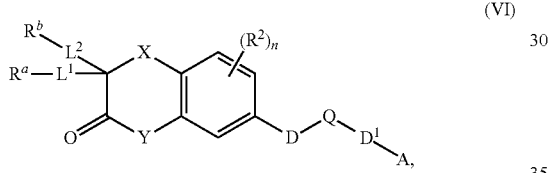

(VI)

or a pharmaceutically acceptable salt thereof, wherein:

X and Y are each independently selected from O and N—$R^1$;

Q is C(O), SO$_2$, or —(CH$_2$)$_h$—;

$L^1$ and $L^2$ are each independently selected from a bond, —O—, C(O)—, —C(O)O—, —OC(O)—, —C(O)NR$^c$—, —NR$^c$C(O)—, —S—, —SO— and —SO$_2$—;

D and $D^1$ are each independently selected from a bond, O and NR$^c$, provided that D and $D^1$ are not both a bond;

A is aryl or heteroaryl, each of which is substituted with 0-3 occurrences of $R^f$;

each $R^1$ is independently selected from hydrogen or $C_{1-4}$ alkyl, wherein each $C_{1-4}$ alkyl is substituted with 0-3 occurrences of $R^f$;

$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or one of $R^a$ or $R^b$ is taken together with $R^1$ and the atoms to which they are respectively attached to form an optionally substituted five-membered heterocylyl;

each $R^c$ is independently selected from hydrogen and $C_{1-4}$ alkyl;

each $R^d$ is independently selected from halo, halo $C_{1-4}$ alkyl, $C_{1-4}$ alkyl, nitro, —NR$^c$R$^c$, —NHCH(NR$^c$R$^c$)NR$^c$R$^c$, —NHC(=NR$^c$R$^c$)NR$^c$R$^c$, —C(O)NR$^c$R$^c$, cyano, —SR$^c$ and —OR$^c$, or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3; and n is 0, 1, 2 or 3; provided that

1) D-Q-$D^1$-A is not —SO$_3$-phenyl or —SO$_3$-p-methylphenyl;

2) when Y is NR$^c$, then Q is not C(O);

3) when Y is NH, D-Q-$D^1$- is not SO$_2$NR$^c$ or NR$^c$SO$_2$; and 4) the compound is not:
  i) N-(3-fluoro-2-methylphenyl)-3,4-dihydro-4-methyl-3-oxo-2H-1,4-benzoxazine-6-sulfonamide;
  ii) methyl 4,5-dimethoxy-2-(4-methyl-3-oxo-3,4-dihydro-2H-benzo[b][1,4]oxazine-6-sulfonamido)-phenethylcarbamate;
  iii) 1-(difluoromethyl)-N-(3,4-dihydro-4-methyl-3-oxo-2H-1,4-benzoxazin-6-yl)-5-methyl-1H-pyrazole-4-sulfonamide;
  iv) N-(3,4-dihydro-4-methyl-3-oxo-2H-1,4-benzoxazin-6-yl)-4-fluoro-3-methyl-benzenesulfonamide;
  v) 7-chloro-N-(3,4-dihydro-4-methyl-3-oxo-2H-1,4-benzoxazin-6-yl)-2,3-dihydro-1,4-benzodioxin-6-sulfonamide;
  vi) N-(3,4-dihydro-4-methyl-3-oxo-2H-1,4-benzoxazin-6-yl)-1,5-dimethyl-1H-pyrazole-4-sulfonamide;
  vii) N-(3,4-dihydro-4-methyl-3-oxo-2H-1,4-benzoxazin-6-yl)-2-fluoro-5-methyl-benzenesulfonamide; or
  viii) 5-chloro-N-(3,4-dihydro-4-methyl-3-oxo-2H-1,4-benzoxazin-6-yl)-2,4-dimethoxy-benzenesulfonamide; or formula (VII):

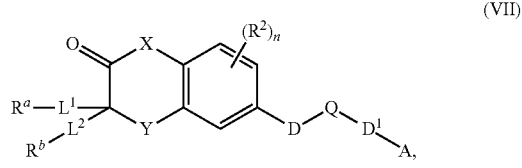

(VII)

or a pharmaceutically acceptable salt thereof, wherein:

X and Y are each independently selected from O and N—$R^1$;

Q is C(O), SO$_2$, or —(CH$_2$)$_h$—;

$L^1$ and $L^2$ are each independently selected from a bond, —O—, C(O)—, —C(O)O—, —OC(O)—, —C(O)NR$^c$—, —NR$^c$C(O)—, —S—, —SO— and —SO$_2$—;

D and $D^1$ are each independently selected from a bond, O and NR$^c$, provided that D and $D^1$ are not both a bond;

A is aryl or heteroaryl, each of which is substituted with 0-3 occurrences of $R^d$;

each $R^1$ is independently selected from hydrogen or $C_{1-4}$ alkyl; wherein each $C_{1-4}$ alkyl is substituted with 0-3 occurrences of $R^f$;

$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocycloalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or one of $R^a$ or $R^b$ is taken together with a Y—$R^1$ or X—$R^1$ and the atoms to which they are respectively attached to form an optionally substituted five-membered heterocyclyl;

each $R^c$ is independently selected from hydrogen and $C_{1-4}$ alkyl;

each $R^d$ is independently selected from halo, halo $C_{1-4}$ alkyl, $C_{1-4}$ alkyl, nitro, —NR$^c$R$^c$, —NHCH(NR$^c$R$^c$)NR$^c$R$^c$, —NHC(=NR$^c$R$^c$)NR$^c$R$^c$, —C(O)NR$^c$R$^c$, cyano, —SR$^c$ and —OR', or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3; and n is 0, 1, 2 or 3; provided that:

1) D-Q-$D^1$-A is not O-benzyl;
2) when Y is O, X is not N—$R^1$; and
3) the compound of formula (IV) is not:
(E)-N-(3,3-dimethyl-2-oxo-3,4-dihydro-2H-benzo[b][1,4]oxazin-6-yl)-4-(3,3,3-trifluoroprop-1-en-1-yl)benzamide;
(E)-N-(3,3-dimethyl-2-oxo-3,4-dihydro-2H-benzo[b][1,4]oxazin-6-yl)-N-methyl-4-(3,3,3-trifluoroprop-1-en-1-yl)benzamide;
3-[2-(4-bromophenyl)-2-oxoethyl]-3,4-dihydro-6-methyl-2H-1,4-benzoxazin-2-one; or
4-[[(3,4-dihydro-2-oxo-2H-1,4-benzoxazin-6-yl)amino]sulfonyl]-5-methyl-2-furancarboxylic acid ethyl ester.

60. The method of claim 59, wherein the compound is added directly to whole blood or packed cells extracorporeally.

61. The method of claim 59, wherein the pharmaceutical composition is administered to a subject in need thereof.

62. A method for regulating 2,3-diphosphoglycerate levels in blood in need thereof comprising contacting blood an effective amount of (1) a compound of formula (IV), (V), (VI) or (VII), or a pharmaceutically acceptable salt thereof; (2) a composition comprising a compound of formula (IV), (V), (VI) or (VII), or a salt thereof, and a carrier; or (3) a pharmaceutically acceptable composition comprising a compound of formula (IV), (V), (VI) or (VII), or a pharmaceutically acceptable salt thereof, and a pharmaceutically acceptable carrier; wherein formulae (IV), (V), (VI) and (VII) are as defined in claim 59.

63. A method for treating hereditary non-spherocytic hemolytic anemia comprising administering to a subject in need thereof a therapeutically effective amount of an effective amount of (1) a compound of formula (IV), (V), (VI) or (VII), or a pharmaceutically acceptable salt thereof; or (2) a pharmaceutically acceptable composition comprising a compound of formula (IV), (V), (VI) or (VII), or a pharmaceutically acceptable salt thereof, and a pharmaceutically acceptable carrier; wherein formulae (IV), (V), (VI) and (VII) are as defined in claim 59.

64. A method for treating sickle cell anemia comprising administering to a subject in need thereof a therapeutically effective amount of an effective amount of (1) a compound of formula (IV), (V), (VI) or (VII), or a pharmaceutically acceptable salt thereof; or (2) a pharmaceutically acceptable composition comprising a compound of formula (IV), (V), (VI) or (VII), or a pharmaceutically acceptable salt thereof, and a pharmaceutically acceptable carrier; wherein formulae (IV), (V), (VI) and (VII) are as defined in claim 59.

65. The method of claim 59, wherein the compound is a compound of formula (IVa):

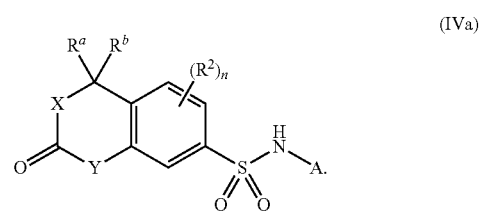

66. The method of claim 59, selected from any one of the compounds below:

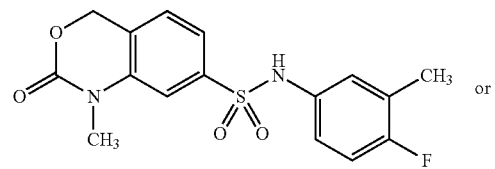

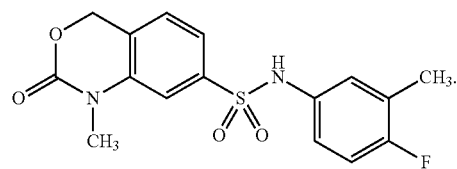

67. The method of claim 59, wherein the compound is a compound of formula (Va):

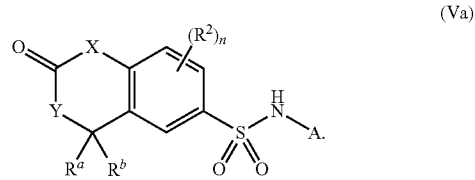

68. The method of claim 59, selected from any one of the compounds below:
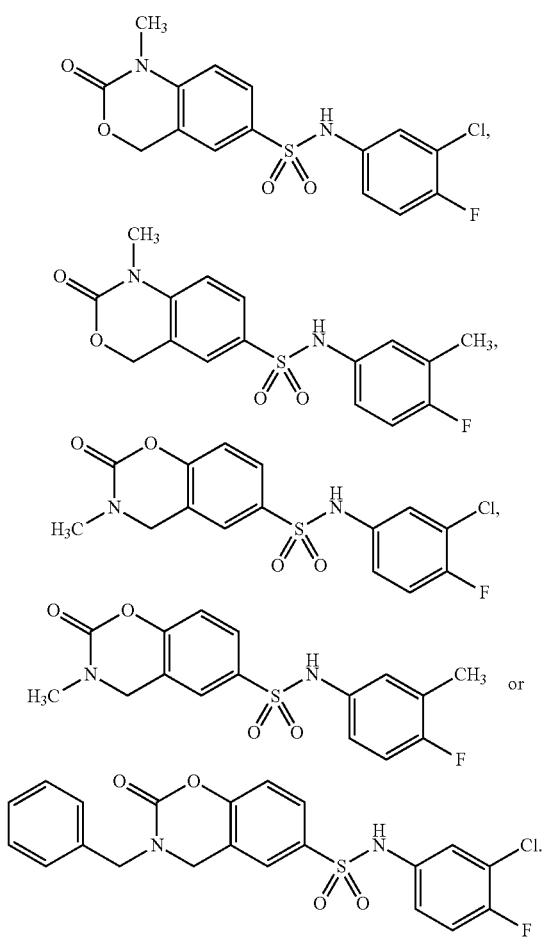
69. The method of claim 59, wherein the compound is a compound of formula (VIa):
(VIa)
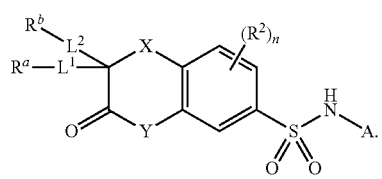
70. The method of claim 59, selected from any one of the compounds below:
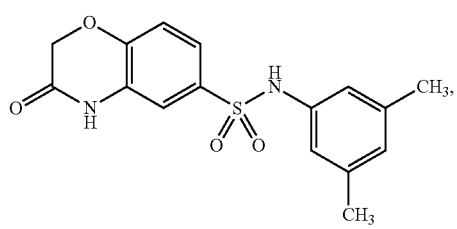
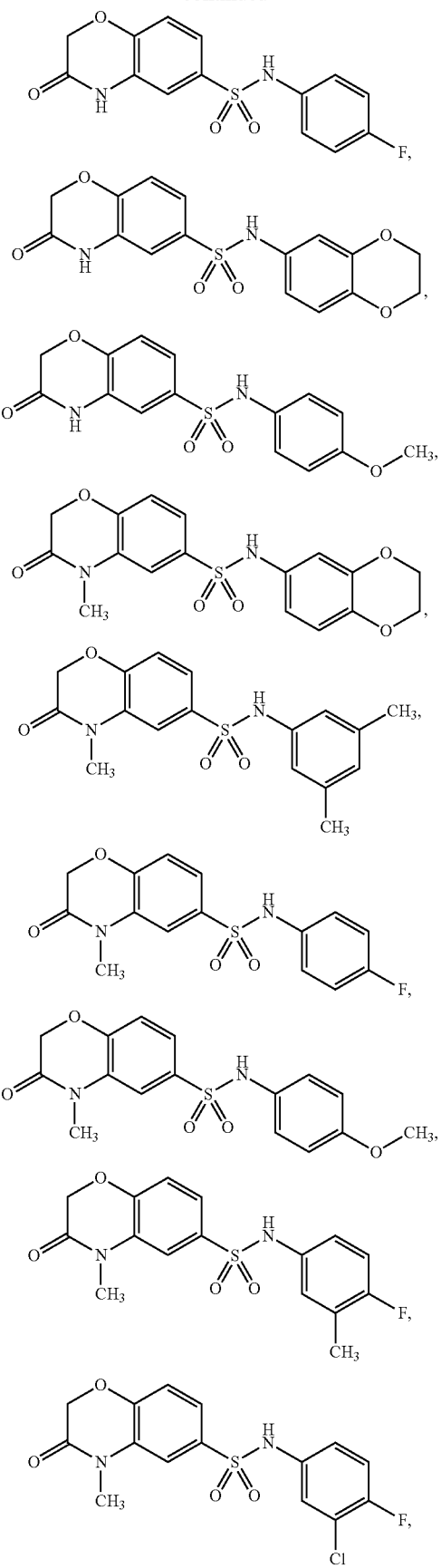

-continued
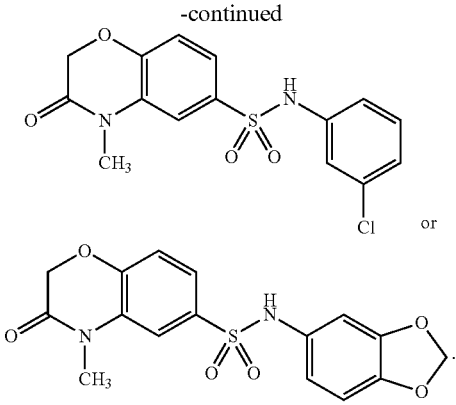
or
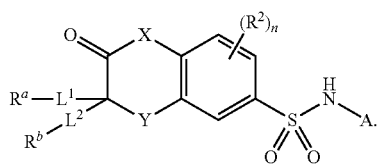
71. The method of claim 59, wherein the compound is a compound of formula (VIIa):
(VIIa)
72. The method of claim 59, selected from any one of the compounds below:
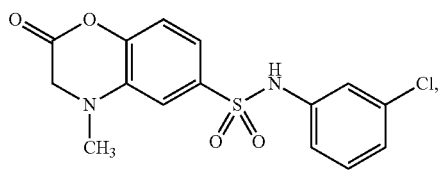
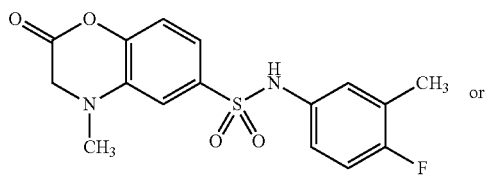
or
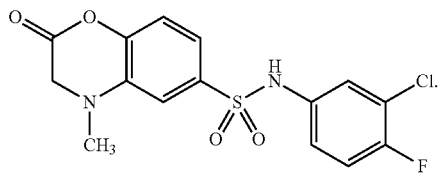
* * * * *